United States Patent
Corkum et al.

(10) Patent No.: US 11,264,221 B2
(45) Date of Patent: Mar. 1, 2022

(54) HIGH RESOLUTION IMAGING APPARATUS AND METHOD

(71) Applicants: Fluidigm Canada Inc., Markham (CA); Paul Corkum, Markham (CA)

(72) Inventors: Paul Corkum, Ottawa (CA); Alexander V. Loboda, Thornhill (CA)

(73) Assignee: FLUIDIGM CANADA INC., Markham (CA)

(*) Notice: Subject to any disclaimer, the term of this patent is extended or adjusted under 35 U.S.C. 154(b) by 0 days.

(21) Appl. No.: 17/253,538

(22) PCT Filed: Jun. 18, 2019

(86) PCT No.: PCT/US2019/037644
§ 371 (c)(1),
(2) Date: Dec. 17, 2020

(87) PCT Pub. No.: WO2019/246033
PCT Pub. Date: Dec. 26, 2019

(65) Prior Publication Data
US 2021/0118661 A1   Apr. 22, 2021

Related U.S. Application Data

(60) Provisional application No. 62/792,759, filed on Jan. 15, 2019, provisional application No. 62/686,341, filed on Jun. 18, 2018.

(51) Int. Cl.
*H01J 49/04* (2006.01)
*G01N 33/68* (2006.01)
(Continued)

(52) U.S. Cl.
CPC ...... *H01J 49/0463* (2013.01); *G01N 33/6848* (2013.01); *G01N 33/6851* (2013.01);
(Continued)

(58) Field of Classification Search
CPC ............... H01J 49/0463; H01J 49/0004; H01J 49/0031; H01J 49/025; H01J 49/067;
(Continued)

(56) References Cited

U.S. PATENT DOCUMENTS 9,524,856 B2 * 12/2016 Hilliard ............... H01J 49/0463
2003/0111600 A1 * 6/2003 Thomson ............ H01J 49/0463
250/288

(Continued)

FOREIGN PATENT DOCUMENTS

WO   2016090356 A1   6/2016

OTHER PUBLICATIONS

International Application No. PCT/US2019/037644 received an International Search Report and Written Opinion dated Nov. 21, 2019, 15 pages.

*Primary Examiner* — Kiet T Nguyen
(74) *Attorney, Agent, or Firm* — Kilpatrick Townsend & Stockton LLP

(57) ABSTRACT

The present invention relates to the high resolution imaging of samples using imaging mass spectrometry (IMS) and to the imaging of biological samples by imaging mass cytometry (IMC™) in which labelling atoms are detected by IMS. LA-ICP-MS (a form of IMS in which the sample is ablated by a laser, the ablated material is then ionised in an inductively coupled plasma before the ions are detected by mass spectrometry) has been used for analysis of various substances, such as mineral analysis of geological samples, analysis of archaeological samples, and imaging of biological substances. However, traditional LA-ICP-MS systems and methods may not provide high resolution. Described herein are methods and systems for high resolution IMS and IMC.

20 Claims, 17 Drawing Sheets

(51) Int. Cl.
| | |
|---|---|
| *G02B 21/33* | (2006.01) |
| *H01J 37/20* | (2006.01) |
| *H01J 37/28* | (2006.01) |
| *H01J 49/00* | (2006.01) |
| *H01J 49/02* | (2006.01) |
| *H01J 49/06* | (2006.01) |
| *H01J 49/10* | (2006.01) |
| *H01J 49/40* | (2006.01) |
| *H01J 49/16* | (2006.01) |
| *H01J 49/14* | (2006.01) |

(52) U.S. Cl.
CPC ............. *G02B 21/33* (2013.01); *H01J 37/20* (2013.01); *H01J 37/28* (2013.01); *H01J 49/0004* (2013.01); *H01J 49/0031* (2013.01); *H01J 49/025* (2013.01); *H01J 49/0418* (2013.01); *H01J 49/067* (2013.01); *H01J 49/105* (2013.01); *H01J 49/142* (2013.01); *H01J 49/161* (2013.01); *H01J 49/164* (2013.01); *H01J 49/40* (2013.01)

(58) Field of Classification Search
CPC ...... H01J 49/105; H01J 49/40; H01J 49/0418; H01J 49/142; H01J 49/161; H01J 49/164; H01J 37/20; H01J 37/28; G01N 33/6848; G01N 33/6851; G02B 21/33; G02B 21/0032; G02B 21/02; G02B 21/26
USPC .......................................................... 250/288
See application file for complete search history.

(56) References Cited

U.S. PATENT DOCUMENTS

| | | |
|---|---|---|
| 2005/0094293 A1 | 5/2005 | Tanabe et al. |
| 2010/0315705 A1 | 12/2010 | Harada et al. |
| 2017/0023482 A1 | 1/2017 | Cicerone et al. |

* cited by examiner

HIGH RESOLUTION IMAGING APPARATUS AND METHOD

CROSS REFERENCE TO RELATED APPLICATIONS

The present application claims the benefit of U.S. Provisional Application No. 62/686,341 filed Jun. 18, 2018 and entitled "HIGH RESOLUTION IMAGING APPARATUS AND METHOD," and U.S. Provisional Application No. 62/792,759 filed Jan. 15, 2019 and entitled "HIGH RESOLUTION IMAGING APPARATUS AND METHOD," both of which are hereby incorporated by reference in their entireties.

FIELD OF THE INVENTION

The present invention relates to the high resolution imaging of samples using imaging mass spectrometry (IMS) and the imaging of biological samples by imaging mass cytometry (IMC™).

BACKGROUND

LA_ICP-MS (a form of IMS in which the sample is ablated by a laser, the ablated material is then ionised in an inductively coupled plasma before the ions are detected by mass spectrometry) has been used for analysis of various substances, such as mineral analysis of geological samples, analysis of archaeological samples, and imaging of biological substances.

Imaging of biological samples by IMC has previously been reported for imaging at a cellular resolution. Detailed imaging at a sub-cellular resolution has also recently been reported.

Despite these recent advances, there is a need for still further apparatus and techniques that enhance the resolution of IMC to sub micrometer scales. The two main challenges in enhancing the resolution of IMC to sub micrometer scales are:

1) confining the sampling spot area to a size of around 200 nm or less in size; and
2) ensuring that the amount of analyte in the ablated material produces a sufficient signal-to-noise ratio.

It is an object of the invention to provide further and improved apparatus and techniques which overcome these two challenges in order to provide for high resolution imaging of samples.

SUMMARY OF THE INVENTION

In general terms, the analyser apparatus disclosed herein comprises two broadly characterised systems for performing imaging elemental mass spectrometry.

The first is a sampling and ionisation system. This system contains a sample chamber, which is the component in which the sample is placed when it is subjected to analysis. The sample chamber comprises a stage, which holds the sample (typically the sample is on a sample carrier, such as a microscope slide, e.g. a tissue section, a monolayer of cells or individual cells, such as where a cell suspension has been dropped onto the microscope slide, and the slide is placed on the stage). The sampling and ionisation system act to remove material from the sample in the sample chamber (the removed material being called sample material herein) which is converted into ions, either as part of the process that causes the removal of the material from the sample or via a separate ionisation system downstream of the sampling system. To generate elemental ions, hard ionisation techniques are used.

The ionised material is then analysed by the second system which is the detector system. The detector system can take different forms depending upon the particular characteristic of the ionised sample material being determined, for example a mass detector in mass spectrometry-based analyser apparatus.

The present inventions provide improvements over current IMS and IMC apparatus and methods by the application of various apparatus and techniques which exploit advantages in the analysis of tissue sections of a thickness less than 100 nm. When such ultrathin sections are used, the opportunity for further analytical techniques is increased. The inventors have discovered it is possible to use lenses which maintain a particularly high refractive index around the ablation spot (e.g. immersion lenses), which focus the laser used for laser ablation down to a particularly small ablation spot. The inventors have determined that that when ultrathin sections are analysed, such lenses can be used to focus laser radiation without causing damage to areas of the sample outside the area targeted for ablation. This is because the high refractive index of the lens material ensures that the laser is focused into a tight focal spot all the way through the lens down to the ablative spot. This tight focal spot is thus smaller than would be possible without the high refractive index material and because the size of the focal spot determines lateral resolution, the present invention thus provides apparatus and techniques which provide for improved lateral resolution. Furthermore, the focus of the lens is not merely in two dimensions. It is a three dimensional volume of concentrated radiation. Accordingly, the diameter, but also the depth of the ablative spot (i.e. the focal point of the radiation) is of concern. If the focal length is set such that the focus of the radiation is in the substrate rather than at its surface, this can lead to unpredictable breakdown and fragmentation of the sample. This problem is caused in particular by the fact the inventors' finding that to use an immersion lens most effectively, the sample is best ablated in a manner that directs the laser radiation through the sample carrier.

Likewise, the inventors have discovered that when thin sections are used, it is possible to perform electron microscopy on a sample also analysed by IMS or IMC, for example, prior to analysing the sample by IMC. Accordingly, high resolution structural images can be obtained by electron microscopy, for example transmission electron microscopy, and then this high resolution image used to refine, the resolution of image data obtained by IMS or IMC to a resolution beyond that achievable with ablation using laser radiation (due to the much shorter wavelength of electrons compared to photons). Alternatively or in addition, the electron microscopy image may be related to the IMC image of the same region of a sample, for example by relating the localization of protein targets imaged by IMC with subcellular (e.g., nano-scale) structures identified by electron microscopy. As described in more detail below, the electron microscopy imaging may be performed "off line" in a separate apparatus, or the components of the electron microscope may be incorporated into the IMS or IMC apparatus.

Moreover, the inventors have developed further techniques for the high resolution imaging based on a combination of charged particles (e.g. ion or electron) bombardment of a sample coupled with laser ionisation of the sample material, either subsequent to the sputtering of sample material from the sample or at the time of sampling. As charged particles can be focussed more tightly while still achieving removal of material from the sample, again greater resolution can be achieved by this means compared to traditional laser ablation based techniques. Ion optics may be used to direct charged particles toward a sample, and/or direct ionized sample to a mass spectrometer (e.g., a TOF or magnetic sector detector). Ion optics may be similar to those used in electron or ion microscopes. Ion optics may include ion scanning optics (e.g., for scanning charged particles across a sample), ion focusing optics (e.g., for determining an spot size or focusing sample ions toward a detector), and ion accelerating optics (to determine energy of charged particles impinging the sample, or for accelerating ions toward a detector). Ion optics may comprise one or more charged surfaces (e.g., plates) of appropriate shape, charge and/or orientation.

Thus, in operation of one apparatus according to the invention, the sample is taken into the apparatus, is sampled to generate ionised material using a laser system comprising optics in which laser radiation is directed onto the sample though an immersion lens (sampling may generate vaporous/particular material, which is subsequently ionised by the ionisation system), and the ions of the sample material are passed into the detector system.

Thus, in operation of another apparatus according to the invention, the sample is taken into the apparatus, is imaged using by electron microscopy (e.g. transmission electron microscopy), and then is sampled to generate ionised material using a sampling and ionisation system (sampling may generate ions, or may generate non-charged vaporous/particular material (or the non-charged vaporous/particular material may be formed by charges neutralising in any ions formed on sampling), which in the latter case is subsequently ionised by a separate ionisation system), and the ions of the sample material are passed into the detector system.

Finally, in operation of a further apparatus of the invention, the sample is taken into the apparatus, is sampled to generate material using a sputtering based sampling system (a charged particle-based sampling system), where the sample material is ionised by a laser post-ionisation system, either subsequent to the sputtering of sample material from the sample or at the time of sampling, and the ions of the sample material are passed into the detector system.

Although the detector system of the apparatus of the invention can detect many ions, most of these will be ions of the atoms that naturally make up the sample. In some cases, for example when analysing biological samples, the native element composition of the sample may not be suitably informative. This is because, typically, all proteins and nucleic acids are comprised of the same main constituent atoms, and so while it is possible to tell regions which contain protein/nucleic acid from those that do not contain such proteinaceous or nucleic acid material, it is not possible to differentiate a particular protein from all other proteins. However, by labelling the sample with atoms not present in the material being analysed under normal conditions, or at least not present in significant amounts (for example certain transition metal atoms, such as rare earth metals; see section on labelling below for further detail), specific characteristics of the sample can be determined. In common with IHC and FISH, the detectable labels can be attached to specific targets on or in the sample (such as fixed cells or a tissue sample on a slide), inter alia through the use of SBPs such as antibodies, nucleic acids or lectins etc. targeting molecules on or in the sample. In order to detect the ionised label, the detector system is used, as it would be to detect ions from atoms naturally present in the sample. By linking the detected signals to the known positions of the sampling of the sample which gave rise to those signals it is possible to generate an image of the atoms present at each position, both the native elemental composition and any labelling atoms. In aspects where native elemental composition of the sample is depleted prior to detection, the image may only be of labelling atoms. The technique allows the analysis of many labels in parallel (also termed multiplexing), which is a great advantage in the analysis of biological samples, now with increased speed due to the application of a laser scanning system in the apparatus and methods disclosed herein.

Thus the invention provides an apparatus for analysing a biological sample comprising:
 a sample stage;
 a laser source; and
 focusing optics comprising an objective lens, the focusing optics adapted to direct a beam of radiation from the laser source towards a location on the sample stage; and wherein
 the apparatus further comprises an immersion medium positioned between the objective lens and the sample stage.

The invention also provides a method of preparing a biological sample for analysis comprising: staining the sample with a contrast agent for electron microscopy; labelling the sample with labelling atoms.

The invention also provides a method of analysing a biological sample comprising: imaging a sample by electron microscopy;
 directing a beam of radiation emitted by the laser source towards a location on the sample to produce an ablated plume of sample material;
 ionising the ablated plume of sample material; and
 detecting the sample ions from the sample material.

The invention also provides an apparatus for analysing a biological sample comprising: a sample stage;
 a source of charged particles and a charged particle column for passing a beam of charged particles to a location on the sample stage; and
 a first laser source and first focusing optics configured to direct a laser beam emitted by the first laser source towards the sample stage.

The invention also provides a method of analysing a biological sample comprising: passing a beam of charged particles towards a location on the sample to sputter material from the sample; illuminating the sputtered sample material with a pulse of laser radiation to produce a plume of material comprising sample ions; and detecting said sample ions by mass spectrometry.

The invention also provides a method of analysing a biological sample comprising: passing a beam of charged particles towards a location on the sample produces a sample ignition state on the sample; illuminating the sample with a pulse of laser radiation to produce a plume of sample material comprising sample ions from the location; and detecting said sample ions by mass spectrometry.

DESCRIPTION OF THE ACCOMPANYING FIGURES

FIG. 1 is a schematic diagram of the optics of a prior apparatus set up.
FIG. 2 is a schematic diagram of the optics of another prior apparatus set up.
FIG. 3 is a schematic diagram of the optics arrangement of an exemplary embodiment of the invention.

FIG. 12 shows an area of 2100×1087 micrometres at a step size of 250 nm.

DETAILED DESCRIPTION OF THE INVENTION

Figure 1:
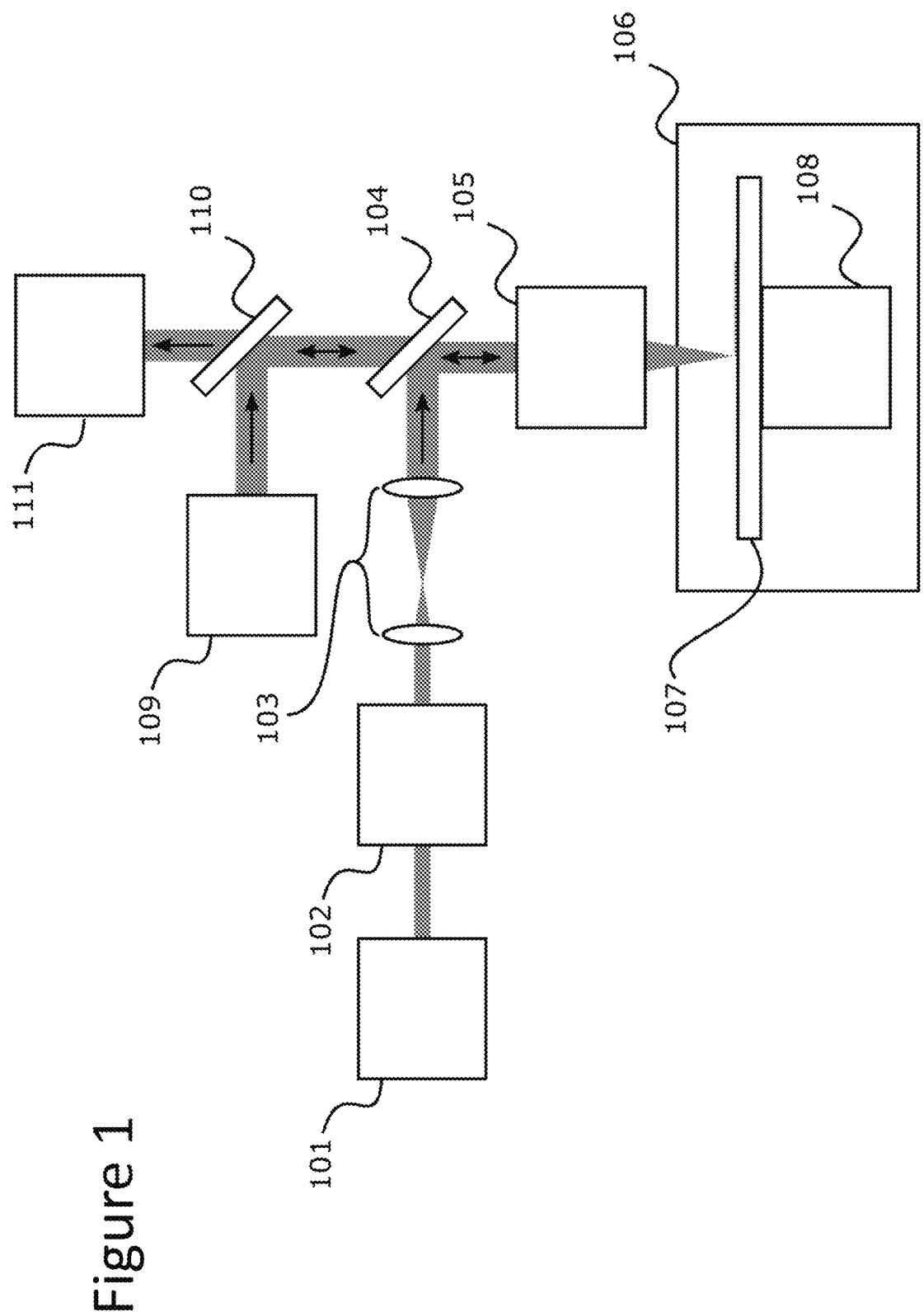

Thus various types of analyser apparatus can be used in practising the disclosure, a number of which are discussed in detail below for instance, apparatus comprising immersion lenses, apparatus comprising an electron microscope (or components thereof), and apparatus for performing secondary neutral mass spectrometry.

Analyser Apparatus Based on Mass-Detection
1. Sampling and Ionisation Systems
a. Laser Ablation Sampling and Ionising System A laser ablation based analyser typically comprises three components. The first is a laser ablation sampling system for the generation of plumes of vaporous and particulate material from the sample for analysis. Before the atoms in the plumes of ablated sample material (including any detectable labelling atoms as discussed below) can be detected by the detector system—a mass spectrometer component (MS component; the third component), the sample must be ionised (and atomised). Accordingly, the apparatus comprises a second component which is an ionisation system that ionises the atoms to form elemental ions to enable their detection by the MS component based on mass/charge ratio (some ionisation of the sample material may occur at the point of ablation, but space charge effects result in the almost immediate neutralisation of the charges). The laser ablation sampling system is connected to the ionisation system by a transfer conduit.

Laser Ablation Sampling System

In brief summary, the components of a laser ablation sampling system include a laser source that emits a beam of laser radiation that is directed upon a sample. The sample is positioned on a stage within a chamber in the laser ablation sampling system (the sample chamber). The stage is usually a translation stage, so that the sample can be moved relative to the beam of laser radiation, whereby different locations on the sample can be sampled for analysis (e.g. locations more remote from one another than can be ablated as a result of the relative movement in the laser beam (the term laser beam can be used interchangeably with the term laser radiation herein) can be induced by laser scanning system described herein). As discussed below in more detail, gas is flowed through the sample chamber, and the flow of gas carries away the plumes of aerosolised material generated when the laser source ablates the sample, for analysis and construction of an image of the sample based on its elemental composition (including labelling atoms such as labelling atoms from elemental tags). As explained further below, in an alternative mode of action, the laser system of the laser ablation sampling system can also be used to desorb material from the sample.

For biological samples (cells, tissues sections etc.) in particular, the sample is often heterogeneous (although heterogeneous samples are known in other fields of application of the disclosure, i.e. samples of a non-biological nature). A heterogeneous sample is a sample containing regions composed of different materials, and so some regions of the sample can ablate at lower threshold fluence at a given wavelength than the others. The factors that affect ablation thresholds are the absorbance coefficient of the material and mechanical strength of material. For biological tissues, the absorbance coefficient will have a dominant effect as it can vary with the laser radiation wavelength by several orders of magnitude. For instance, in a biological sample, when utilising nanosecond laser pulses a region that contains proteinaceous material will absorb more readily in the 200-230 nm wavelength range, while a region containing predominantly DNA will absorb more readily in the 260-280 nm wavelength range.

It is possible to conduct laser ablation at a fluence near the ablation threshold of the sample material. Ablating in this manner often improves aerosol formation which in turn can help improve the quality of the data following analysis. Often to obtain the smallest crater, to maximise the resolution of the resulting image, a Gaussian beam is employed. A cross section across a Gaussian beam records an energy density profile that has a Gaussian distribution. In that case, the fluence of the beam changes with the distance from the centre. As a result, the diameter of the ablation spot size is a function of two parameters: (i) the Gaussian beam waist ($1/e^2$), and (ii) the ratio between the fluence applied and the threshold fluence.

Thus, in order to ensure consistent removal of a reproducible quantity of material with each ablative laser pulse, and thus maximise the quality of the imaging data, it is useful to maintain a consistent ablation diameter which in turn means adjusting the ratio of the energy supplied by the laser pulse to the target to the ablation threshold energy of the material being ablated. This requirement represents a problem when ablating a heterogeneous sample where the threshold ablation energy varies across the sample, such as a biological tissue where the ratio of DNA and protein material varies, or in a geological sample, where it varies with the particular composition of the mineral in the region of the sample. To address this, more than one wavelength of laser radiation can be focused onto the same ablation location on a sample, to more effectively ablate the sample based on the composition of the sample at that location.

Laser System of the Laser Ablation Sampling System

The laser system can be set up to produce single or multiple (i.e. two or more) wavelengths of laser radiation. Typically, the wavelengths of laser radiation discussed refer to the wavelength which has the highest intensity (the "peak" wavelength). If the system produces different wavelengths, they can be used for different purposes, for example, for targeting different materials in a sample (by targeting here is meant that the wavelength chosen is one which is absorbed well by a material).

Where multiple wavelengths are used, at least two of the two or more wavelengths of the laser radiation can be discrete wavelengths. Thus when a first laser source emits a first wavelength of radiation that is discrete from a second wavelength of radiation, it means that no, or a very low level of radiation of the second wavelength is produced by the first laser source in a pulse of the first wavelength, for example, less than 10% of the intensity at the first wavelength, such as less than 5%, less than 4%, less than 3%, less than 2%, or less than 1%. Typically, when different wavelengths of laser radiation are produced by harmonics generation, or other non-linear frequency conversion processes, then when a specific wavelength is referred to herein, it will be understood by the skilled person that there will be some degree of variation about the specified wavelength in the spectrum produced by the laser. For example, a reference to X nm encompasses a laser producing a spectrum in the range X±10 nm, such as X±5 nm, for example X±3 nm.

Focusing Optics and Objective Lenses

As matter of routine arrangement, optical components can be used to direct a beam of laser radiation to a focussed spot. FIG. 1 is a schematic diagram of the optics of a prior apparatus set up. Here a laser source (e.g. a pulsed laser source, optionally incorporating a pulse picker) 101 emits a beam of laser radiation which is directed through an energy control module 102 and then optics 103. The beam of radiation is then directed towards the sample by beam/illumination combining optics 104 through focusing optics and objective lens 105. The sample is on a sample stage 107 in the sample chamber 106. The sample stage 107 (e.g., a glass slide), may be mounted on a three-axis (i.e. x, y, z) translation stage 108 in the sample chamber 106. The setup of FIG. 1 also comprises a camera 111 for viewing the sample using the same focusing optics and objective lens 105. An illumination source 109 emits visible light which is directed to the sample by illumination/inspection splitting optics 110, through the beam/illumination combining optics 104 and the focusing optics 105.

Figure 2:
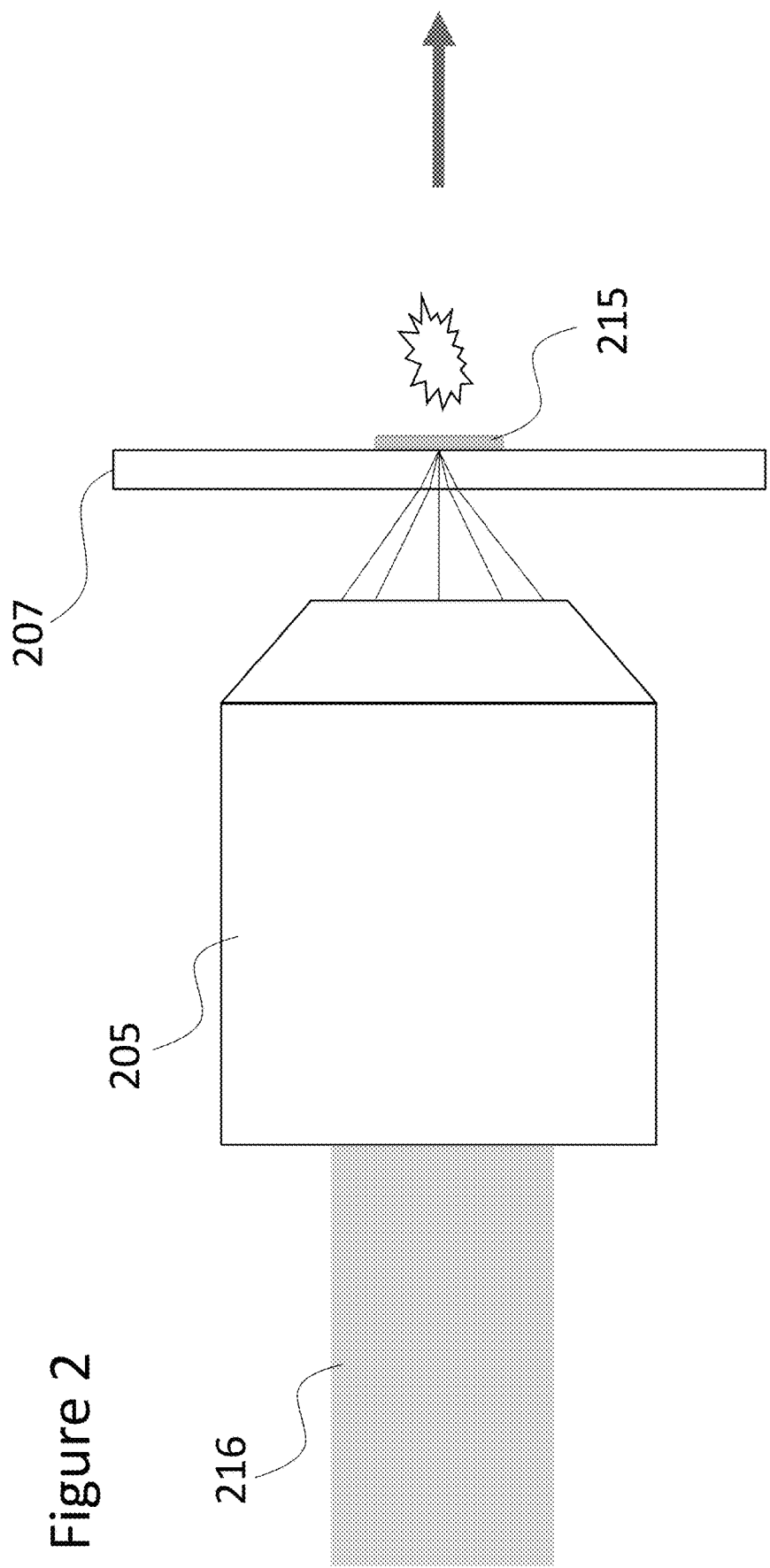

An alternative arrangement of a prior apparatus set up is shown in FIG. 2. Here, a sample 215 is positioned on the opposite side of the sample stage 207 to the objective lens 205 and the laser radiation ablates the sample 215 through the sample stage 207 or through a sample chamber. In some instances, the sample chamber is held under a vacuum, or a partial vacuum. Ray diagram lines are shown to represent the possible path the laser beam 216 takes through from the objective lens 205 through the glass slide 207.

As discussed above, one of the main challenges in achieving a spatial resolution of less than 200 nm, for example less than 150 nm, such as less than 100 nm, in traditional IMC and IMS is confining the spot size of the laser to less than 200 nm (e.g., less than 150 nm or less than 100 nm) in size. The full width at half maximum of the spot size of the laser is defined by $D=0.541\lambda/NA^{0.91}$, for systems where numerical aperture (NA) exceeds 0.7, where is $\lambda$ is the wavelength of the laser light (used interchangeably with laser radiation herein) and NA is the numerical aperture of the objective lens 105, 205 of the focusing optics. Therefore, in traditional IMC and IMS, lasers of a shorter wavelength such as deep UV lasers of wavelength 213 nm, or focusing optics with an NA above 0.7, e.g. above 0.8, such as high NA (above 0.9), are used to reduce the size of the laser spot size and hence improve resolution.

However, the numerical aperture of a lens is expressed as $NA=n\times\sin\theta$, where n is the refractive index of the medium between the lens and the sample stage 107, 207 and $\theta$ is half the acceptance angle of the objective. Therefore, maximum theoretical numerical aperture of the objective lens in typical IMC and IMS (such as the objective lens 105, 205 of the prior apparatus set up shown in FIGS. 1 and 2) is limited to 1.0 because the refractive index of a vacuum is 1.0 and the refractive index of air is around 1.0.

Immersion Lenses

The present invention overcomes the limitations of traditional IMC and IMS by utilising an immersion medium. The immersion medium has a refractive index which is greater than 1.0 and is placed between the objective lens and the sample stage. In this way, the apparatus of the present invention achieves numerical apertures of greater than 1.0 and so the spot size of the laser is less than 200 nm, less than 150 nm, or less than 100 nm. Thus, the present invention provides an apparatus for imaging mass cytometry with spatial resolution of 200 nm or better, 150 nm or better, or 100 nm or better.

Accordingly, the invention provides a laser sampling system comprising:
  a sample stage;
  a laser source; and
  focusing optics comprising an objective lens, the focusing optics adapted to direct radiation from the laser source towards a location on the sample stage; and wherein
  the laser sampling system further comprises an immersion medium positioned between the objective lens and the sample stage.

Accordingly, the invention provides an apparatus for analysing a biological sample comprising:
  a sample stage;
  a laser source; and
  focusing optics comprising an objective lens, the focusing optics adapted to direct radiation from the laser source towards a location on the sample stage; and wherein
  the apparatus further comprises an immersion medium positioned between the objective lens and the sample stage.

Typically, the apparatus also includes a mass spectrometry based detector.

Accordingly in operation, the sample stage holds the sample, typically wherein the sample is on a sample carrier and the same stage holds the sample carrier. Laser radiation is then directed through the optics of the apparatus, through the objective lens and immersion medium to the sample, where the radiation ablates material from the sample.

In order to achieve the optimal focusing conditions for the laser, the immersion medium of the present invention has a refractive index of greater than 1.00, such as 1.33 or greater, 1.50 or greater, 2.00 or greater, or 2.50 or greater.

Furthermore, in order to reconstruct the image of a single layer of the thickness (or less than the thickness) of a biological cell or to read a thicker specimen layer by layer and generate a 3D image, as discussed further herein, the sample preferably has a thickness of 100 micrometers or below, such as 10 micrometers or below, 5 micrometers or below, 2 micrometers or below, or 100 nm or below, or 50 nm or below, or 30 nm or below. In some embodiments described in more detail herein, the combination of the objective lens and the immersion medium is referred to as an immersion lens.

Apparatus or sampling systems as described above comprising an immersion medium in some embodiments comprise a medium or high NA objective lens, such as an NA of 0.7 or more, 0.8 or more, or 0.9 or more. Such systems typically also comprise a mass detector, such as a TOF mass spectrometry detector.

Liquid Immersion Medium

Figure 3:
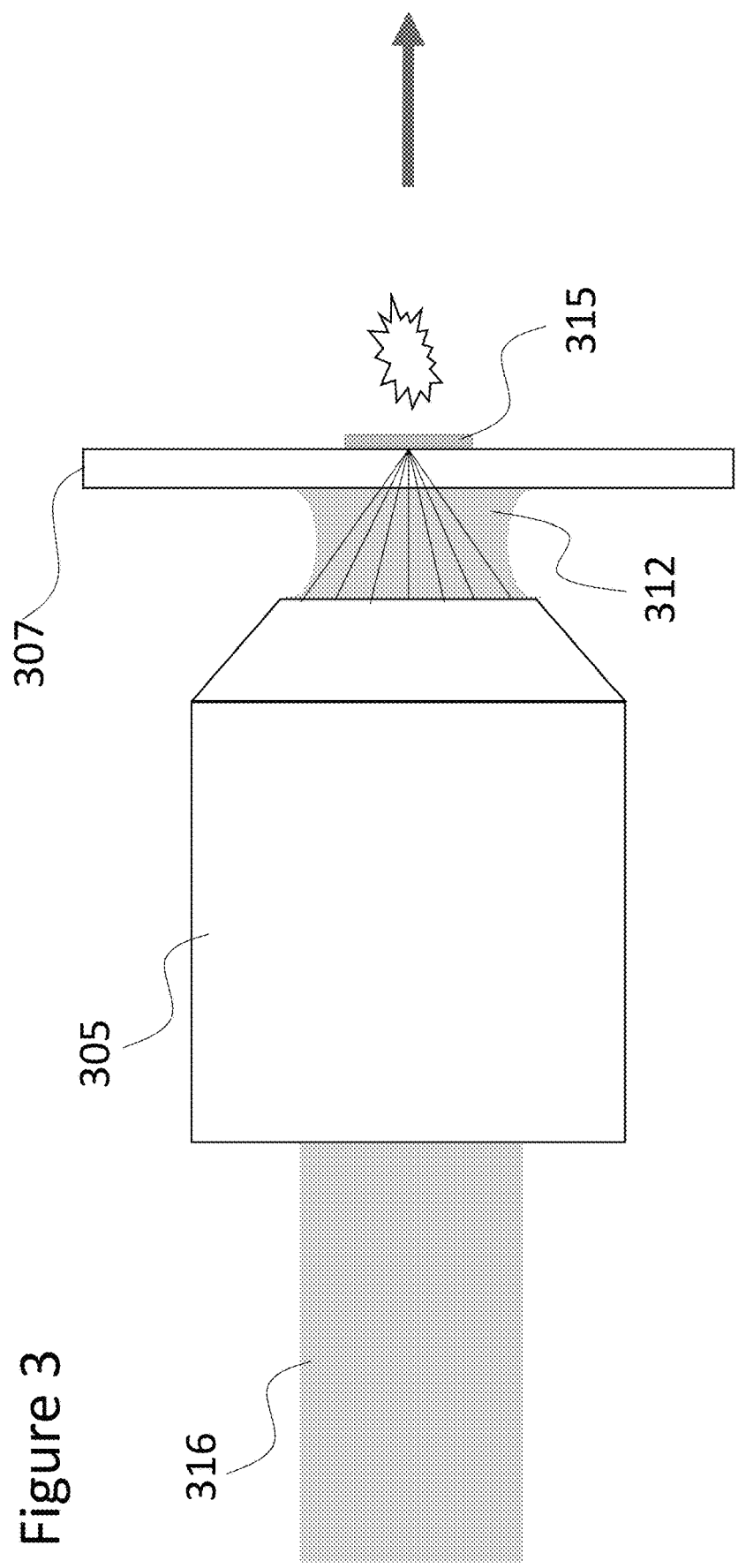

In some embodiments of the invention, the immersion medium is a liquid immersion medium, FIG. 3 is a schematic diagram of the optics arrangement of an exemplary embodiment of the invention. It contains elements in common with the set ups shown in FIGS. 1 and 2. The focusing optics comprising an objective lens 305 directs a beam of radiation 316 from a laser source (source not shown) towards a location on the sample stage 307 and a liquid immersion medium 312 is positioned between the objective lens 305 and the sample stage 307. Here, a biological sample 315 is positioned on the opposite side of the sample stage 307 to the liquid immersion medium 312. Ray diagrams show how the liquid immersion medium 312 provides tighter focusing conditions than the conventional set up shown in FIG. 2. Suitable liquids for liquid immersion media are water which has a refractive index, n, of 1.333, glycerin (n=1.4695), an oil such as paraffin oil (n=1.480), cedarwood oil (n=1.515) and synthetic oil (n=1.515), or anisole (n=1.5178), bromonaphthalene (n=1.6585) and methylene iodide (n=1.740). Commercial immersion oils are also available and some of these commercial oils have properties which are particularly advantageous for application in the present invention. For example, low or non-fluorescing immersion oils such as Olympus Low Auto Fluorescence Immersion Oil and Nikon are particularly useful for use with short wavelength lasers because they provide improved signal to noise ratio over general all-purpose immersion oils. Other oils have very high viscosity, such as Cargille labs type NVH and OVH, which is of use when the distance between the objective lens 305 and sample stage 307 is large.

Commercial oil-immersion objectives can achieve a maximum numerical aperture of around 1.49 (close to the refractive index of the immersion oil), and are able to focus a 515 nm laser beam to a FWHM focal spot diameter of around 160 nm.

When a liquid immersion medium is used, the sample needs to be positioned on the opposite side of the sample carrier to the liquid medium (as illustrated in FIG. 3) so that a carrier gas can collect the ablated material. Accordingly, through-sample carrier ablation techniques must be applied here. This has the additional benefit of a smaller achievable working distance for the ablation material collection hardware, and no need to bend the transport conduit between the sample chamber and the detector. This also leads to reductions in the transient time, thus increasing the achievable ablation rate in spots per second.

Liquid immersion lenses (e.g. objective-in-water or objective-in-oil lenses) are commercially available from Olympus, ThorLabs and Leica.

Solid Immersion Medium

Figure 4:
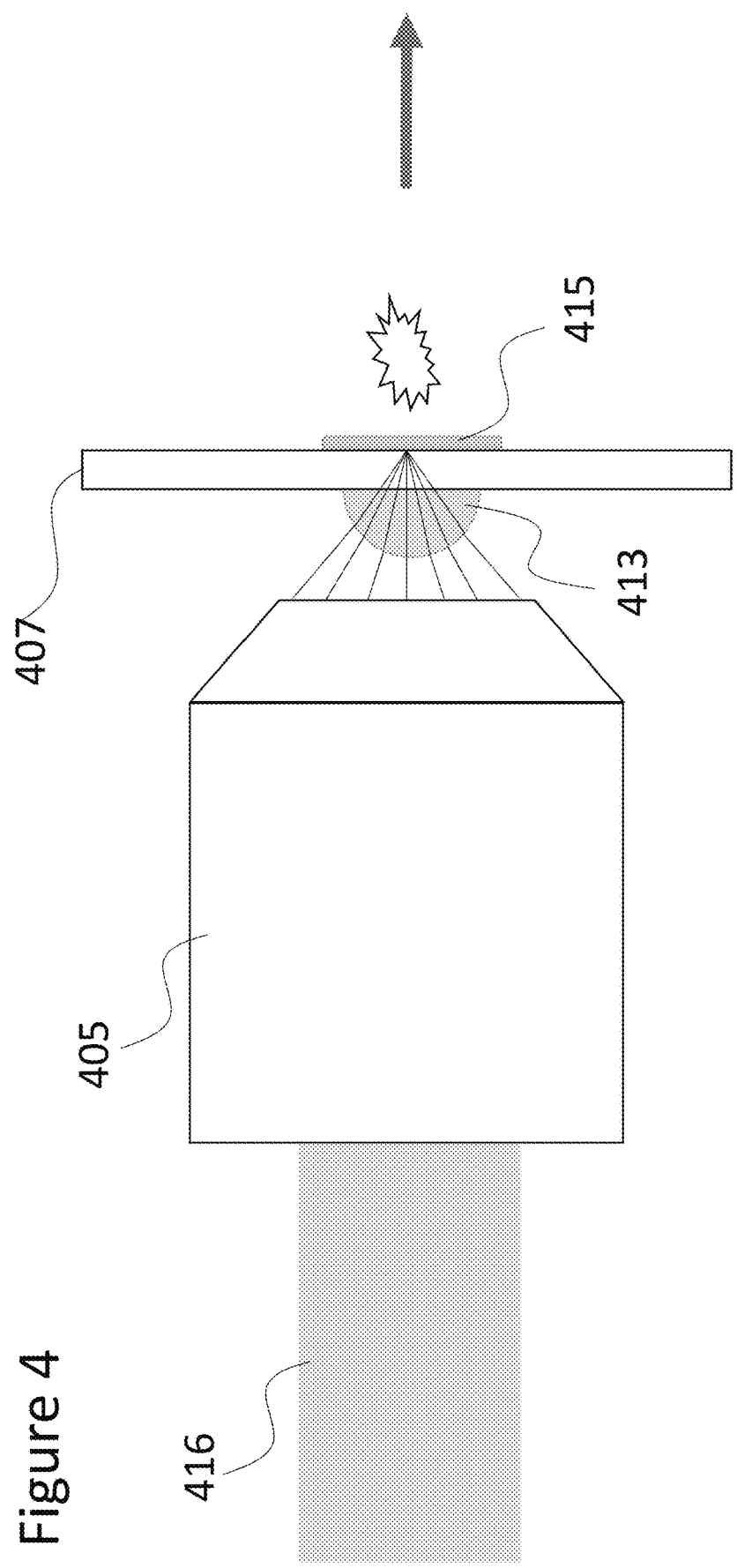
FIG. 4 is a schematic diagram of the optics arrangement of a further exemplary embodiment of the invention.

In some embodiments of the invention, the invention provides an apparatus wherein the immersion medium is a solid immersion medium. FIG. 4 is a schematic diagram of the optics arrangement of further exemplary embodiment of the invention in which a solid immersion 413 is positioned between the objective lens 405 and the sample stage 407. The other components of FIG. 4 correspond to those in FIG. 3.

Similarly to liquid immersion media, the refractive index n of the solid immersion lens is greater than air. Suitable materials for solid immersion lenses are glass, such as S-LAH79™ glass type, which has a refractive index of 2.0 when operating with a wavelength of ~520 nm. Alternative suitable materials for the solid immersion medium of the present invention are diamond or fused silica. At 266 nm diamond becomes well suited for optical applications, since it has a refractive index of >2.5 in UV it offers an opportunity to focus 266 nm light to the spot size on the scale of 100 nm or even below that. Fused silica may be more attractive from a cost perspective. It would be practical both as a specimen substrate and as a solid immersion lens material. Though, the index of refraction of fused silica in UV is only ~1.5 and the spot size will be proportionally larger due to that.

There are two standard optical schemes for solid immersion media: the hemispherical immersion lens and the Weierstrass immersion lens.

Figure 5:
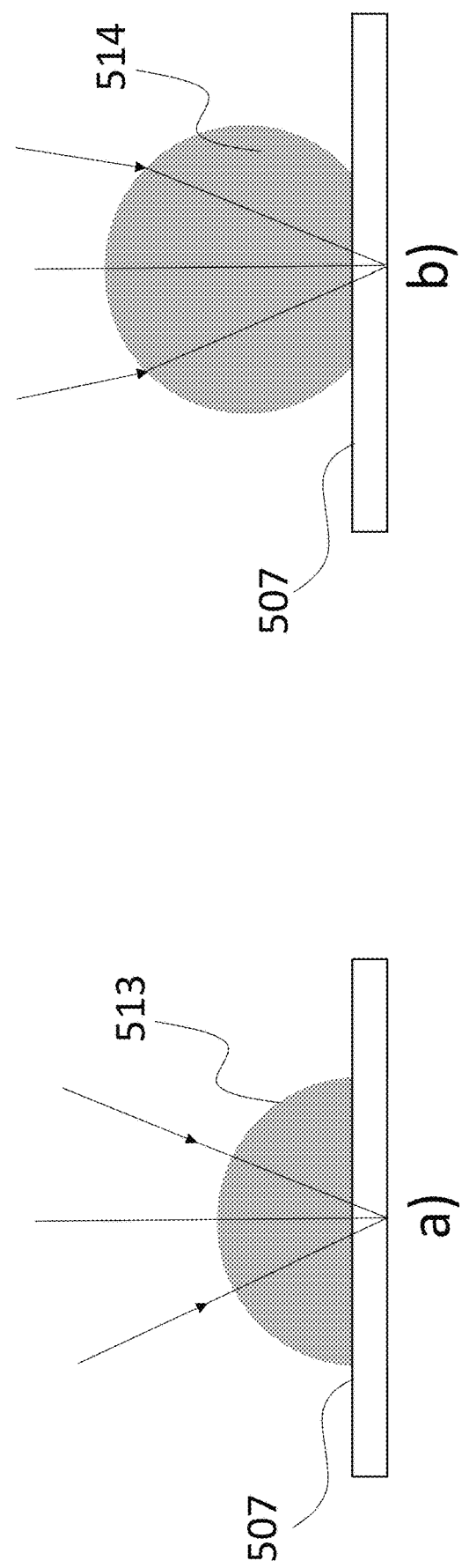
FIG. 5a is a schematic diagram of the optics arrangement of another exemplary embodiment of the invention, illustrating the path of the laser beam through a hemispherical solid immersion lens.
FIG. 5b is a schematic diagram of the optics arrangement of another exemplary embodiment of the invention, illustrating the path of the laser beam through a Weierstrass solid immersion lens.

Hemispherical Solid Immersion Lens:

FIG. 5a) shows the geometry of a hemispherical solid immersion lens. The hemispherical solid immersion lens is capable of increasing the numerical aperture of an optical system by the refractive index, n, of the material of the lens.

Weierstrass Solid Immersion Lens:

FIG. 5b) shows the geometry of a Weierstrass solid immersion lens. The Weierstrass solid immersion lens is a truncated sphere and has a height from the glass slide 507 of $(1+1/n)r$, where r is the radius of the spherical surface of the lens. The Weierstrass lens is capable of increasing the numerical aperture of an optical system by $n^2$, hence the Weierstrass lens is capable of further increasing the numerical aperture of an optical system than the hemispherical lens.

Accordingly, the present invention provides an apparatus wherein the solid immersion medium is a hemispherical solid immersion lens or a Weierstrass solid immersion lens. As shown in FIGS. 3 and 4, when a biological sample 315, 415 is mounted on the sample stage 307, 407, the biological sample can be mounted on the opposite side of the sample stage to the solid immersion material. The stage on which the sample is mounted can be made of material of the same refractive index as the solid immersion lens and the solid immersion lens can be made thinner by an amount equal to the thickness of the substrate to maintain the focal spot location.

Combination of Immersion Lenses and Biological Samples

The present invention comprising an immersion medium positioned between the objective lens and the sample stage provide further advantages when used to analyse a biological sample prepared according to other methods of the invention described herein (page 112). In particular, the present invention provides further advantages when the biological sample has a thickness of 100 micrometers or below, such as 10 micrometers or below, or 100 nm or below, or 50 nm or below, or 30 nm or below.

For example, the apparatus of the present invention comprising an immersion medium between the objective lens and the sample stage can be used to analyse a biological sample of thickness of 100 nm or below, such as 50 nm or below, or 30 nm or below. Since the apparatus of the present invention provides an apparatus for imaging mass cytometry with spatial resolution of 200 nm or better (preferably 100 nm or less), the spot size of the laser is 200 nm or less (preferably 100 nm or less) and so the ablation depth is typically 200 nm or less (preferably 100 nm or less). Therefore, analysing a biological sample of thickness 200 nm or below using the present invention will ablate all the way through the sample (or preferably 100 nm or less, when the laser spot size is 100 nm or less). Thus, the present invention provides the possibility to reconstruct the image of a single layer of the thickness of a biological cell by utilising the apparatus with sequential sections of a biological cell.

Alternatively, the apparatus of the present invention comprising an immersion medium between the objective lens and the sample stage can be used to analyse a biological sample of 100 micrometers or below, such as 10 micrometers or below, 5 micrometers or below, 2 micrometers or below. Sharp focusing of the laser beam by the immersion media as discussed above creates a very short depth of focus. Hence, the present invention provides the opportunity to read a thicker specimen layer by layer and generate a 3D image. The skilled person will appreciate that this analysis of a thicker specimen will be more straightforward the more homogenous a sample is. In tissue samples, which are not homogenous, distortions in in the laser light which arise as the laser travels through the tissue and may result in a larger spot size at the focus than expected.

Accordingly, the invention provides an imaging mass cytometer or imaging mass spectrometer comprising a biological sample, wherein the biological sample has a thickness of less than 100 nm, such as less than 50 nm, or less than 30 nm. The invention also provides an imaging mass cytometer or imaging mass spectrometer comprising a biological sample, wherein the biological sample has a thickness of less than 100 nm, such as less than 50 nm, or less than 30 nm, and wherein the imaging mass cytometer or imaging mass spectrometer comprises a solid immersion lens. The invention also provides an imaging mass cytometer or imaging mass spectrometer comprising a biological sample, wherein the biological sample has a thickness of less than 100 nm, such as less than 50 nm, or less than 30 nm, and wherein the imaging mass cytometer or imaging mass spectrometer comprises a solid immersion lens.

Alternatives to Immersion Lenses in Combination with Thin Biological Samples:

As discussed above, in traditional IMC and IMS, lasers of a short wavelength such as deep UV lasers of wavelength 213 nm, or focusing optics with a n NA above 0.6, e.g. above 0.7, e.g. above 0.8, such as high NA (above 0.9) are used to reduce the size of the laser spot size and hence improve resolution to 100 nm.

The high NA objective may be a refractive optical component and/or a reflective optical component. For example, the use of an aspherical mirror can be used allow the reflecting objective to have a numerical aperture of up to 0.99 (Inagawa et al. Scientific Reports 5, 12833 (2015). A catadioptric mirror system may also be used. Furthermore, it is possible to provide a short wavelength laser (300 nm or below) by using lasers of wavelength 266 nm, or 213 nm, 193 nm solid state lasers, or sixth harmonic generation from ND:Yag, ArF, $F_2$ laser, extreme UV light such as 13.5 nm and 7 nm wavelength ($CO_2$ laser+Sn plasma).

Accordingly, the present invention provides an apparatus for analysing a biological sample comprising:
 a sample stage comprising a first face and a second face, the first and second faces being opposed, and wherein the first face is adapted to receive a biological sample; and
 a laser source; and
 focusing optics comprising an objective lens, the focusing optics adapted to direct a beam of radiation from the laser source towards the second face to a location on the sample stage; and wherein
 the objective lens has a numerical aperture of at least 0.7, at least 0.8, or at least 0.9, such as at least 0.9.

Accordingly, the present invention provides an apparatus for analysing a biological sample comprising:
 a sample stage comprising a first face and a second face, the first and second faces being opposed, and wherein the first face is adapted to receive a biological sample; and
 a laser source; and
 focusing optics comprising an objective lens, the focusing optics adapted to direct a beam of radiation from the laser source towards the second face to a location on the sample stage; and wherein
 the laser source has a wavelength of 300 nm or below.

Accordingly, the present invention provides an apparatus for analysing a biological sample comprising:
 a sample stage comprising a first face and a second face, the first and second faces being opposed, and wherein the first face is adapted to receive a biological sample; and
 a laser source, wherein the laser source has a wavelength of 300 nm or below; and
 focusing optics comprising an objective lens, the focusing optics adapted to direct a beam of radiation from the laser source towards the second face to a location on the sample stage; and wherein
 the objective lens has a numerical aperture of at least 0.7, at least 0.8, or at least 0.9, such as at least 0.9.

As described further herein, ablated material may be ionized or re-ionized close to the surface of the sample, for example by laser ionization of an ablation plume that has expanded past the point of significant charge neutralization (once ionized/re-ionized). In such systems and methods, gas fluidics may not be needed as the plume need not be delivered to ICP for ionization. Instead, ion optics positioned near the sample may direct ionized labelling atoms directly to a mass spectrometer (e.g., a TOF or magnetic sector mass spectrometer). As described herein, in certain cases, a small ablation spot size may reduce neutralizaiton and space charge effects for the ions generated during ablation, making it easier to both ionize and to direct ions to a mass spectrometer. No second pulse for re-ionization is needed in such case. The sample stage and immediately surrounding optics (e.g., high NA lens and/or immersion medium) may be operated in a vacuum, or at low pressure (e.g., to reduce charge through collision) as described further herein.

As the skilled person will appreciate, an apparatus may include a focusing optics with objective lens of numeral aperture of at least 0.9 and/or a laser source with a wavelength of 300 nm or below. Furthermore, while the high numerical aperture or short wavelength can be used as an alternative to or in addition to the immersion lenses as described herein, the other components of the system remain the same as for the immersion lens systems.

Scanning System

In certain aspects, ablation of the sample may be performed by a scanning system. A source of radiation, such as a laser beam or a charged particle beam (such as ion beam or electron beam) source may be scanned across a portion of the sample to produce a single transient (e.g., single instance of ablated material). The transient may be an ablation plume delivered to ICP for atomization and ionization prior to detection by MS. Alternatively, the transient may be ionized by laser radiation at or close to the surface of the sample, as described herein. Scanning with an ion beam or electron beam (e.g., using ion optics) may allow for ablation of a small region of interest of the sample at high resolution (such as a single organelle). For example, the region of interest may have an area of less than 100,000 nm$^2$, less than 50,000 nm$^2$, or less than 20,000 nm$^2$, or less than 10,000 nm$^2$. Alternatively, the region of interest could be larger, such as a single cell or even a group of cells.

In certain embodiments, a laser scanning system directs laser radiation onto the sample to be ablated. As the laser scanner is capable of redirecting the position of laser focus on the sample much more quickly than moving the sample stage relative to a stationary laser beam (due to much lower or no inertia in the operative components of the scanning system), it enables ablation of discrete spots on the sample to be performed more quickly. This quicker speed can enable a significantly greater area to be ablated and recorded as a single pixel, or the speed of the laser spot movement can simply translate to, e.g., an increase in pixel acquisition rate, or a combination of both. In addition, the rapid change in the location of the spot onto which a pulse of laser radiation can be directed permits the ablation of arbitrary patterns, for instance so that a whole cell of non-uniform shape is ablated, by a burst of pulses/shots of laser radiation in rapid succession directed onto locations on the sample by the laser scanner system, and then ionised and detected as a single cloud of material, thus enabling single cell analysis (see the "Sample chamber of the laser ablation sampling system" section at page 33 onwards). A similar rapid-burst technique can also be deployed in methods using desorption to remove sample material from a sample carrier, i.e. cell LIFTing (Laser Induced Forward Transfer).

Accordingly, the invention provides an apparatus for analysing a sample, such as a biological sample, comprising:
(i) sampling and ionisation system to remove material from the sample and to ionise said material to form elemental ions, comprising a laser scanning system and a sample stage;
(ii) a detector to receive elemental ions from said sampling and ionisation system and to detect said elemental ions.

Equally, this combination of features may be combined, as understood as appropriate by the skilled person with any of the other embodiments described herein. The use of a scanning system to increase the acquisition rate provides numerous advantages over other strategies for increasing the rate at which a sample is imaged. For instance, an area of 100 μm×100 μm can be ablated in with a single laser pulse using appropriately adapted apparatus. However, such ablation results in numerous problems. Ablating a large area of a sample at once with a single laser pulse leads to the ablated material being broken up into large chunks initially flying at velocities near the speed of sound, rather than small particles, and rather than the material being transported away quickly from the sample in the flow of carrier gas (described in more detail below), the large chunks may take longer to be entrained (lengthening the washout time of the sample chamber) than the smaller chunks, fail to be entrained, or just fly randomly off the sample or onto another part of the sample. If the large chunk of material flies off the sample, any information in that chunk of material in the form of detectable atoms, such as labelling atoms, is lost. If the chunk of material lands on another part of the sample, information is lost from the ablated area, and moreover any detectable atoms in the chunk of material now lie on and can interfere with the signal that would be acquired from another part of the sample. As differences in the biological material in an ablated spot (e.g. cartilaginous material versus muscle) can also affect how the product breaks up, larger ablation spots sizes can also compound fractionation of the sample, with some kinds of material being entrained in the flow of gas to a lesser degree than others. Furthermore, as described here, in many applications a small spot size is preferred, of the order of pm rather than 100s of μm, and switching between laser spot sizes multiple orders of magnitude different (e.g. 100 μm vs 1 μm) also presents technical challenges. For instance, a laser that can ablate with a spot size of 1 μm may not have the energy to ablate an area with a spot size of 100 μm in a single laser pulse, and sophisticated optics are required to facilitate the transition between 1 μm and 100 μm without significant loss of energy in the laser beam or loss of sharpness of the ablation spot.

Rather than ablating a 100 μm$^2$ single spot, therefore, 100×100 (i.e. 10,000) 1 μm diameter spots can be used to ablate the area by rastering across the area. A smaller spot size for ablation naturally does not suffer from the problems described above to such a great extent—the particles generated by a smaller ablation spot by necessity are themselves much smaller in size. Furthermore, with smaller spots, the resulting smaller particles resulting from the ablation have shorter and more defined washout times from the sample chamber. Where each of the smaller spots is desired to be resolved separately, this in turn has the consequence that data can be acquired more quickly as the transients from each ablative laser pulse do not overlap when detected in the detector (or overlap to an acceptable degree, as explained below).

However, moving a sample stage in 1 μm increments along a row, and then down a row is relatively slow due to inertia as noted above. Thus, by using a laser scanner system to raster across the area, without moving the sample stage, or moving the sample stage less frequently or at a constant speed, the relatively slow speed of the sample stage does not limit the rate at which the sample can be ablated.

Accordingly, to enable rapid scanning, the laser scanning system must be able to rapidly switch the position at which the laser radiation is being directed on the sample. The time taken to switch the ablating position of the laser radiation is termed the response time of the laser scanning system. Accordingly, in some embodiments of the invention, the response time of the laser sampling system is quicker than 1 ms, quicker than 500 μs, quicker than 250 μs, quicker than 100 μs, quicker than 50 μs, quicker than 10 μs, quicker than 5 μs, quicker than 1 μs, quicker than 500 ns, quicker than 250 ns, quicker than 100 ns, quicker than 50 ns, quicker than 10 ns, or around 1 ns.

The laser scanning system can direct the laser beam in at least one direction relative to the sample stage on which the sample is positioned during ablation. In some instances, the laser scanning system can direct the laser radiation in two directions relative to the sample stage. By way of example, the sample stage may be used to move the sample incrementally in the X-axis, and the laser may be swept across the sample in the Y axis (see FIGS. 7-9 for illustrations of the relative movements). When a 1 μm spot size is used, the movement in the X axis may be in 1 μm increments. At a given position in the X axis, the laser scanning system can be used to direct the laser to a series of positions 1 μm apart in the Y axis. Because the rate at which the laser scanning system can direct the laser radiation to different positions in the Y axis is much quicker than the stage can move incrementally in the X axis, a significant increase in ablation rate is achieved in this simple illustration of the operation of the scanner.

In some instances, the laser scanning system directs the laser beam in both the X and Y axes. Accordingly, in this instance more advanced ablation patterns can be generated. For instance, when the laser scanning system can direct the laser radiation in both the X and Y axes, the sample stage may be moved at constant speed in the X axis (thereby eliminating inefficiencies associated with the inertia of the sample stage during the movement across each row other than acceleration/deceleration at the start/end of the row), while the laser scanning system directs laser radiation pulses up and down columns on the sample whilst compensating for the movement of the sample stage. To achieve this movement, the triangle-wave control signals can be applied to the scanner in the X direction, and a sawtooth signal in the Y direction. Alternatively, it may be desirable to apply a sawtooth drive signal to the scanner in the Y direction, depending on the processing algorithm used, as would be appreciated by the skilled person. As a further alternative, one of the scanner components may be pre-rotated slightly, to pre-compensate for the slanted scanning pattern. In some embodiments, the controller of the laser scanning system will cause the laser scanner system to move the beam in a figure-of-eight pattern as the sample stage moves.

The significantly quicker (re-)direction of laser radiation onto different locations on the sample accordingly enables much quicker ablation of large areas of the sample, provided that the laser used in the laser sampling system has a sufficiently high repetition rate (as discussed below). For instance, if only fewer than 5 pulses can be directed to different locations on a sample per second, the time taken to study a 1 mm×1 mm area with ablation at a spot size of 1 μm would be over two days. With a rate of 200 Hz, this would be around 80 minutes, with further reductions in the analysis time for further increases in the frequency of pulses. However, samples are often significantly larger. An average microscope slide on which a tissue section can be placed is 25×75 mm. This would take around 110 days to ablate at a rate of 200 Hz. However, if a laser scanning system is used the time can be dramatically shortened, for instance where the sample stage is moved at a constant speed along the X axis (1 mm/s), while the laser beam is moved back-and-forth in the Y axis direction with the laser scanning system. The laser scanning system can scan the position of the laser focus at a rate that matches the speed of the stage motion, in this case, 500 Hz. This would produce a 1 μm spacing between adjacent lines in the raster pattern at this speed. Then, depending on the maximum laser repetition rate, the extent of the deflection of the laser radiation by the laser scanning system is chosen to match. Here, to produce a peak-to-peak amplitude of 100 microns, a 100 kHz laser repetition rate would be required. This allows the device to process 0.1 mm$^2$/s, compared to at most 0.0004 mm$^2$/s for current apparatus. In comparison to the figure of 110 days discussed above, with a laser scanning system as discussed in this paragraph, it would only take around 5 hours to process the slide.

Another application is arbitrary ablation area shaping. If a high repetition rate laser is used, it is possible to deliver a burst of closely-spaced laser pulses in the same time that a nanosecond laser would deliver one pulse. By quickly adjusting the X and Y positions of the ablation spot during a burst of laser pulses, ablation craters of arbitrary shape and size (down to the diffraction limit of the light) can be created. For instance, the n and n+1 positions in a burst may be no more than a distance equal to 10× the laser spot diameter apart (based on the centre of the ablation spot of the nth spot and the (n+1)th spot), such as less than 8×, less than 5×, less than 2.5 times, less than 2× times, less than 1.5×, around 1×, or less than 1× the diameter of the spot size. Particular methods employing this technique are discussed in the methods section below, at page 32.

Accordingly, in some embodiments, the laser scanning system comprises a positioner to impart a first relative movement of a laser beam emitted by the laser with respect to the sample stage (e.g. the Y axis relative to the surface of the sample).

In some embodiments, the positioner of the laser scanning system is capable of imparting a second relative movement of the laser beam with respect to the sample stage, wherein the first and second relative movements are not parallel, such as wherein the relative movements are orthogonal (e.g. the first movement direction is in the Y axis relative to the surface of the sample and the second movement direction is in the X axis relative to the surface of the sample).

In some embodiments, the laser scanning system further comprises a second positioner capable of imparting a second relative movement of the laser beam with respect to the sample stage, wherein the first and second relative movements are not parallel, such as wherein the relative movements are orthogonal (e.g. the first movement direction is in the Y axis relative to the surface of the sample and the second movement direction is in the X axis relative to the surface of the sample).

Any component which can rapidly direct laser radiation to different locations on the sample can be used as a positioner in the laser scanning system. The various types of positioner discussed below are commercially available, and can be selected by the skilled person as appropriate for the particular application for which an apparatus is to be used, as each has inherent strengths and limitations. In some embodiments of the invention, as set out below, multiple of the positioners discussed below can be combined in a single laser scanning system. Positioners can be grouped generally into those that rely on moving components to introduce relative movements into the laser beam (examples of which include galvanometer mirror, piezoelectric mirror, MEMS mirror, polygon scanner etc.) and those that do not (examples of which include such acousto-optic devices and electro-optic devices). The types of positioners listed in the previous sentence act to controllably deflect the beam of laser radiation to various angles, which results in a translation of the ablation spot. The laser scanning system may comprise a single positioner, or may comprise a positioner and a second positioner. The description of "positioner" and "second positioner" where two positioners are present in the laser scanning system does not define an order in which a pulse of laser radiation hits the positioners on its path from the laser source to the sample.

Galvanometer motors on the shaft of which a mirror is mounted can be used to deflect the laser radiation onto different locations on the sample. Movement can be achieved by using a stationary magnet and a moving coil, or a stationary coil and a moving magnet. The arrangement of a stationary coil and moving magnet produces quicker response times. Typically sensors are present in the motor to sense the position of the shaft and the mirror, thereby providing feedback to the controller of the motor. One galvanometer mirror can direct the laser beam within one axis, and accordingly pairs of galvanometer mirrors are used to enable direction of the beam in both X and Y axes using this technology.

One strength of the galvanometer mirror is that it enables large angles of deflection (much greater than, for example, solid state deflectors), which as a consequence can allow more infrequent movement of the sample stage. However, as the moving components of the motor and the mirror have a mass, they will suffer from inertia and so time for acceleration of the components must be accommodated within the sampling method. Typically, non-resonant galvanometer mirrors are used. As will be appreciated by the skilled person, resonant galvanometer mirrors can be used, but an apparatus using only such resonant components as positioners of the laser scanning system will not be capable of arbitrary (also known as random access) scanning patterns. As it is based on a mirror, a galvanometer mirror deflector can degrade laser radiation beam quality and increase the ablation spot size, and so will again be understood by the skilled person to be most applicable in situations which tolerate such effects on the beam.

Galvanometer-mirror based apparatus can be prone to errors in their positioning, through sensor noise or tracking error. Accordingly, in some embodiments, each mirror is associated with a positional sensor, which sensor feeds back on the mirror's position to the galvanometer to refine the position of the mirror. In some instances, the positional information is relayed to another component, such as an AOD or EOD in series to the galvanometer-mirror, which corrects for mirror positioning error.

Galvanometer mirror systems and components are commercially available from various manufacturers such as Thorlabs (NJ, USA), Laser2000 (UK), ScanLab (Germany), and Cambridge Technology (MA, USA).

In embodiments comprising only galvanometer mirror based positioners, the rate at which ablative laser pulses are capable of being directed at the sample may be between 200 Hz-1 MHz, 200 Hz-100 kHz, 200 Hz-50 kHz, 200 Hz-10 kHz, 1 kHz-1 MHz, 5 kHz-1 MHz, 10 kHz-1 MHz, 50 kHz-1 MHz, 100 kHz-1 MHz, 1 kHz to 100 kHz or 10 kHz-100 kHz.

Accordingly, in some embodiments of the invention, the laser scanner system comprises one or more positioners which is a galvanometer mirror, such as a galvanometer mirror array.

FIG. 1 is a schematic diagram of the optics of a prior apparatus set up. Here a laser source (e.g. a pulsed laser source, optionally incorporating a pulse picker) 101 emits a beam of laser radiation which is directed through an energy control module 102 and then optics 103. The optics 103 may include beam shaping optics. The beam of radiation is then directed towards the sample by beam/illumination combining optics 104 through focusing optics and object lens 105. The sample may be on a support, such as a glass side 107, sitting on a three-axis (i.e. x, y, z) translation stage 108 in the sample chamber 106. The setup of FIG. 1 also comprises a camera 111 for viewing the sample using the same focusing optics and objective lens 105. An illumination source 109 emits visible light which is directed to the sample by illumination/inspection splitting optics 110, through the beam/illumination combining optics 104 and the focusing optics 105.

In a more advanced configuration, the optics (e.g., optics 103) may further include a positioner (e.g., a movable mirror or scanner as described herein) to enable scanning of the laser across a sample. For example, before the beam of laser radiation is shaped by the beam shaping optics of the optics 203, a positioner, such as a galvanometer mirror, piezoelectric mirror, MEMS mirror or polygon scanner,\ deflects the beam of laser radiation. For example, a single mirror in a galvanometer mirror-based apparatus permits for scanning of the beam in one direction, e.g. the Y axis relative to the sample. The deflection introduced by the positioner is carried throughout the optics, resulting in ablation of different locations on the sample dependent on the position of the mirror. The positioner may be coordinated (e.g., by a controller) with the position on the sample stage to determine the particular location on the sample ablated by the beam of laser radiation. The controller may also connects to the laser source to coordinate the production of laser pulses (so that pulses are produced by the laser source at a time when the positioner is at a defined position rather than while it is moving between positions).

However, instead of a single mirror positioner, a pair of mirror positioners may be used to induce deflections into the beam of laser radiation. As described elsewhere of herein, the mirror pair can be arranged to provide scanning in two orthogonal directions (X and Y), which can compensate for the movement of the sample on the sample stage.

Similarly, piezoelectric actuators on the shaft of which a mirror is mounted can be used as positioners to deflect the laser radiation onto different locations on the sample. Again, as mirror positioners, which are based on the movement of components with mass, there will inherently be inertia and so a time overhead inherent in movement of the mirror by this component. Accordingly, this positioner will be understood by the skilled person to have application in certain embodiments where nanosecond response times for the laser scanning system are not mandatory. Similarly, as it is based on a mirror, the piezoelectric mirror positioner may degrade laser radiation beam quality and increase the ablation spot size, and so will again be understood by the skilled person to be most applicable in situations which tolerate such effects on the beam.

In piezoelectric mirrors based on a tilt-tip mirror arrangement, direction of the laser radiation onto the sample in the X and Y axes is provided in a single component.

Piezoelectric mirrors are commercially available from suppliers such as Physik Instrumente (Germany).

Accordingly, in some embodiments of the invention, the laser scanner system comprises a piezoelectric mirror, such as a piezoelectric mirror array or a tilt-tip mirror.

In embodiments comprising only piezoelectric mirror based positioners, such as a piezoelectric mirror array or a tilt-tip mirror, the rate at which ablative laser pulses are capable of being directed at the sample may be between 200 Hz-1 MHz, 200 Hz-100 kHz, 200 Hz-50 kHz, 200 Hz-10 kHz, 1 kHz-1 MHz, 5 kHz-1 MHz, 10 kHz-1 MHz, 50 kHz-1 MHz, 100 kHz-1 MHz, 1 kHz to 100 kHz or 10 kHz-100 kHz. A third kind of positioner which is dependent on physical movement of the surface directing the laser radiation onto a sample is a MEMS (Micro-Electro Mechanical System) mirror. The micro mirror in this component can be actuated by electrostatic, electromechanic and piezoelectric effects. A number of strengths of this type of component derive from their small size, such as low weight, ease of positioning in the apparatus and low power consumption. However, as deflection of the laser radiation is still ultimately based on the movement of parts in the component, and as such the parts will experience inertia. Once again, as it is based on a mirror, the MEMS mirror positioner will degrade laser radiation beam quality and increase the ablation spot size, and so the skilled person will again understand that such scanner components are therefore applicable in situations which tolerate such effects on the laser radiation.

MEMS mirrors are commercially available from suppliers such as Mirrorcle Technologies (CA, USA), Hamamatsu (Japan) and Preciseley Microtechnology Corporation (Canada).

Accordingly, in some embodiments of the invention, the laser scanner system comprises a MEMS mirror.

In embodiments comprising only a MEMS mirror based positioner, the rate at which ablative laser pulses are capable of being directed at the sample may be between 200 Hz-1 MHz, 200 Hz-100 kHz, 200 Hz-50 kHz, 200 Hz-10 kHz, 1 kHz-1 MHz, 5 kHz-1 MHz, 10 kHz-1 MHz, 50 kHz-1 MHz, 100 kHz-1 MHz, 1 kHz to 100 kHz or 10 kHz-100 kHz. A further kind of positioner which is dependent on physical movement of the surface directing the laser radiation onto a sample is a polygon scanner. Here, a reflective polygon or multifaceted mirror spins on a mechanical axis, and every time a flat facet of the polygon is traversing the incoming beam an angular deflected scanning beam is produced. Polygon scanners are one dimensional scanners, can direct the laser beam along a scanned line (and so a secondary positioner is needed in order to introduce a second relative movement in the laser beam with respect to the sample, or the sample needs to be moved on the sample stage). In contrast to the back-and-forward motion of e.g. a galvanometer based scanner, once the end of one line of the raster scan has been reached, the beam is directed back to the position at the start of the scan row. The polygons can be regular or irregular, depending on the application. Spot size is dependent on facet size and flatness, and the scan line length/scan angle on the number of facets. Very high rotational speeds can be achieved, resulting in high scanning speeds. However, this kind of positioner does have drawback, in terms of lower positioning/feedback accuracy due to facet manufacturing tolerances and axial wobble, as well as potential wavefront distortion from the mirror surface. The skilled person will again understand that such scanner components are therefore applicable in situations which tolerate such effects on the laser radiation.

Polygon scanners are commercially available for example from Precision Laser Scanning (AZ, USA), II-VI (PA, USA), Nidec Copal Electronics Corp (Japan) inter alia.

In embodiments comprising only a polygon scanner based positioner, the rate at which ablative laser pulses are capable of being directed at the sample may be between 200 Hz-10 MHz, 200 Hz-1 MHz, 200 Hz-100 kHz, 200 Hz-50 kHz, 200 Hz-10 kHz, 1 kHz-10 MHz, 5 kHz-10 MHz, 10 kHz-10 MHz, 50 kHz-10 MHz, 100 kHz-10 MHz, 1 kHz-1 MHz, 10 kHz-1 MHz or 100 kHz-1 MHz. Unlike the preceding types for laser scanner system component, EODs are solid state components—i.e. they comprise no moving parts. Accordingly, they do not experience mechanical inertia in deflecting laser radiation and so have very fast response times, of the order of 1 ns. They also do not suffer from wear as mechanical components do. An EOD is formed of an optically transparent material (e.g. a crystal) that has a refractive index which varies dependent on the electric field applied across it, which in turn is controlled by the application of an electric voltage over the medium. The refraction of the laser radiation is caused by the introduction of a phase delay across the cross section of the beam. If the refractive index varies linearly with the electric field, this effect is referred to as the Pockels effect. If it varies quadratically with the field strength, it is referred to as the Kerr effect. The Kerr effect is usually much weaker than the Pockels effect. Two typical configurations are an EOD based on refraction at the interface(s) of an optical prism, and based on refraction by an index gradient that exists perpendicular to the direction of the propagation of the laser radiation. To place an electric field across the EOD, electrodes are bonded to opposing sides of the optically transparent material that acts as the medium. Bonding one set of opposed electrodes generates a 1-dimensional scanning EOD. Bonding a second set of electrodes orthogonally to the first set electrodes generates a 2-dimensional (X, Y) scanner.

The deflection angle of EODs is lower than galvanometer mirrors, for instance, but by placing several EODs in sequence, the angle can be increased, if required for a given apparatus set up. Exemplary materials for the refractive medium in the EOD include Potassium Tantalate Niobate KTN ($KTa_xNb_{1-x}O_3$), $LiTaO_3$, $LiNbO_3$, $BaTiO_3$, $SrTiO_3$, SBN ($Sr_{1-x}Ba_xNb_2O_6$) and $KTiOPO_4$ with KTN displaying greater deflection angles at the same field strength.

The angular accuracy of EODs is high, and is principally dependent on the accuracy of the driver connected to the electrodes. Further, as noted above, the response time of EODs is very quick, and quicker even than the AODs discussed below (due to the fact that a (changing) electric field in a crystal is established at the speed of light in the material, rather than at the acoustic velocity in the material; see discussion in Romer and Bechtold, 2014, Physics Procedia 56:29-39).

Accordingly, in some embodiments of the invention, the laser scanner system comprises an EOD. In some embodiments, the EOD is one in which two sets of electrodes have been orthogonally connected to the refractive medium.

In embodiments comprising an EOD based positioner, the rate at which ablative laser pulses are capable of being directed at the sample may be between 200 Hz-100 MHz, 200 Hz-10 MHz, 200 Hz-1 MHz, 200 Hz-100 kHz, 200 Hz-50 kHz, 200 Hz-10 kHz, 1 kHz-100 MHz, 5 kHz-100 MHz, 10 kHz-100 MHz, 50 kHz-100 MHz, 100 kHz-100 MHz, 1 MHz-100 MHz, 10-100 MHz, 1 kHz-10 MHz, 10 kHz-10 MHz, or 100 kHz-10 MHz. This class of positioner is also a solid state component. The deflection of the component is based on propagating sound waves in an optically transparent material to induce a periodically changing refractive index. The changing refractive index occurs because of compression and rarefaction of the material (i.e. changing density) due to the sound waves propagating through the material. The periodically changing refractive index diffracts a laser beam traveling through the material by acting like an optical grating.

The AOD is generated by bonding a transducer (typically a piezoelectric element) to an acousto-optic crystal (e.g. $TeO_2$). The transducer, driven by an electrical amplifier, introduces acoustic waves into the refractive medium. At the opposite end, the crystal is typically skew cut and fitted with an acoustic absorbing material to avoid reflection of the acoustic wave back into the crystal.

As the waves propagate in one direction through the crystal, this forms a 1-dimensional scanner. By placing two AODs orthogonally in series, or by bonding two transducers on orthogonal crystal faces, a 2-dimensional scanner can be generated.

As for EODs, deflection angle of AODs is lower than galvanometer mirrors, but again compared to such mirror-based scanners the angular accuracy is high, with the frequency driving the crystal being digitally controlled, and commonly resolvable to 1 Hz. Römer and Bechtold, 2014, note that drift, common for galvo-based scanners, as well as temperature dependency in comparison to analog controllers, are not usually problems encountered by AODs.

Exemplary materials for use as the refractive medium of the AOD include tellurium dioxide, fused silica, crystalline quartz, sapphire, AMTIR, GaP, GaAs, InP, SF6, lithium niobate, $PbMoO_4$, arsenic trisulfide, tellurite glass, lead silicate, $Ge_{55}As_{12}S_{33}$, mercury (I) chloride, and lead (II) bromide.

In order to change the angle of deflection, the frequency of sound introduced to the crystal must be changed, and it takes a finite amount of time for the acoustic wave to fill the crystal (dependent on the speed of propagation of the soundwave in the crystal and on the size of the crystal), thereby meaning there is a degree of delay. Nevertheless, response time is relatively fast, compared to laser system positioners based on moving parts.

A further characteristic of AODs which can be exploited in particular instances is that the acoustic power applied to the crystal determines how much of the laser radiation is diffracted versus the zero-order (i.e. non-diffracted) beam. The non-diffracted beam is typically directed to a beam dump. Accordingly, an AOD can be used to effectively control (or modulate) the intensity and power of the deflected beam at high speed.

Diffraction efficiency of the AOD is typically non-linear, and accordingly, curves of diffraction efficiency vs. power can be mapped for different input frequencies. The mapped efficiency curves for each frequency can then be recorded as an equation or in a look-up table for subsequent use in the apparatus and methods disclosed herein.

Accordingly, in some embodiments of the invention, the laser scanner system comprises an AOD.

Instead of a rotating mirror a solid state positioner (e.g. an AOD or EOD) may be used to induce deflections into the beam of laser radiation rather than a mirror-based positioner. As described elsewhere of herein, the solid state scanner can scan in two orthogonal directions (X and Y), either by attaching orthogonal electrodes to an EOD medium, or by the arrangement of two AODs in orthogonally in series.

In embodiments comprising an AOD based positioner, the rate at which ablative laser pulses are capable of being directed at the sample may be between 200 Hz-100 MHz, 200 Hz-10 MHz, 200 Hz-1 MHz, 200 Hz-100 kHz, 200 Hz-50 kHz, 200 Hz-10 kHz, 1 kHz-100 MHz, 5 kHz-100 MHz, 10 kHz-100 MHz, 50 kHz-100 MHz, 100 kHz-100 MHz, 1 MHz-100 MHz, 10-100 MHz, 1 kHz-10 MHz, 10 kHz-10 MHz, or 100 kHz-10 MHz. In the preceding paragraphs, two types of laser scanning system positioners are discussed: mirror based, comprising moving parts, and solid state positioners. The former is characterised by high angles of deflection, but comparatively slow response times due to inertia. In contrast, solid state positioners have a lower deflection angle range, but much quicker response times. Accordingly, in some embodiments of the invention, the laser scanning system includes both mirror based and solid state components in series. This arrangement takes advantages of the strengths of both, e.g. the large range provided by the mirror-based components, but accommodating the inertia of the mirror-based components. See, for instance, Matsumoto et al., 2013 (Journal of Laser Micro/Nanoengineering 8:315:320).

Accordingly, a solid state positioner AOD or EOD) can be used for instance to correct for errors in the mirror-based scanner components. In this case, positional sensors relating to mirror-position feedback to the solid state component, and the angle of deflection introduced into the beam of laser radiation by the solid state component can be altered appropriately to correct for positional error of the mirror-based scanner components.

One example of a combined system includes a galvanometer mirror and an AOD (where the AOD may enable deflection in one or two directions (by using two AODs in series, or bonding two drivers to orthogonal faces of the crystal of a single AOD)). The system may comprise two galvanometer mirrors so as to generate a two dimensional scanning system, in combination with an AOD (where the AOD may enable deflection in one or two directions (by using two AODs in series, or bonding two drivers to orthogonal faces of the crystal of a single AOD)). In such a system, the rate at which ablative laser pulses are capable of being directed at the sample may be between 200 Hz-100 MHz, 200 Hz-10 MHz, 200 Hz-1 MHz, 200 Hz-100 kHz, 200 Hz-50 kHz, 200 Hz-10 kHz, 1 kHz-100 MHz, 5 kHz-100 MHz, 10 kHz-100 MHz, 50 kHz-100 MHz, 100 kHz-100 MHz, 1 MHz-100 MHz, 10-100 MHz, 1 kHz-10 MHz, 10 kHz-10 MHz, or 100 kHz-10 MHz. An alternative example of a combined system includes a galvanometer mirror and an EOD (where the EOD may enable deflection in one or two directions (by bonding two orthogonally arranged electrodes to the crystal)). The system may comprise two galvanometer mirrors so as to generate a two dimensional scanning system, in combination with an EOD (where the EOD may enable deflection in one or two directions (by bonding two orthogonally arranged electrodes to the crystal)). In such as system, the rate at which ablative laser pulses are capable of being directed at the sample may be between 200 Hz-100 MHz, 200 Hz-10 MHz, 200 Hz-1 MHz, 200 Hz-100 kHz, 200 Hz-50 kHz, 200 Hz-10 kHz, 1 kHz-100 MHz, 5 kHz-100 MHz, 10 kHz-100 MHz, 50 kHz-100 MHz, 100 kHz-100 MHz, 1 MHz-100 MHz, 10-100 MHz, 1 kHz-10 MHz, 10 kHz-10 MHz, or 100 kHz-10 MHz. To control the positioners of the laser scanning system, the laser scanning system may comprise a scanner control module (such as a computer or a programmed chip), which coordinates the movement of the positioners in the Y and/or X axes, together with the movement of the sample stage. In some instances, such as back and forth rastering, the appropriate pattern will be pre-programmed into the chip. In other instances, however, inverse kinematics can be applied by the control module to determine the appropriate ablation pattern to be followed. Inverse kinematics may be particularly useful, for example, in generating arbitrary ablation patterns, so as to plot the best ablation course between multiple and/or irregularly shaped cells to be ablated. The scanner control module may also co-ordinate the emission of pulses of laser radiation, e.g. by also co-ordinating operation of the pulse picker.

Sometimes, a positioner can cause dispersion of the beam of laser radiation it directs. Accordingly, in some embodiments of the apparatus described herein, the laser scanning system comprises at least one dispersion compensator between the positioner and/or the second positioner and the sample, adapted so as to compensate for any dispersion caused by the positioner. When the positioner is an AOD and/or the second positioner is an AOD the dispersion compensator is (i) a diffraction grating having a line spacing suitable for compensating for the dispersion caused by the positioner and/or second positioner; (ii) a prism suitable for compensating for the dispersion caused by the positioner and/or second positioner appropriate material, thickness, and prism angle); (iii) a combination comprising the diffraction grating (i) and prism (ii); and/or (iv) a further acousto-optic device. In instances where a first positioner causes a dispersion and a second positioner causes a dispersion, the laser scanning system may comprise a first dispersion compensator to compensate for any dispersion caused by the first positioner and a second dispersion compensator to compensate for any dispersion caused by the second positioner. WO03/028940 describes how another appropriately adapted AOD can be used to compensate for dispersion caused by an AOD positioner.

Sometimes, due to the movement of the positioners directing laser radiation to different locations, the focal length of a beam of radiation can vary with respect to the position of the sample. This can be compensated for in a number of ways. For instance, a movable focusing lens can be moved so as to maintain a spot size of constant, or near constant, diameter on the sample irrespective of the particular location on the sample to which the laser radiation is being directed. Alternatively, a tunable focus lens (commercially available from Optotune), may be used. It is also possible to compensate for spot size variation by altering the height of the sample stage in the z axis. Both of these techniques rely on moving parts, however, introducing a timing overhead into operation of the system. If an AOD is used with a Gaussian beam, ablation spot size can be controlled by power applied to the crystal in the AOD, so as to modulate rapidly first order versus zero order beam intensity.

In the alternative arrangements presented in FIGS. 2-4, components may be similar to those shown in FIG. 1, with the exception that the system operates to ablate the sample through the sample carrier. This arrangement can be preferred for instance when additional kinetic energy is desired to be imparted into the sample material being ablated, to assist the material's clearance from the area proximal to the ablation spot. Alternatively or in addition, the configurations presented in FIGS. 2, 3 and/or 4 may allow for a smaller spot size as described herein. In some embodiments, ablation through the sample carrier can be combined with laser scanning optics.

Lasers

Generally, the choice of wavelength and power of the laser used for ablation of the sample can follow normal usage in cellular analysis. The laser must have sufficient fluence to cause ablation to a desired depth, without substantially ablating the sample carrier. A laser fluence of between 0.1-5 J/cm² is typically suitable e.g. from 3-4 J/cm² or about 3.5 J/cm², and the laser will ideally be able to generate a pulse with this fluence at a rate of 200 Hz or greater. In some instances, a single laser pulse from such a laser should be sufficient to ablate cellular material for analysis, such that the laser pulse frequency matches the frequency with which ablation plumes are generated. In general, to be a laser useful for imaging biological samples, the laser should produce a pulse with duration below 100 ns (preferably below 1 ns) which can be focused to, for example, the specific spot sizes discussed herein.

For instance, the frequency of ablation by the laser system is within the range 200 Hz-100 MHz, 200 Hz-10 MHz, 200 Hz-1 MHz, 200 Hz-100 kHz, within the range 500-50 kHz, or within the range 1 kHz-10 kHz.

At these frequencies the instrumentation must be able to analyse the ablated material rapidly enough to avoid substantial signal overlap between consecutive ablations, if it is desired to resolve each ablated plume individually (which as set out below may not necessarily be desired when firing a burst of pulses at a sample). It is preferred that the overlap between signals originating from consecutive plumes is <10% in intensity, more preferably <5%, and ideally <2%. The time required for analysis of a plume will depend on the washout time of the sample chamber (see sample chamber section below), the transit time of the plume aerosol to and through the laser ionisation system, and the time taken to analyse the ionised material. Each laser pulse can be correlated to a pixel on the image of the sample that is subsequently built up, as discussed in more detail below.

In some embodiments, the laser source comprises a laser with a nanosecond pulse duration or an ultrafast laser (pulse duration of 1 μs ($10^{-12}$ s) or quicker, such as a femtosecond laser. Ultrafast pulse durations provide a number of advantages, because they limit heat diffusion from the ablated zone, and thereby provide more precise and reliable ablation craters, as well as minimising scattering of debris from each ablation event. Femtosecond lasers are particularly useful in the systems and apparatus described here. In particular, femtosecond lasers are highly compatible with systems including laser scanning components, and because the short pulse duration enables ablation techniques based on multiphoton events and electron seeding processes. Three attributes of femtosecond lasers make them particularly suited for this application. The first attribute is a high repetition rate of typical configurations on femtoasecond lasers which is commonly in the range between 1 MHz and 100 MHz. As a contrast, nano-second lasers are commonly limited in pulse rate below 100 kHz. The second attribute is the non-linear ablation mechanism. The non-linear ablation sharpens the definition of ablation edge and allows for ablation at higher spatial resolution. Thirdly, the non-linear ablation threshold may also be less material specific which makes it easier to get consistent dimensions for ablation spots when studying non-uniform material such as a tissue.

In some instances a femtosecond laser is used as the laser source. A femtosecond laser is a laser which emits optical pulses with a duration below 1 μs. The generation of such short pulses often employs the technique of passive mode locking. Femtosecond lasers can be generated using a number of types of laser. Typical durations between 30 fs and 30 μs can be achieved using passively mode-locked solid-state bulk lasers. Similarly, various diode-pumped lasers, e.g. based on neodymium-doped or ytterbium-doped gain media, operate in this regime. Titanium—sapphire lasers with advanced dispersion compensation are even suitable for pulse durations below 10 fs, in extreme cases down to approximately 5 fs. The pulse repetition rate is in most cases between 10 MHz and 500 MHz, though there are low repetition rate versions with repetition rates of a few megahertz for higher pulse energies (available from e.g. Lumentum (CA, USA), Radiantis (Spain), Coherent (CA, USA)). This type of laser can come with an amplifier system which increases the pulse energy There are also various types of ultrafast fiber lasers, which are also in most cases passively mode-locked, typically offering pulse durations between 50 and 500 fs, and repetition rates between 10 and 100 MHz. Such lasers are commercially available from e.g. NKT Photonics (Denmark; formerly Fianium), Amplitude Systems (France), LaserFemto (CA, USA). The pulse energy of this type of laser can also be increased by an amplifier, often in the form of an integrated fiber amplifier.

Some mode-locked diode lasers can generate pulses with femtosecond durations. Directly at the laser output, the pulse duration is usually around several hundred femtoseconds (available e.g. from Coherent (CA, USA)).

Femtosecond lasers are particularly suited for use with immersion lenses, such as oil immersion lenses (as discussed above). Oil immersion lenses can achieve a laser spot diameter of around 160 nm but since ablation using femtosecond lasers is a multi-photon process, the effective spot diameter is reduced by a factor of $\sqrt{m}$ when used with a femtosecond laser, where m is the order of the non-linear process. In this way, it is possible to achieve an effective spot diameter of less than 100 nm. All possible configurations of the apparatus including immersion lenses as set out above can achieve a 100 nm ablation spot size when used with femtosecond lasers, and so the present invention provides apparatus and methods which provide a ten times improvement in spatial resolution when compared to traditional IMC and IMS. Femtosecond lasers generally have wavelengths in the near infrared region (700-1300 nm), which means frequency-conversion techniques must be employed to shorten their wavelength so that the 100 nm ablation spot diameter can be achieved. The most straightforward and well-known of these is second harmonic generation (SHG), which can efficiently convert a near infrared laser beam to visible wavelengths, where commercial off-the-shelf microscope optics can be used.

In some instances, a picosecond laser is used. Many of the types of lasers already discussed in the preceding paragraphs can also be adapted to produce pulses of picosecond range duration. The most common sources are actively or passively mode-locked solid-state bulk lasers, for example a passively mode-locked Nd-doped YAG, glass or vanadate laser. Likewise, picosecond mode-locked lasers and laser diodes are commercially available (e.g. NKT Photonics (Denmark), EKSPLA (Lithuania)).

Nanosecond pulse duration lasers (gain switched and Q switched) can also find utility in particular apparatus set ups (Coherent (CA, USA), Thorlabs (NJ, USA)). Nanosecond UV lasers are particularly well suited for the solid immersion lenses as set out above. In particular, nanosecond UV lasers of 266 nm wavelength can be used with diamond and fused silica solid immersion lenses to focus the light to a spot size of 100 nm or below. As one of skill in the art appreciates, laser ablation using UV lasers is generally a thermal process, which means an area around the laser spot size will be affected by the heat from the ablation process. This sets limits on the attainable ablation spot size, and so as a result the person of skill in the art accordingly would appreciate that UV lasers will be applicable in certain scenarios, but other lasers may be of more utility in other scenarios.

Alternatively, a continuous wave laser may be used, externally modulated to produce nanosecond or shorter duration pulses.

Typically, the laser beam used for ablation in the laser systems discussed herein has a spot size, i.e., at the sampling location, of 100 µm or less, such as 50 µm or less, 25 µm or less, 20 µm or less, 15 µm or less, or 10 µm or less, such as about 3 µm or less, about 2 µm or less, about 1 µm or less, about 500 nm or less, about 250 nm or less. Where an immersion medium is applied between the objective lens and the sample, as described above in the section on page 8, smaller spot sizes can be achieved, such as 200 nm or less, 150 nm or less, or 100 nm or less. The distance referred to as spot size corresponds to the longest internal dimension of the beam, e.g. for a circular beam it is the beam diameter, for a square beam it corresponds to the length of the diagonal between opposed corners, for a quadrilateral it is the length of the longest diagonal etc. (as noted above, the diameter of a circular beam with a Gaussian distribution is defined as the distance between the points at which the fluence has decreased to $1/e^2$ times the peak fluence). As an alternative to the Gaussian beam, beam shaping and beam masking can be employed to provide the desired ablation spot. For example, in some applications, a square ablation spot with a top hat energy distribution can be useful (i.e. a beam with near uniform fluence as opposed to a Gaussian energy distribution). This arrangement reduces the dependence of the ablation spot size on the ratio between the fluence at the peak of the Gaussian energy distribution and the threshold fluence. Ablation at close to the threshold fluence provides more reliable ablation crater generation and controls debris generation. Accordingly, the laser system may comprise beam masking and/or beam shaping components, such as a diffractive optical element, arranged in a Gaussian beam to re-shame the beam and produce a laser focal spot of uniform or near-uniform fluence, such as a fluence that varies across the beam by less than ±25%, such as less than ±20%, ±15%, ±10% or less than ±5%. Sometimes, the laser beam has a square cross-sectional shape. Sometimes, the beam has a top hat energy distribution. As set out above, in the context of the present invention, the distance referred to as spot size is the longest internal dimension of the beam at the sampling location, i.e. the spot size is the lateral dimension of the beam, so for example, the spot size of a circular beam is the diameter. However, the skilled person will appreciate that the focal spot of an objective lens is a three dimensional volume and that the axial dimensions of a focussed spot size are generally longer than the lateral dimensions so that in some instances, the axial dimension of the focal spot may be longer than the distance referred to as 'spot size' in the context of the present invention. Beam shaping and masking can also be used to enable an apparatus which can switch between the high resolution spot sizes achievable with immersion lenses to larger spot sizes, if desired by the user. As well as high resolution imaging under certain conditions, when the project specification requires it, large spots can be used (e.g. where a lower resolution is suitable, or where a greater area of tissue is required to be sampled and analysed in a given time).

When used for analysis of biological samples, in order to analyse individual cells the spot size of laser beam used will depend on the size and spacing of the cells. For example, where the cells are tightly packed against one another (such as in a tissue section) one or more laser sources in the laser system can have a spot size which is no larger than these cells. This size will depend on the particular cells in a sample, but in general the laser spot will have a diameter of less than 4 µm e.g. about 3 µm or less, about 2 µm or less, about 1 µm or less, about 500 nm or less, about 250 nm or less. In order to analyse given cells at a subcellular resolution the system uses a laser spot size which is no larger than these cells, and more specifically uses a laser spot size which can ablate material with a subcellular resolution. The lower the spot size, the greater the resolution resulting image. Thus, where high resolution subcellular imaging is required, the techniques described herein can be used. Sometimes, single cell analysis can be performed using a spot size larger than the size of the cell, for example where cells are spread out on the slide, with space between the cells (e.g. such as after analysis by electron microscopy such that the internal structure of the cell has been determined separated from the elemental analysis of the cell). Here, a larger spot size can be used and single cell characterisation achieved, because the additional ablated area around the cell of interest does not comprise additional cells. The particular spot size used can therefore be selected appropriately dependent upon the size of the cells being analysed. In biological samples, the cells will rarely all be of the same size, and so if subcellular resolution imaging is desired, the ablation spot size should be smaller than the smallest cell, if constant spot size is maintained throughout the ablation procedure. Small spot sizes can be achieved using focusing of laser beams. A laser spot diameter of 1 µm corresponds to a laser focus point (i.e. the diameter of the laser beam at the focal point of the beam) of 1 µm, but the laser focus point can vary by +20% or more due to spatial distribution of energy on the target (for instance, Gaussian beam shape) and variation in total laser energy with respect to the ablation threshold energy. Suitable objectives for focusing a laser beam include a reflecting objective, such as an objective of a Schwarzschild Cassegrain design (reverse Cassegrain). Refracting objectives can also be used, as can combination reflecting-refracting objectives. A single aspheric lens can also be used to achieve the required focusing. A solid-immersion lens or diffractive optic can also be used to focus the laser beam. Another means for controlling the spot size of the laser, which can be used alone or in combination with the above objectives is to pass the beam through an aperture prior to focusing. Different beam diameters can be achieved by passing the beam through apertures of different diameter from an array of diameters. In some instances, there is a single aperture of variable size, for example when the aperture is a diaphragm aperture. Sometimes, the diaphragm aperture is an iris diaphragm. Variation of the spot size can also be achieved through dithering of the optics. The one or more lenses and one or more apertures are positioned between the laser and the sample stage.

For completeness, the standard lasers for LA at subcellular resolution, as known in the art, are excimer or exciplex lasers. Suitable results can be obtained using an argon fluoride laser ($\lambda$=193 nm). Pulse durations of 10-15 ns with these lasers can achieve adequate ablation for certain applications.

Overall, the laser pulse frequency and strength are selected in combination with the response characteristics of the MS detector to permit distinct detection of individual laser ablation plumes. In combination with using a small laser spot and a sample chamber having a short washout time, rapid and high resolution imaging is now feasible.

Laser Ablation Focal Point

To maximise the efficiency of a laser to ablate material from a sample, the sample should be at a suitable position with regard to the laser's focal point, for example at the focal point, as the focal point is where the laser beam will have the smallest diameter and so most concentrated energy. This can be achieved in a number of ways. A first way is that the sample can be moved in the axis of the laser light directed upon it (i.e. up and down the path of the laser light/towards and away from the laser source) to the desired point at which the light is of sufficient intensity to effect the desired ablation. Alternatively, or additionally, lenses can be used to move the focal point of the laser light and so its effective ability to ablate material at the location of the sample, for example by demagnification. The one or more lenses are positioned between the laser and the sample stage. A third way, which can be used alone or in combination with either or both of the two preceding ways, is to alter the position of the laser.

To assist the user of the system in placing the sample at the most suitable location for ablation of material from it, a camera can be directed at the stage holding the sample (discussed in more detail below). Accordingly, the disclosure provides a laser ablation sampling system comprising a camera directed on the sample stage. The image detected by the camera can be focussed to the same point at which the laser is focussed. This can be accomplished by using the same objective lens for both laser ablation and optical imaging. By bringing the focal point of two into accordance, the user can be sure that laser ablation will be most effective when the optical image is in focus. Precise movement of the stage to bring the sample into focus can be effected by use of piezo activators, as available from Physik Instrumente, Cedrat-technologies, Thorlabs and other suppliers.

In a further mode of operation, the laser ablation is directed to the sample through the sample carrier. In this instance, the sample support should be chosen so that it is transparent (at least partially) to the frequency of laser radiation being employed to ablate the sample. Ablation through the sample can have advantages in particular situations, because this mode of ablation can impart additional kinetic energy to the plume of material ablated from the sample, driving the ablated material further away from the surface of the sample, so facilitating the ablated material's being transported away from the sample for analysis in the detector.

In order to achieve 3D-imaging of the sample, the sample, or a defined area thereof, can be ablated to a first depth, which is not completely through the sample. Following this, the same area can be ablated again to a second depth, and so on to third, fourth, etc. depths. This way a 3D image of the sample can be built up. In some instances, it may be preferred to ablate all of the area for ablation to a first depth before proceeding to ablate at the second depth. Alternatively, repeated ablation at the same spot may be performed to ablate through different depths before proceeding onto the next location in the area for ablation. In both instances, deconvolution of the resulting signals at the MS to locations and depths of the sample can be performed by the imaging software. Thick tissue staining can be employed and the tissue is stabilized in the wet state similar to the workflow employed in confocal imaging (Clendenon et al., 2011. Microsc Microanal. 17:614-617).

Sample Chamber of the Laser Ablation Sampling System

The sample is placed in the sample chamber when it is subjected to laser ablation. The sample chamber comprises a stage, which holds the sample (typically the sample is on a sample carrier). When ablated, the material in the sample forms plumes, and the flow of gas passed through the sample chamber from a gas inlet to a gas outlet carries away the plumes of aerosolised material, including any labelling atoms that were at the ablated location. The gas carries the material to the ionisation system, which ionises the material to enable detection by the detector. The atoms, including the labelling atoms, in the sample can be distinguished by the detector and so their detection reveals the presence or absence of multiple targets in a plume and so a determination of what targets were present at the ablated locus on the sample. Accordingly, the sample chamber plays a dual role in hosting the solid sample that is analysed, but also in being the starting point of the transfer of aerosolised material to the ionisation and detection systems. This means that the gas flow through the chamber can affect how spread out the ablated plume of material becomes as it passes through the system. A measure of how spread out the ablated plume becomes is the washout time of the sample chamber. This figure is a measure of how long it takes material ablated from the sample to be carried out of the sample chamber by the gas flowing through it.

The spatial resolution of the signals generated from laser ablation (i.e. when ablation is used for imaging rather than exclusively for clearing, as discussed below) in this way depends on factors including: (i) the spot size of the laser, as signal is integrated over the total area which is ablated; and the speed with which plumes are generated versus the movement of the sample relative to the laser, and (ii) the speed at which a plume can be analysed, relative to the speed at which plumes are being generated, to avoid overlap of signal from consecutive plumes as mentioned above. Accordingly, being able to analyse a plume in the shortest time possible minimises the likelihood of plume overlap (and so in turn enables plumes to be generated more frequently), if individual analysis of plumes is desired.

Accordingly, a sample chamber with a short washout time (e.g. 100 ms or less) is advantageous for use with the apparatus and methods disclosed herein. A sample chamber with a long washout time will either limit the speed at which an image can be generated or will lead to overlap between signals originating from consecutive sample spots (e.g. Kindness et al. (2003; Clin Chem 49:1916-23), which had signal duration of over 10 seconds). Therefore aerosol washout time is a key limiting factor for achieving high resolution without increasing total scan time. Sample chambers with washout times of ≤100 ms are known in the art. For example, Gurevich & Hergenroder (2007; *J. Anal. At. Spectrom.*, 22:1043-1050) discloses a sample chamber with a washout time below 100 ms. A sample chamber was disclosed in Wang et al. (2013; *Anal. Chem.* 85:10107-16) (see also WO 2014/146724) which has a washout time of 30 ms or less, thereby permitting a high ablation frequency (e.g. above 20 Hz) and thus rapid analysis. Another such sample chamber is disclosed in WO 2014/127034. The sample chamber in WO 2014/127034 comprises a sample capture cell configured to be arranged operably proximate to the target, the sample capture cell including: a capture cavity having an opening formed in a surface of the capture cell, wherein the capture cavity is configured to receive, through the opening, target material ejected or generated from the laser ablation site and a guide wall exposed within the capture cavity and configured to direct a flow of the carrier gas within the capture cavity from an inlet to an outlet such that at least a portion of the target material received within the capture cavity is transferrable into the outlet as a sample. The volume of the capture cavity in the sample chamber of WO 2014/127034 is less than 1 $cm^3$ and can be below 0.005 $cm^3$. Sometimes the sample chamber has a washout time of 25 ms or less, such as 20 ms, 10 ms or less, 5 ms or less, 2 ms or less, 1 ms, less or 500 μs or less, 200 μs or less, 100 μs or less, 50 μs or less, or 25 μs or less. For example, the sample chamber may have a washout time of 10 μs or more. Typically, the sample chamber has a washout time of 5 ms or less.

For completeness, sometimes the plumes from the sample can be generated more frequently than the washout time of the sample chamber, and the resulting images will smear accordingly (e.g. if the highest possible resolution is not deemed necessary for the particular analysis being undertaken).

The sample chamber typically comprises a translation stage which holds the sample (and sample carrier) and moves the sample relative to a beam of laser radiation. When a mode of operation is used which requires the direction of laser radiation through the sample carrier to the sample, the stage holding the sample carrier should also be transparent to the laser radiation used.

Thus, the sample may be positioned on the side of the sample carrier (e.g., glass slide) facing the laser radiation as it is directed onto the sample, such that ablation plumes are released on, and captured from, the same side as that from which the laser radiation is directed onto the sample. Alternatively, the sample may be positioned on the side of the sample carrier opposite to the laser radiation as it is directed onto the sample (i.e. the laser radiation passes through the sample carrier before reaching the sample), and ablation plumes are released on, and captured from, the opposite side to the laser radiation. Direction of laser radiation onto the sample through the sample carrier is of particular utility when an immersion medium, such as a solid immersion lens or a liquid immersion lens.

One feature of a sample chamber, which is of particular use where specific portions in various discrete areas of sample are ablated, is a wide range of movement in which the sample can be moved in the x and y (i.e. horizontal) axes in relation to the laser (where the laser beam is directed onto the sample in the z axis), with the x and y axes being perpendicular to one another. More reliable and accurate relative positions are achieved by moving the stage within the sample chamber and keeping the laser's position fixed in the laser ablation sampling system of the apparatus. The greater the range of movement, the more distant the discrete ablated areas can be from one another. The sample is moved in relation to the laser by moving the stage on which the sample is placed. Accordingly, the sample stage can have a range of movement within the sample chamber of at least 10 mm in the x and y axes, such as 20 mm in the x and y axes, 30 mm in the x and y axes, 40 mm in the x and y axes, 50 mm in the x and y axes, such as 75 mm in the x and y axes. Sometimes, the range of movement is such that it permits the entire surface of a standard 25 mm by 75 mm microscope slide to be analysed within the chamber. Of course, to enable subcellular ablation to be achieved, in addition to a wide range of movement, the movement should be precise. Accordingly, the stage can be configured to move the sample in the x and y axes in increments of less than 10 μm, such as less than 5 μm, less than 4 μm, less than 3 μm, less than 2 μm, 1 μm, or less than 1 μm, less than 500 nm, less than 200 nm, less than 100 nm. For example, the stage may be configured to move the sample in increments of at least 50 nm. Precise stage movements can be in increments of about 1 μm, such as 1 μm±0.1 μm. Commercially available microscope stages can be used, for example as available from Thorlabs, Prior Scientific, and Applied Scientific Instrumentation. Alternatively, the motorised stage can be built from components, based on positioners providing the desired range of movement and suitably fine precision movement, such as the SLC-24 positioners from Smaract. The movement speed of the sample stage can also affect the speed of the analysis. Accordingly, the sample stage has an operating speed of greater than 1 mm/s, such as 10 mm/s, 50 mm/s or 100 mm/s.

Naturally, when a sample stage in a sample chamber has a wide range of movement, the sample chamber must be sized appropriately to accommodate the movements of the stage. Sizing of the sample chamber is therefore dependent on size of the sample to be involved, which in turn determines the size of the mobile sample stage. Exemplary sizes of sample chamber have an internal chamber of 10×10 cm, 15×15 cm or 20×20 cm. The depth of the chamber may be 3 cm, 4 cm or 5 cm. The skilled person will be able to select appropriate dimensions following the teaching herein. The internal dimensions of the sample chamber for analysing biological samples using a laser ablation sampler must be bigger than the range of movement of the sample stage, for example at least 5 mm, such as at least 10 mm. This is because if the walls of the chamber are too close to the edge of the stage, the flow of the carrier gas passing through the chamber which takes the ablated plumes of material away from the sample and into the ionisation system can become turbulent. Turbulent flow disturbs the ablated plumes, and so instead of remaining as a tight cloud of ablated material, the plume of material begins to spread out after it has been ablated and carried away to the ionisation system of the apparatus. A broader peak of the ablated material has negative effects on the data produced by the ionisation and detection systems because it leads to interference due to peak overlap, and so ultimately, less spatially resolved data, unless the rate of ablation is slowed down to such a rate that it is no longer experimentally of interest.

As noted above, the sample chamber comprises a gas inlet and a gas outlet that takes material to the ionisation system. However, it may contain further ports acting as inlets or outlets to direct the flow of gas in the chamber and/or provide a mix of gases to the chamber, as determined to be appropriate by the skilled artisan for the particular ablative process being undertaken.

Camera

In addition to identifying the most effective positioning of the sample for laser ablation, the inclusion of a camera (such as a charged coupled device image sensor based (CCD) camera or an active pixel sensor based camera), or any other light detecting means in a laser ablation sampling system enables various further analyses and techniques. A CCD is a means for detecting light and converting it into digital information that can be used to generate an image. In a CCD image sensor, there are a series of capacitors that detect light, and each capacitor represents a pixel on the determined image. These capacitors allow the conversion of incoming photons into electrical charges. The CCD is then used to read out these charges, and the recorded charges can be converted into an image. An active-pixel sensor (APS) is an image sensor consisting of an integrated circuit containing an array of pixel sensors, each pixel containing a photodetector and an active amplifier, e.g. a CMOS sensor.

A camera can be incorporated into any laser ablation sampling system discussed herein. The camera can be used to scan the sample to identify cells of particular interest or regions of particular interest (for example cells of a particular morphology), or for fluorescent probes specific for an antigen, or an intracellular or structure. In certain embodiments, the fluorescent probes are histochemical stains or antibodies that also comprise a detectable metal tag. Once such cells have been identified, then laser pulses can be directed at these particular cells to ablate material for analysis, for example in an automated (where the system both identifies and ablates the feature(s)/regions(s), such as cell(s), of interest) or semi-automated process (where the user of the system, for example a clinical pathologist, identifies the features/region(s) of interest, which the system then ablates in an automated fashion). This enables a significant increase in the speed at which analyses can be conducted, because instead of needing to ablate the entire sample to analyse particular cells, the cells of interest can be specifically ablated. This leads to efficiencies in methods of analysing biological samples in terms of the time taken to perform the ablation, but in particular in the time taken to interpret the data from the ablation, in terms of constructing images from it. Constructing images from the data is one of the more time-consuming parts of the imaging procedure, and therefore by minimising the data collected to the data from relevant parts of the sample, the overall speed of analysis is increased.

The camera may record the image from a confocal microscope. Confocal microscopy is a form of optical microscopy that offers a number of advantages, including the ability to reduce interference from background information (light) away from the focal plane. This happens by elimination of out-of-focus light or glare. Confocal microscopy can be used to assess unstained samples for the morphology of the cells, or whether a cell is a discrete cell or part of a clump of cells. Often, the sample is specifically labelled with fluorescent markers (such as by labelled antibodies or by labelled nucleic acids). These fluorescent makers can be used to stain specific cell populations (e.g. expressing certain genes and/or proteins) or specific morphological features on cells (such as the nucleus, or mitochondria) and when illuminated with an appropriate wavelength of light, these regions of the sample are specifically identifiable. Some systems described herein therefore can comprise a laser for exciting fluorophores in the labels used to label the sample. Alternatively, an LED light source can be used for exciting the fluorophores. Non-confocal (e.g. wide field) fluorescent microscopy can also be used to identify certain regions of the biological sample, but with lower resolution than confocal microscopy.

An alternative imaging technique is two-photon excitation microscopy (also referred to as non-linear or multiphoton microscopy). The technique commonly employs near-IR light to excite fluorophores. Two photons of IR light are absorbed for each excitation event. Scattering in the tissue is minimized by IR. Further, due to the multiphoton absorption, the background signal is strongly suppressed. The most commonly used fluorophores have excitation spectra in the 400-500 nm range, whereas the laser used to excite the two-photon fluorescence lies in near-IR range. If the fluorophore absorbs two infrared photons simultaneously, it will absorb enough energy to be raised into the excited state. The fluorophore will then emit a single photon with a wavelength that depends on the type of fluorophore used that can then be detected.

When a laser is used to excite fluorophores for fluorescence microscopy, sometimes this laser is the same laser that generates the laser light used to ablate material from the biological sample, but used at a power that is not sufficient to cause ablation of material from the sample. Sometimes the fluorophores are excited by the wavelength of light that the laser then ablates the sample with. In others, a different wavelength may be used, for example by generating different harmonics of the laser to obtain light of different wavelengths, or exploiting different harmonics generated in a harmonic generation system, discussed above, apart from the harmonics which are used to ablate the sample. For example, if the fourth and/or fifth harmonic of a Nd:YAG laser are used, the fundamental harmonic, or the second to third harmonics, could be used for fluorescence microscopy.

As an example technique combining fluorescence and laser ablation, it is possible to label the nuclei of cells in the biological sample with an antibody or nucleic acid conjugated to a fluorescent moiety. Accordingly, by exciting the fluorescent label and then observing and recording the positions of the fluorescence using a camera, it is possible to direct the ablating laser specifically to the nuclei, or to areas not including nuclear material. The division of the sample into nuclei and cytoplasmic regions will find particular application in field of cytochemistry. By using an image sensor (such as a CCD detector or an active pixel sensor, e.g.

a CMOS sensor), it is possible to entirely automate the process of identifying features/regions of interest and then ablating them, by using a control module (such as a computer or a programmed chip) which correlates the location of the fluorescence with the x,y coordinates of the sample and then directs the ablation laser to that location. As part of this process the first image taken by the image sensor may have a low objective lens magnification (low numerical aperture), which permits a large area of the sample to be surveyed. Following this, a switch to an objective with a higher magnification can be used to home in on the particular features of interest that have been determined to fluoresce by higher magnification optical imaging. These features recorded to fluoresce may then be ablated by a laser. Using a lower numerical aperture lens first has the further advantage that the depth of field is increased, thus meaning features buried within the sample may be detected with greater sensitivity than screening with a higher numerical aperture lens from the outset.

In methods and systems in which fluorescent imaging is used, the emission path of fluorescent light from the sample to the camera may include one or more lenses and/or one or more optical filters. By including an optical filter adapted to pass a selected spectral bandwidth from one or more of the fluorescent labels, the system is adapted to handle chromatic aberrations associated with emissions from the fluorescent labels. Chromatic aberrations are the result of the failure of lenses to focus light of different wavelengths to the same focal point. Accordingly, by including an optical filter, the background in the optical system is reduced, and the resulting optical image is of higher resolution. A further way to minimise the amount of emitted light of undesired wavelengths that reaches the camera is to exploit chromatic aberration of lenses deliberately by using a series of lenses designed for the transmission and focus of light at the wavelength transmitted by the optical filter, akin to the system explained in WO 2005/121864.

A higher resolution optical image is advantageous in this coupling of optical techniques and laser ablation sampling, because the accuracy of the optical image then determines the precision with which the ablating laser can be directed to ablate the sample.

Accordingly, in some embodiments disclosed herein, the apparatus of the invention comprises a camera. This camera can be used on-line to identify features/areas of the sample, e.g. specific cells, which can then be sampled, such as by firing a burst of pulses at the feature/region of interest to ablate sample material from the feature/region of interest. Where a burst of pulses is directed at the sample, the material in the resulting plumes detected can be as a continuous event (the plumes from each individual ablation in effect form a single plume, which is then carried on for detection). While each cloud of sample material formed from the aggregated plumes from locations within a feature/region of interest can be analysed together, sample material in plumes from each different feature/region of interest is still kept discrete. That is to say, that sufficient time is left between ablation of different features/areas of interest to allow sample material from the nth feature/area interest before ablation of the (n+1)th feature/area is begun.

In a further mode of operation combining both fluorescence analysis and laser ablation sampling, instead of analysing the entire slide for fluorescence before targeting laser ablation to those locations, it is possible to fire a pulse from the laser at a spot on the sample (at low energy so as only to excite the fluorescent moieties in the sample rather than ablate the sample) and if a fluorescent emission of expected wavelength is detected, then the sample at the spot can be ablated by firing the laser at that spot at full energy, and the resulting plume analysed by a detector as described below. This has the advantage that the rastering mode of analysis is maintained, but the speed is increased, because it is possible to pulse and test for fluorescence and obtain results immediately from the fluorescence (rather than the time taken to analyse and interpret ion data from the detector to determine if the region was of interest), again enabling only the loci of importance to be targeted for analysis. Accordingly, applying this strategy in imaging a biological sample comprising a plurality of cells, the following steps can be performed: (i) labelling a plurality of different target molecules in the sample with one or more different labelling atoms and one or more fluorescent labels, to provide a labelled sample; (ii) illuminating a known location of the sample with light to excite the one or more fluorescent labels; (iii) observing and recording whether there is fluorescence at the location; (iv) if there is fluorescence, directing laser ablation at the location, to form a plume; (v) subjecting the plume to inductively coupled plasma mass spectrometry, and (vi) repeating steps (ii)-(v) for one or more further known locations on the sample, whereby detection of labelling atoms in the plumes permits construction of an image of the sample of the areas which have been ablated.

In some instances, the sample, or the sample carrier, may be modified so as to contain optically detectable (e.g., by optical or fluorescent microscopy) moieties at specific locations. The fluorescent locations can then be used to positionally orient the sample in the apparatus. The use of such marker locations finds utility, for example, where the sample may have been examined visually "offline"—i.e. in a piece of apparatus other than the apparatus of the invention. Such an optical image can be marked with feature(s)/region(s) of interest, corresponding to particular cells by, say, a physician, before the optical image with the feature(s)/region(s) of interest highlighted and the sample are transferred to an apparatus according to the invention. Here, by reference to the marker locations in the annotated optical image, the apparatus of the invention can identify the corresponding fluorescent positions by use of the camera and calculate an ablative plan for the positions of the laser pulses accordingly. Accordingly, in some embodiments, the invention comprises an orientation controller module capable of performing the above steps.

In some instances, selection of the features/regions of interest may performed using the apparatus of the invention, based on an image of the sample taken by the camera of the apparatus of the invention.

Electron Microscope

In some embodiments of the invention, the apparatus also comprises components to perform electron microscopy.

At a general level, an electron microscope comprises an electron gun (e.g. with a tungsten filament cathode), and electrostatic/electromagnetic lenses and apertures that control the beam to direct it onto a sample in a sample chamber. The sample is held under vacuum, so that gas molecules cannot impede or diffract electrons on their way from the electron gun to the sample. In transmission electron microscopy (TEM), the electrons pass through the sample, whereupon they are deflected. The deflected electrons are then detected by a detector such as a fluorescent screen, or in some instances a high-resolution phosphor coupled to a CCD. Between the sample and the detector is an objective lens which controls the magnification of the deflected electrons on the detector.

TEM requires ultrathin sections to enable sufficient electrons to pass through the sample such that an image may be reconstructed from the deflected electrons that hit the detector. Typically, TEM samples are 100 nm or thinner, as prepared by use of an ultramicrotome. Biological tissue specimens are chemically fixed, dehydrated and embedded in a polymer resin to stabilize them sufficiently to allow the ultrathin sectioning. Sections of biological specimens, organic polymers and similar materials may require staining with heavy atom labels in order to achieve the required image contrast, as unstained biological samples in their native unstained state rarely interact strongly with electrons, so as to deflect them to allow electron microscopy images to be recorded.

As noted above, when thin sections are used, it is possible to perform electron microscopy on a sample also analysed by IMS or IMC. Accordingly, high resolution structural images can be obtained by electron microscopy, for example transmission electron microscopy, and then this high resolution image used to refine the resolution of image data obtained by IMS or IMC to a resolution beyond that achievable with ablation using laser radiation (due to the much shorter wavelength of electrons compared to photons). In some instances, both electron microscopy and elemental analysis by IMC or IMS are performed on the sample in a single apparatus (as IMC/IMS are destructive processes, electron microscopy is performed prior to IMC/IMS)

Thus, the invention provides an imaging mass cytometer or imaging mass spectrometer as described herein further comprising an electron microscope, such as comprising components as set out above, e.g. an electron source, such as an electron gun. As will be understood by one of skill in the art, the particular arrangement of the components will vary (e.g. direction from which electrons are directed onto the sample and the direction from which laser radiation is directed onto the sample), and routine arrangement of components can be achieved without undue burden. In some instances, the sample is not moved within the apparatus between analysis by electron microscopy and subsequent ablation. As the person of skill in the art will understand, electron microscopy is performed under a vacuum, but ablation as discussed in this section is performed in the presence of a flow of gas that entrains particulate material in the plume generated by ablation of the sample. Accordingly, after completion of the electron microscopy stage of analysis, the sample chamber will be allowed to return to closer to atmospheric pressure before elemental analysis is performed.

In ICP and IMS apparatus comprising an electron microscope, the arrangement of components may be such that laser radiation for ablation is directed to the sample through the sample carrier, e.g. as in FIG. 3 or 4, the sample carrier can act as part of the wall of the sample chamber, allowing the sample chamber to be kept under vacuum, for electron microscopy purposes. Accordingly, in some embodiments herein, the apparatus comprises an electron microscope and an immersion medium, such as a liquid immersion lens or a solid immersion lens.

Laser Ablation

Laser ablation may be performed in a manner as set out previously, for example in Giesen et al, 2014 and WO2014169394, in light of the modifications related herein (e.g. it is not mandatory to use an ICP to ionize the sample material, nor to use a TOF MS detector). For example, methods and systems for ionization at or near the sample surface, as described herein, may use ion optics to transfer labelling atoms to a mass spectrometry detector (e.g., a TOF detector or magnetic sector detector) directly from the sample, without the need of gas fluidics to deliver sample to an ICP. In some cases, methods and systems may use non-laser forms of radiation (e.g., an electron beam, or ion beam) instead of, or in addition to, a laser.

In embodiments where laser ablation is performed without sustained ionization of the ablated sample, the ablation plume may be transferred to an ICP-MS as described below.

Transfer Conduit

The transfer conduit forms a link between the laser ablation sampling system and the ionisation system, and allows the transportation of plumes of sample material, generated by the laser ablation of the sample, from the laser ablation sampling system to the ionisation system. Part (or all) of the transfer conduit may be formed, for example, by drilling through a suitable material to produce a lumen (e.g., a lumen with a circular, rectangular or other cross-section) for transit of the plume. The transfer conduit sometimes has an inner diameter in the range 0.2 mm to 3 mm. Sometimes, the internal diameter of the transfer conduit can be varied along its length. For example, the transfer conduit may be tapered at an end. A transfer conduit sometimes has a length in the range of 1 centimeter to 100 centimeters. Sometimes the length is no more than 10 centimeters (e.g., 1-10 centimeters), no more than 5 centimeters (e.g., 1-5 centimeters), or no more than 3 cm (e.g., 0.1-3 centimeters). Sometimes the transfer conduit lumen is straight along the entire distance, or nearly the entire distance, from the ablation system to the ionisation system. Other times the transfer conduit lumen is not straight for the entire distance and changes orientation. For example, the transfer conduit may make a gradual 90 degree turn. This configuration allows for the plume generated by ablation of a sample in the laser ablation sampling system to move in a vertical plane initially while the axis at the transfer conduit inlet will be pointing straight up, and move horizontally as it approaches the ionisation system (e.g. an ICP torch which is commonly oriented horizontally to take advantage of convectional cooling). The transfer conduit can be straight for a distance of least 0.1 centimeters, at least 0.5 centimeters or at least 1 centimeter from the inlet aperture though which the plume enters or is formed. In general terms, typically, the transfer conduit is adapted to minimize the time it takes to transfer material from the laser ablation sampling system to the ionisation system.

Transfer Conduit Inlet, Including Sample Cone

The transfer conduit comprises an inlet in the laser ablation sampling system (in particular within the sample chamber of the laser ablation sampling system; it therefore also represents the principal gas outlet of the sample chamber). The inlet of the transfer conduit receives sample material ablated from a sample in the laser ablation sampling system, and transfers it to the ionisation system. In some instances, the laser ablation sampling system inlet is the source of all gas flow along the transfer conduit to the ionisation system. In some instances, the laser ablation sampling system inlet that receives material from the laser ablation sampling system is an aperture in the wall of a conduit along which a second "transfer" gas is flowed (as disclosed, for example in WO2014146724 and WO2014147260) from a separate transfer flow inlet. In this instance, the transfer gas forms a significant proportion, and in many instances the majority of the gas flow to the ionisation system. The sample chamber of the laser ablation sampling system contains a gas inlet. Flowing gas into the chamber through this inlet creates a flow of gas out of the chamber though the inlet of the transfer conduit. This flow of gas captures plumes of ablated material, and entrains it as it into the transfer conduit (typically the laser ablation sampling system inlet of the transfer conduit is in the shape of a cone, termed herein the sample cone) and out of the sample chamber into the conduit passing above the chamber. This conduit also has gas flowing into it from the separate transfer flow inlet (left hand side of the figure, indicated by the transfer flow arrow). The component comprising the transfer flow inlet, laser ablation sampling system inlet and which begins the transfer conduit which carries the ablated sample material towards the ionisation system can also termed a flow cell (as it is in WO2014146724 and WO2014147260).

The transfer flow fulfils at least three roles: it flushes the plume entering the transfer conduit in the direction of the ionisation system, and prevents the plume material from contacting the side walls of the transfer conduit; it forms a "protection region" above the sample surface and ensures that the ablation is carried out under a controlled atmosphere; and it increases the flow speed in the transfer conduit. Usually, the viscosity of the capture gas is lower than the viscosity of the transfer gas. This helps to confine the plume of sample material in the capture gas in the center of the transfer conduit and to minimize the diffusion of the plume of sample material downstream of the laser ablation sampling system (because in the center of the flow, the transport rate is more constant and nearly flat). The gas(es) may be, for example, and without limitation, argon, xenon, helium, nitrogen, or mixtures of these. A common transfer gas is argon. Argon is particularly well-suited for stopping the diffusion of the plume before it reaches the walls of the transfer conduit (and it also assists improved instrumental sensitivity in apparatus where the ionisation system is an argon gas-based ICP). The capture gas is preferably helium. However, the capture gas may be replaced by or contain other gases, e.g., hydrogen, nitrogen, or water vapor. At 25° C., argon has a viscosity of 22.6 µPas, whereas helium has a viscosity of 19.8 µPas. Sometimes, the capture gas is helium and the transfer gas is argon.

As described in WO2014169394, the use of a sample cone minimizes the distance between the target and the laser ablation sampling system inlet of the transfer conduit. Because of the reduced distance between the sample and the point of the cone through which the capture gas can flow cone, this leads to improved capture of sample material with less turbulence, and so reduced spreading of the plumes of ablated sample material. The inlet of the transfer conduit is therefore the aperture at the tip of the sample cone. The cone projects into the sample chamber.

An optional modification of the sample cone is to make it asymmetrical. When the cone is symmetrical, then right at the center the gas flow from all directions neutralizes, so the overall flow of gas is zero along the surface of the sample at the axis of the sample cone. By making the cone asymmetrical, a non-zero velocity along the sample surface is created, which assists in the washout of plume materials from the sample chamber of the laser ablation sampling system.

In practice, any modification of the sample cone that causes a non-zero vector gas flow along the surface of the sample at the axis of the cone may be employed. For instance, the asymmetric cone may comprise a notch or a series of notches, adapted to generate non-zero vector gas flow along the surface of the sample at the axis of the cone. The asymmetric cone may comprise an orifice in the side of the cone, adapted to generate non-zero vector gas flow along the surface of the sample at the axis of the cone. This orifice will imbalance gas flows around the cone, thereby again generating a non-zero vector gas flow along the surface of the sample at the axis of the cone at the target. The side of the cone may comprise more than one orifice and may include both one or more notches and one or more orifices. The edges of the notch(es) and/or orifice(s) are typically smoothed, rounded or chamfered in order to prevent or minimize turbulence.

Different orientations of the asymmetry of the cone will be appropriate for different situations, dependent on the choice of capture and transfer gas and flow rates thereof, and it is within the abilities of the skilled person to appropriately identify the combinations of gas and flow rate for each orientation.

All of the above adaptations may be present in a single asymmetric sample cone as use in the invention. For example, the cone may be asymmetrically truncated and formed from two different elliptical cone halves, the cone may be asymmetrically truncated and comprise one of more orifices and so on.

The sample cone is therefore adapted to capture a plume of material ablated from a sample in the laser ablation sampling system. In use, the sample cone is positioned operably proximate to the sample, e.g. by manoeuvring the sample within the laser ablation sampling system on a movable sample carrier tray, as described already above. As noted above, plumes of ablated sample material enter the transfer conduit through an aperture at the narrow end of the sample cone. The diameter of the aperture can be a) adjustable; b) sized to prevent perturbation to the ablated plume as it passes into the transfer conduit; and/or c) about the equal to the cross-sectional diameter of the ablated plume.

Tapered Conduits

In tubes with a smaller internal diameter, the same flow rate of gas moves at a higher speed. Accordingly, by using a tube with a smaller internal diameter, a plume of ablated sample material carried in the gas flow can be transported across a defined distance more rapidly at a given flow rate (e.g. from the laser ablation sampling system to the ionisation system in the transfer conduit). One of the key factors in how quickly an individual plume can be analysed is how much the plume has diffused during the time from its generation by ablation through to the time its component ions are detected at the mass spectrometer component of the apparatus (the transience time at the detector). Accordingly, by using a narrow transfer conduit, the time between ablation and detection is reduced, thereby meaning diffusion is decreased because there is less time in which it can occur, with the ultimate result that the transience time of each ablation plume at the detector is reduced. Lower transience times mean that more plumes can be generated and analyzed per unit time, thus producing images of higher quality and/or faster.

The taper may comprise a gradual change in the internal diameter of the transfer conduit along said portion of the length of the transfer conduit (i.e. the internal diameter of the tube were a cross section taken through it decreases along the portion from the end of the portion towards the inlet (at the laser ablation sampling system end) to the outlet (at the ionisation system end). Usually, the region of the conduit near where ablation occurs has a relatively wide internal diameter. The larger volume of the conduit before the taper facilitates the confinement of the materials generated by ablation. When the ablated particles fly off from the ablated spot they travel at high velocities. The friction in the gas slows these particles down but the plume can still spread on a sub-millimeter to a millimeter scale. Allowing for sufficient distances to the walls helps with the containment of the plume near the center of the flow.

Because the wide internal diameter section is only short (of the order of 1-2 mm), it does not contribute significantly to the overall transience time providing the plume spends more time in the longer portion of the transfer conduit with a narrower internal diameter. Thus, a larger internal diameter portion is used to capture the ablation product and a smaller internal diameter conduit is used to transport these particles rapidly to the ionisation system.

The diameter of the narrow internal diameter section is limited by the diameter corresponding to the onset of turbulence. A Reynolds number can be calculated for a round tube and a known flow. In general a Reynolds number above 4000 will indicate a turbulent flow, and thus should be avoided. A Reynolds number above 2000 will indicate a transitional flow (between non-turbulent and turbulent flow), and thus may also be desired to be avoided. For a given mass flow of gas the Reynolds number is inversely proportional to the diameter of the conduit. The internal diameter of the narrow internal diameter section of the transfer conduit commonly is narrower than 2 mm, for example narrower than 1.5 mm, narrower than 1.25 mm, narrower than 1 mm, but greater than the diameter at which a flow of helium at 4 liters per minute in the conduit has a Reynolds number greater than 4000.

Rough or even angular edges in the transitions between the constant diameter portions of the transfer conduit and the taper may cause turbulence in the gas flow, and typically are avoided.

Sacrificial Flow

At higher flows, the risk of turbulence occurring in the conduit increases. This is particularly the case where the transfer conduit has a small internal diameter (e.g. 1 mm). However, it is possible to achieve high speed transfer (up to and in excess of 300 m/s) in transfer conduits with a small internal diameter if a light gas, such as helium or hydrogen, is used instead of argon which is traditionally used as the transfer flow of gas.

High speed transfer presents problems insofar as it may cause the plumes of ablated sample material to be passed through the ionisation system without an acceptable level of ionisation occurring. The level of ionisation can drop because the increased flow of cool gas reduces the temperature of the plasma at the end of the torch. If a plume of sample material is not ionised to a suitable level, information is lost from the ablated sample material—because its components (including any labelling atoms/elemental tags) cannot be detected by the mass spectrometer. For example, the sample may pass so quickly through the plasma at the end of the torch in an ICP ionisation system that the plasma ions do not have sufficient time to act on the sample material to ionise it. This problem, caused by high flow, high speed transfer in narrow internal diameter transfer conduits can be solved by the introduction of a flow sacrificing system at the outlet of the transfer conduit. The flow sacrificing system is adapted to receive the flow of gas from the transfer conduit, and pass only a portion of that flow (the central portion of the flow comprising any plumes of ablated sample material) onwards into the injector that leads to the ionisation system. To facilitate dispersion of gas from the transfer conduit in the flow sacrificing system, the transfer conduit outlet can be flared out.

The flow sacrificing system is positioned close to the ionisation system, so that the length of the tube (e.g. injector) that leads from the flow sacrificing system to the ionisation system is short (e.g. ~1 cm long; compared to the length of the transfer conduit which is usually of a length of the order of tens of cm, such as ~50 cm). Thus the lower gas velocity within the tube leading from the flow sacrificing system to the ionisation system does not significantly affect the total transfer time, as the relatively slower portion of the overall transport system is much shorter.

In most arrangements, it is not desirable, or in some cases possible, to significantly increase the diameter of the tube (e.g. the injector) which passes from the flow sacrificing system to the ionisation system as a way of reducing the speed of the gas at a volumetric flow rate. For example, where the ionisation system is an ICP, the conduit from the flow sacrificing system forms the injector tube in the center of the ICP torch. When a wider internal diameter injector is used, there is a reduction in signal quality, because the plumes of ablated sample material cannot be injected so precisely into the center of the plasma (which is the hottest and so the most efficiently ionising part of the plasma). The strong preference is for injectors of 1 mm internal diameter, or even narrower (e.g. an internal diameter of 800 µm or less, such as 600 µm or less, 500 µm or less or 400 µm or less). Other ionisation techniques rely on the material to be ionised within a relatively small volume in three dimensional space (because the necessary energy density for ionisation can only be achieved in a small volume), and so a conduit with a wider internal diameter means that much of the sample material passing through the conduit is outside of the zone in which energy density is sufficient to ionise the sample material. Thus narrow diameter tubes from the flow sacrificing system into the ionisation system are also employed in apparatus with non-ICP ionisation systems. As noted above, if a plume of sample material is not ionised to a suitable level, information is lost from the ablated sample material—because its components (including any labelling atoms/elemental tags) cannot be detected by the mass spectrometer.

Pumping can be used to help ensure a desired split ratio between the sacrificial flow and the flow passing into the inlet of the ionisation system. Accordingly, sometimes, the flow sacrificing system comprises a pump attached to the sacrificial flow outlet. A controlled restrictor can be added to the pump to control the sacrificial flow. Sometimes, the flow sacrificing system also comprises a mass flow controller, adapted to control the restrictor.

Where expensive gases are used, the gas pumped out of the sacrificial flow outlet can be cleaned up and recycled back into the same system using known methods of gas purification. Helium is particularly suited as a transport gas as noted above, but it is expensive; thus, it is advantageous to reduce the loss of helium in the system (i.e. when it is passed into the ionisation system and ionised). Accordingly, sometimes a gas purification system is connected to the sacrificial flow outlet of the flow sacrificing system.

Ionisation System

In order to generate elemental ions, it is necessary to use a hard ionisation technique that is capable of vaporising, atomising and ionising the atomised sample.

Inductively Coupled Plasma Torch

Commonly, an inductively coupled plasma is used to ionise the material to be analysed before it is passed to the mass detector for analysis. It is a plasma source in which the energy is supplied by electric currents produced by electromagnetic induction. The inductively coupled plasma is sustained in a torch that consists of three concentric tubes, the innermost tube being known as the injector.

The induction coil that provides the electromagnetic energy that maintains the plasma is located around the output end of the torch. The alternating electromagnetic field reverses polarity many millions of times per second. Argon gas is supplied between the two outermost concentric tubes. Free electrons are introduced through an electrical discharge and are then accelerated in the alternating electromagnetic field whereupon they collide with the argon atoms and ionise them. At steady state, the plasma consists of mostly of argon atoms with a small fraction of free electrons and argon ions.

The ICP can be retained in the torch because the flow of gas between the two outermost tubes keeps the plasma away from the walls of the torch. A second flow of argon introduced between the injector (the central tube) and the intermediate tube keeps the plasma clear of the injector. A third flow of gas is introduced into the injector in the centre of the torch. Samples to be analysed are introduced through the injector into the plasma.

The ICP can comprise an injector with an internal diameter of less than 2 mm and more than 250 µm for introducing material from the sample into the plasma. The diameter of the injector refers to the internal diameter of the injector at the end proximal to the plasma. Extending away from the plasma, the injector may be of a different diameter, for example a wider diameter, wherein the difference in diameter is achieved through a stepped increase in diameter or because the injector is tapered along its length. For instance, the internal diameter of the injector can be between 1.75 mm and 250 µm, such as between 1.5 mm and 300 µm in diameter, between 1.25 mm and 300 µm in diameter, between 1 mm and 300 µm in diameter, between 900 µm and 300 µm in diameter, between 900 µm and 400 µm in diameter, for example around 850 µm in diameter. The use of an injector with an internal diameter less than 2 mm provides significant advantages over injectors with a larger diameter. One advantage of this feature is that the transience of the signal detected in the mass detector when a plume of sample material is introduced into the plasma is reduced with a narrower injector (the plume of sample material being the cloud of particular and vaporous material removed from the sample by the laser ablation sampling system). Accordingly, the time taken to analyse a plume of sample material from its introduction into the ICP for ionisation until the detection of the resulting ions in the mass detector is reduced. This decrease in time taken to analyse a plume of sample material enables more plumes of sample material to be detected in any given time period. Also, an injector with a smaller internal diameter results in the more accurate introduction of sample material into the centre of the induction coupled plasma, where more efficient ionisation occurs (in contrast to a larger diameter injector which could introduce sample material more towards the fringe of the plasma, where ionisation is not as efficient). ICP torches (Agilent, Varian, Nu Instruments, Spectro, Leeman Labs, PerkinElmer, Thermo Fisher etc.) and injectors (for example from Elemental Scientific and Meinhard) are available.

Other Ionisation Techniques

Electron Ionisation

Electron ionisation involves bombarding a gas-phase sample with a beam of electrons. An electron ionisation chamber includes a source of electrons and an electron trap. A typical source of the beam of electrons is a rhenium or tungsten wire, usually operated at 70 electron volts energy. Electron beam sources for electron ionisation are available from Markes International. The beam of electrons is directed towards the electron trap, and a magnetic field applied parallel to the direction of the electrons travel causes the electrons to travel in a helical path. The gas-phase sample is directed through the electron ionisation chamber and interacts with the beam of electrons to form ions. Electron ionisation is considered a hard method of ionisation since the process typically causes the sample molecules to fragment. Examples of commercially available electron ionisation systems include the Advanced Markus Electron Ionisation Chamber.

Optional Further Components of the Laser Ablation Based Sampling and Ionisation System Ion Deflector Mass spectrometers detect ions when they hit a surface of their detector. The collision of an ion with the detector causes the release of electrons from the detector surface. These electrons are multiplied as they pass through the detector (the first released electron knocks out further electrons in the detector, these electrons then hit secondary plates which further amplify the number of electrons). The number of electrons hitting the anode of the detector generates a current. The number of electrons hitting the anode can be controlled by altering the voltage applied to the secondary plates. The current is an analog signal that can then be converted into a count of the ions hitting the detector by an analog-digital converter. When the detector is operating in its linear range, the current can be directly correlated to the number of ions. The quantity of ions that can be detected at once has a limit (which can be expressed as the number of ions detectable per second). Above this point, the number electrons released by ions hitting the detector is no longer correlated to the number of ions. This therefore places an upper limit on the quantitative capabilities of the detector.

When ions hit the detector, its surface becomes damaged by contamination. Over time, this irreversible contamination damage results in fewer electrons being released by the detector surface when an ion hits the detector, with the ultimate result that the detector needs replacing. This is termed "detector aging", and is a well-known phenomenon in MS.

Detector life can therefore be lengthened by avoiding the introduction of overloading quantities of ions into the MS. As noted above, when the total number of ions hitting the MS detector exceeds the upper limit of detection, the signal is not as informative as when the number of ions is below the upper limit because it is no longer quantitative. It is therefore desirable to avoid exceeding the upper limit of detection as it results in accelerated detector aging without generating useful data.

Analysis of large packets of ions by mass spectrometry involves a particular set of challenges not found in normal mass spectrometry. In particular, typical MS techniques involve introducing a low and constant level of material into the detector, which should not approach the upper detection limit or cause accelerated aging of the detector. On the other hand, laser ablation-based techniques analyse a relatively large amount of material in a very short time window in the MS: e.g. the ions from a cell-sized patch of a tissue sample which is much larger than the small packets of ions typically analysed in MS. In effect, it is a deliberate almost overloading of the detector with analysed packed of ions resulting from ablation or lifting. In between the analysis events the signal is at baseline (a signal that is close to zero because no ions from labelling atoms are deliberately being entering into the MS from the sampling and ionisation system; some ions will inevitably be detected because the MS is not a complete vacuum).

Thus in apparatus described herein, there is an elevated risk of accelerated detector aging, because the ions from packets of ionised sample material labelled with a large number of detectable atoms can exceed the upper limit of detection and damage the detector without providing useful data.

To address these issues, the apparatus can comprise an ion deflector positioned between the sampling and ionisation system and the detector system (a mass spectrometer), operable to control the entry of ions into the mass spectrometer. In one arrangement, when the ion deflector is on, the ions received from the sampling and ionisation system are deflected (i.e. the path of the ions is changed and so they do not reach the detector), but when the deflector is off the ions are not deflected and reach the detector. How the ion deflector is deployed will depend on the arrangement of the sampling and ionisation system and MS of the apparatus. E.g. if the portal through which the ions enter the MS is not directly in line with the path of ions exiting the sampling and ionisation system, then by default the appropriately arranged ion deflector will be on, in order to direct ions from the sampling and ionisation system into the MS. When an event resulting from the ionisation a packet of ionised sample material considered likely to overload the MS is detected (see below), the ion deflector is switched off, so that the rest of the ionised material from the event is not deflected into the MS and can instead simply hit an internal surface of the system, thereby preserving the life of the MS detector. The ion deflector is returned to its original state after the ions from the damaging event have been prevented from entering the MS, thereby allowing the ions from subsequent packets of ionised sample material to enter the MS and be detected.

Alternatively, in arrangements where (under normal operating conditions) there is no change in the direction of the ions emerging from the sampling and ionisation system before they enter the MS the ion deflector will be off, and the ions from the sampling and ionisation system will pass through it to be analysed in the MS. To prevent damage when a potential overload of the detector is detected, in this configuration the ion deflector is turned on, and so diverts ions so that they do not enter the detector in order to prevent damage to the detector.

The ions entering the MS from ionisation of sample material (such as a plume of material generated by laser ablation) do not enter the MS all at the same time, but instead enter as a peak with a frequency that follows a probability distribution curve about a maximum frequency: from baseline, at first a small number of ions enters the MS and are detected, and then the frequency of ions increases to a maximum before the number decreases again and trails off to baseline. An event likely to damage the detector can be identified because instead of a slow increase in the frequency of ions at the leading edge of the peak, there is a very quick increase in counts of ions hitting the detector.

The flow of ions hitting the detector of a TOF MS, a particular type of detector as discussed below, is not continual during the analysis of the ions in a packet of ionised sample material. The TOF comprises a pulser which releases the ions periodically into the flight chamber of the TOF MS in pulsed groups. By releasing the ions all at the known same time, the time of flight mass determination is enabled. The time between the releases of pulses of ions for time of flight mass determination is known as an extraction or push of the TOF MS. The push is in the order of microseconds. The signal from one or more packets of ions from the sampling and ionisation system therefore covers a number of pushes.

Accordingly, when the ion count reading jumps from the baseline to a very high count within one push (i.e. the first portion of the ions from a particular packet of ionised sample material) then it can be predicted that the main body of ions resulting from ionisation of the packet of sample material will be even greater, and so exceed the upper detection limit. It is at this point that an ion deflector can be operated to ensure that the damaging bulk of the ions are directed away from the detector (by being activated or deactivated, depending on the arrangement of the system, as discussed above).

Suitable ion deflectors based on quadrupoles are available in the art (e.g. from Colutron Research Corporation and Dreebit GmbH).

Laser Ablation-Based Sampling Systems of the Invention

The components of the laser ablation-based sampling systems can be combined as appropriate for the analytical task being undertaken. Exemplary embodiments are set out below.

In some embodiments, the laser ablation-based sampling system for analysing a sample, such as a biological sample, comprises:
  a sample stage;
  a laser source;
  a laser scanning system; and
  focusing optics comprising an objective lens, wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
  a sample stage;
  a laser source comprising a femtosecond laser;
  a laser scanning system; and
  focusing optics comprising an objective lens, wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
  a sample stage comprising a first face and a second face, the first and second faces being opposed, and wherein the first face is adapted to receive a sample;
  a laser source;
  a laser scanning system; and
  focusing optics comprising an objective lens, the focusing optics adapted to direct a beam of radiation from the laser source towards the second face to a location on the sample stage; and wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
  a sample stage comprising a first face and a second face, the first and second faces being opposed, and wherein the first face is adapted to receive a sample;
  a laser source comprising a femtosecond laser;
  a laser scanning system; and
  focusing optics comprising an objective lens, the focusing optics adapted to direct a beam of radiation from the laser source towards the second face to a location on the sample stage; and wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
a sample stage comprising a first face and a second face, the first and second faces being opposed, and wherein the first face is adapted to receive a sample;
a laser source; and
focusing optics comprising an objective lens, the focusing optics adapted to direct a beam of radiation from the laser source towards the second face to a location on the sample stage; and wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
a sample stage comprising a first face and a second face, the first and second faces being opposed, and wherein the first face is adapted to receive a sample;
a laser source comprising a femtosecond laser; and
focusing optics comprising an objective lens, the focusing optics adapted to direct a beam of radiation from the laser source towards the second face to a location on the sample stage; and wherein the objective lens has a numerical aperture of at least 0.7, at least 0.8 or at least 0.9, optionally further comprising an immersion medium between the objective lens and the sample stage.

In some embodiments, the laser ablation-based sampling system for analysing a sample, such as a biological sample, comprises:
a sample stage comprising a first face and a second face, the first and second faces being opposed, and wherein the first face is adapted to receive a sample;
a laser source;
a laser scanning system; and
focusing optics comprising an objective lens, optionally further comprising an immersion medium between the objective lens and the sample stage.

In some embodiments, the laser ablation-based sampling system for analysing a sample, such as a biological sample, comprises:
a sample stage comprising a first face and a second face, the first and second faces being opposed, and wherein the first face is adapted to receive a sample;
a laser source comprising a femtosecond laser;
a laser scanning system; and
focusing optics comprising an objective lens, optionally further comprising an immersion medium between the objective lens and the sample stage.

In some embodiments, the laser ablation-based sampling system for analysing a sample, such as a biological sample, comprises:
a sample stage comprising a first face and a second face, the first and second faces being opposed, and wherein the first face is adapted to receive a sample;
a laser source comprising a femtosecond laser; and
focusing optics comprising an objective lens, optionally further comprising an immersion medium between the objective lens and the sample stage.

Each of the laser ablation-based sampling systems set out above are suitable for inclusion in an apparatus of the invention for analysing a sample, comprising a mass detector (e.g. a TOF) mass detector, in particular comprising an ICP ionisation system.

b. Sputtering Based Sampling and Ionising System

Sputtering based sampling systems and techniques provide alternative surface analysis techniques to the laser ablation-based systems and techniques described above. One such sputtering technique is Secondary Ion Mass Spectrometry (SIMS). SIMS involves bombarding a sample with a focused ion beam to sputter material from the sample. The sputtered material comprises both ions and neutral atoms. In SIMS, the ions are then transferred to a mass detector in a vacuum following capture by an immersion lens. The mass detector can be any of the mass detector systems described below. Similar sputtering can be achieved by direction of other charged particles at the sample, for instance electrons.

SIMS is a useful surface analysis technique for several reasons. Firstly, the technique is very sensitive to low concentrations of analyte material. Secondly, because diffraction effects of primary ions can be neglected for most practical conditions, there is virtually no diffraction limit in SIMS. Thus, SIMS has the potential to analyse material on the scale of 10 to 30 nm.

However, the ionisation efficiency for the sputtered material is very low and ionisation is also very dependent on the surface chemistry and specific element being ionised, hence, the number of ions produced by SIMS is not always sufficient to provide a sufficient signal-to-noise ratio. For instance, an ionization efficiency is insufficient for detection of single copies of antibodies labelled with MaxPar reagents. Since a single antibody labelled with MaxPar mass tag carries about 100 atoms approximately 100 copies of antibodies may be required to generate a signal that is larger than a few ions at the detector in a traditional SIMS workflow. Yet another deficiency of SIMS is due to spectral interferences from molecules in the same mass channels and due to formations of compound ions such as oxides and other species involving primary tagging elements and abundant neutral atoms present in biological samples. The compound ions dilute the signal of the elemental ions and cause an overlap with mass channels of higher mass elements. Thus, the resolution of imaging using SIMS can be limited by low sensitivity of detection due in part to low ionization efficiency.

The present invention overcomes the limitations of SIMS by providing improved methods and apparatus for analysing a biological sample using laser-based Secondary Neutral Mass Spectrometry (SNMS).

The Laser-SNMS method and apparatus of the present invention involve bombarding a sample with a focused charged particle beam to sputter material from the sample. A laser is used to post-ionise the neutral sputtered material. These ejected ions (including any detectable ions from labelling atoms as discussed below) can be detected by a detector system for instance a mass spectrometer (detectors are discussed in more detail below). Since the majority of sputtered material is in the neutral state and SNMS ionises sputtered material so that it can be analysed using mass detectors, SNMS provides a better quantitative estimation of the surface than SIMS. Furthermore, as discussed above, one of the main challenges in improving the spatial resolution of traditional IMS and IMC is ensuring that the amount of analyte in the material analysed provides a sufficient signal-to-noise ratio. Therefore, because SNMS makes use of both neutral and ionised sputtered material, SNMS based IMC and IMS provide increased resolution compared to SIMS based IMC and IMS. For instance, SNMS can enable single copy detection with antibodies tagged by MaxPar reagents. For instance, if efficiency of postionization reaches 10% then 100 atoms per each antibody would result in 10 ions produced per antibody and if these ions are carried to the detector with good efficiency this would ensure a confident detection of each copy of antibody.

Figure 6:
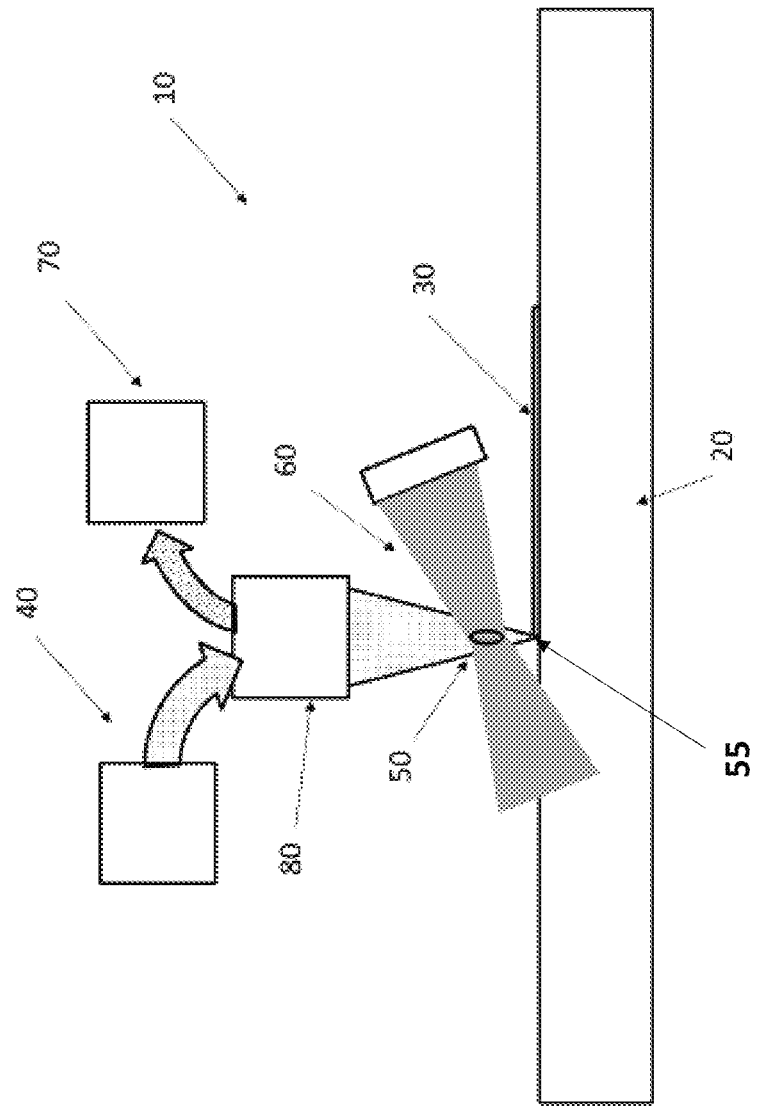
FIG. 6 is a schematic diagram of the optics arrangement of an apparatus for analysing a biological sample using laser post-ionisation.
Figure 7:
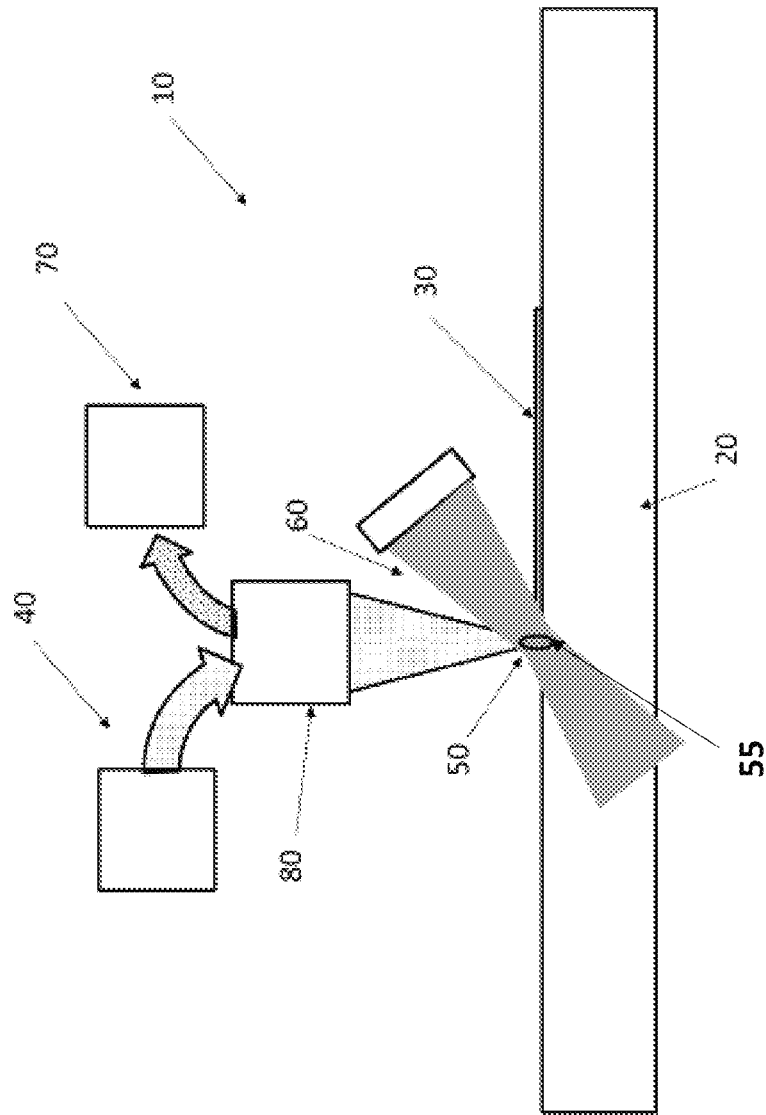
FIG. 7 is a schematic diagram of the optics arrangement of an apparatus for analysing a biological sample using laser pumping of the sample.

A laser-SNMS system typically comprises three components. The first component is a source of charged particles for sputtering material from the sample for analysis (this source of charged particles is discussed in more detail below). The second component is a laser for post-ionising the sputtered material. The third component is a detector component that detects the ionised material, for instance a mass detector. In laser-SNMS, the laser and charged particle source are typically pulsed. In a related system, the first component is a source of charged particles for directed at a location on the sample (this source of charged particles is discussed in more detail below). The second component is a laser for causing ablation and optionally ionization of the locus at which has been preseeded with electrons by the charged particles. The third component is a detector component that detects the ionised material, for instance a mass detector. In certain aspects, the spot size of the charged particles impinging the sample is smaller than the spot size of the laser. The charged particles may ablate sample at the location, after which the laser may ionize sample near the sample surface (e.g., as shown in FIG. 6). The charged particles may seed electrons at the location of the sample, after which the laser may ablate and ionize sample that was seeded with electrons (e.g., as shown in FIG. 7). The laser may ionize the sample within picoseconds (e.g., 10-100 ps) of the charged particles impinging the sample (e.g., within the charge-ignition state). In certain aspects, the spot size of the charged particles impinging the sample is smaller than the spot size of the laser, such as less than one half, less than one fifth, less than one tenth, less than one twentieth, or less than one hundredth the size of the laser spot size. For example, the laser may have a spot size (impinging the sample) of less than 10 micrometres and/or more than 500 nanometres, such as between 500 nanometers and 5 micrometers, between 800 nm and 2 micrometer, or around 1 micrometer. The charged particles may provide a small spot size (e.g., in the range described herein) to allow ionization with minimal neutralization upon laser radiation, such as with a spot size less than 200 nm, less than 100 nm, less than 50 nm, less than 30 nm, or less than 10 nm in diameter.

Accordingly, the invention provides an apparatus for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage.

The apparatus typically comprises a mass detector, such as a TOF detector.

Accordingly, the invention provides a sampling and ionisation system for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage.

The charged particle column of the present invention includes appropriate ion optics arranged to focus the charged particles in order to pass the beam to a location on the sample stage. Such appropriate ion optics can include a mass filter, lenses and apertures and deflection plates in order to shape the primary ion beam, as described in more detail below.

FIG. 6 is a schematic diagram of the arrangement of an exemplary embodiment of the invention. The energy source 40 emits radiation (e.g. a laser beam, primary ion beam, or an electron beam, as discussed further below) which is passed towards a location 55 on the sample stage 20 by optics 80 (e.g., light optics or ion optics, such as a charged particle column). The sample 30 is positioned on sample stage 20 such the charged particles passed towards location 55 sputter material 50 from the sample 30. A first laser source 60 emits a laser beam and focusing optics (not shown) direct the laser beam towards the sample stage to ionise the sputtered material 50, forming a plume of material comprising sample ions. The ions can then be transferred to a mass detector, for example a time of flight detector or magnetic sector detector, or any other mass detector which is discussed in more detail below.

Accordingly, the invention provides an apparatus or sampling and ionisation system for analysing a sample, such as a biological sample, wherein the first focusing optics is configured to synchronise a pulse of laser beam to ionise a plume of material sputtered by a pulse of charged particles (termed herein post-ionisation).

Accordingly, the invention provides an apparatus for analysing a sample, such as a biological sample, comprising:
a sample stage;
a source of charged particles and a charged particle column for passing a beam of charged particles to a location on the sample stage;
a first laser source and first focusing optics configured to direct a laser beam emitted by the first laser source towards the sample stage, wherein the first focusing optics is configured to synchronise a pulse of laser beam to ionise a plume of material sputtered by a pulse of charged particles from the source of charged particles.

In particular, the first focussing optics direct and focus the laser beam to a volume above the surface of the sample stage, such that when material is sputtered from a sample on the sample stage, the plume of material which is ejected from the sample passes into the volume to which the radiation of the first laser source is focussed, such that the material can be ionized. This explanation applies to all apparatus discussed below in this section using the combination of features of a sample stage, source of charged particles and first laser source and first focussing optics that ionise plume. It is merely not repeated each time below in the interests of brevity.

The apparatus typically comprises a mass detector, such as a TOF detector.

Accordingly, the invention provides a sampling and ionisation system for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage, wherein the first focusing optics is configured to synchronise a pulse of laser beam to ionise a plume of material sputtered by a pulse of charged particles from the source of charged particles.

As explained above, the first focussing optics direct and focus the laser beam to a volume above the location on the sample stage (more specifically above the location on a sample on the sample stage), such that when material is sputtered from a sample on the sample stage, the plume of material which is ejected from the sample passes into the volume to which the radiation of the first laser source is focussed, such that the material can be ionized. This explanation applies to all systems discussed below in this section using the combination of features of a sample stage, source of charged particles and first laser source and first focussing optics that ionise plume. It is merely not repeated each time below in the interests of brevity.

FIG. 7 is a schematic diagram of the arrangement of a further exemplary embodiment of the invention. FIG. 7 includes elements in common with FIG. 6 and these elements share the same reference numeral. However, in the apparatus of the embodiment shown in FIG. 7, the laser beam from first laser source 60 is directed towards the location 55 on the sample stage 20 at which the optics 80 (e.g., charged particle column) is directed. For example, a pulse of the charged particles passed towards the location 55 on the sample forms an excited state with free electrons at the location 55 on the sample; this excited state is referred to herein as the 'sample ignition state'. The laser beam from the first laser source illuminates the location 55 on the sample directly after the pulse of charged particles arrives at the location so that the first laser source illuminates the sample in the ignition state. Because the sample is in the sample ignition state, the sample readily converts the pulse of laser light from the laser beam into ablation and ionisation energy; this state is referred to herein as the 'sample energy pumping state'. This process forms a plume of material comprising sample ions. The skilled person would understand that the energy of the laser pulse in this embodiment is less than the ablation threshold of the specimen (such that areas of the same neighbouring that location to which the charged particles were directed does not ablate in response to the pulse of laser light that causes the location to enter 'sample energy pumping state', as the laser spot on the sample can be larger than the diameter of the location to which charged particles were directed).

Accordingly, the invention provides an apparatus for analysing a sample, such as a biological sample, wherein the first focusing optics is configured to synchronise a pulse of laser beam to arrive at the location on the sample stage directly after a pulse of charged particles. This configuration of the present invention can overcome the relatively slow sputtering of particles by the charged particle beam alone and hence provide a quicker method of analysing a biological sample.

Accordingly, the invention provides an apparatus for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles.

In particular, the first focussing optics direct and focus the laser beam/laser radiation to the same location on a sample on the sample stage as previously targeted by the charged particles. This explanation applies to all apparatus discussed below in this section using the combination of features of a sample stage, source of charged particles and first laser source and first focussing optics that causes a pulse of radiation from the first laser source to illuminate the same location as previously targeted by the charged particles. It is merely not repeated each time below in the interests of brevity.

The apparatus typically comprises a mass detector, such as a TOF detector.

Accordingly, the invention provides a sampling and ionisation system for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles.

Figure 8:
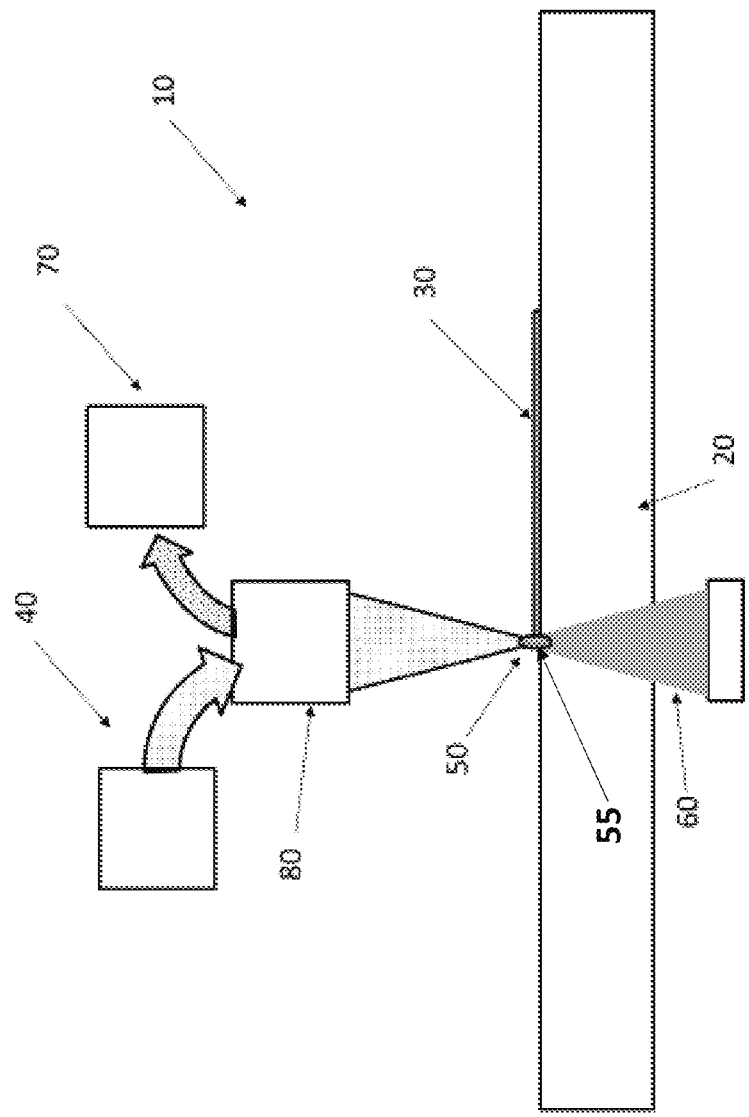
FIG. 8 is a schematic diagram of the optics arrangement of an apparatus for analysing a biological sample using laser pumping of the sample, through the sample carrier.

In particular, the first focussing optics direct and focus the laser beam/laser radiation to the same location on a sample on the sample stage as previously targeted by the charged particles. This explanation applies to all systems discussed below in this section using the combination of features of a sample stage, source of charged particles and first laser source and first focussing optics that causes a pulse of radiation from the first laser source to illuminate the same location as previously targeted by the charged particles. It is merely not repeated each time below in the interests of brevity. FIG. 8 is a schematic diagram of the arrangement of a further exemplary embodiment of the invention. FIG. 8 includes elements in common with FIGS. 6 and 7 and these elements share the same reference numeral. In this embodiment, the sample stage 20 is transparent (as is any sample carrier on which the sample is positioned). The skilled person would understand that transparent sample stages or sample stages comprising a cut-out portion could be used with any of the embodiments of the sputtering based sampling and ionising systems described herein. Transparent sample stages are described in more detail herein.

In the embodiment shown in FIG. 8, the source of charged particles and charged particle column, and first laser source and the first focusing optics are configured such that the beam of charged particles and the laser beam are directed towards the opposite sides of the sample stage. In the embodiment shown in FIG. 8, the charged particles are passed towards the location 55 on the sample and the laser beam is also directed towards the location 55 on the sample. In the same way as the embodiment shown in FIG. 7, in the embodiment of FIG. 8, a pulsed beam of charged particles provides a sample ignition state and a pulsed laser beam provides an energy pumping state to result in a plume of material comprising sample ions.

Figure 9:
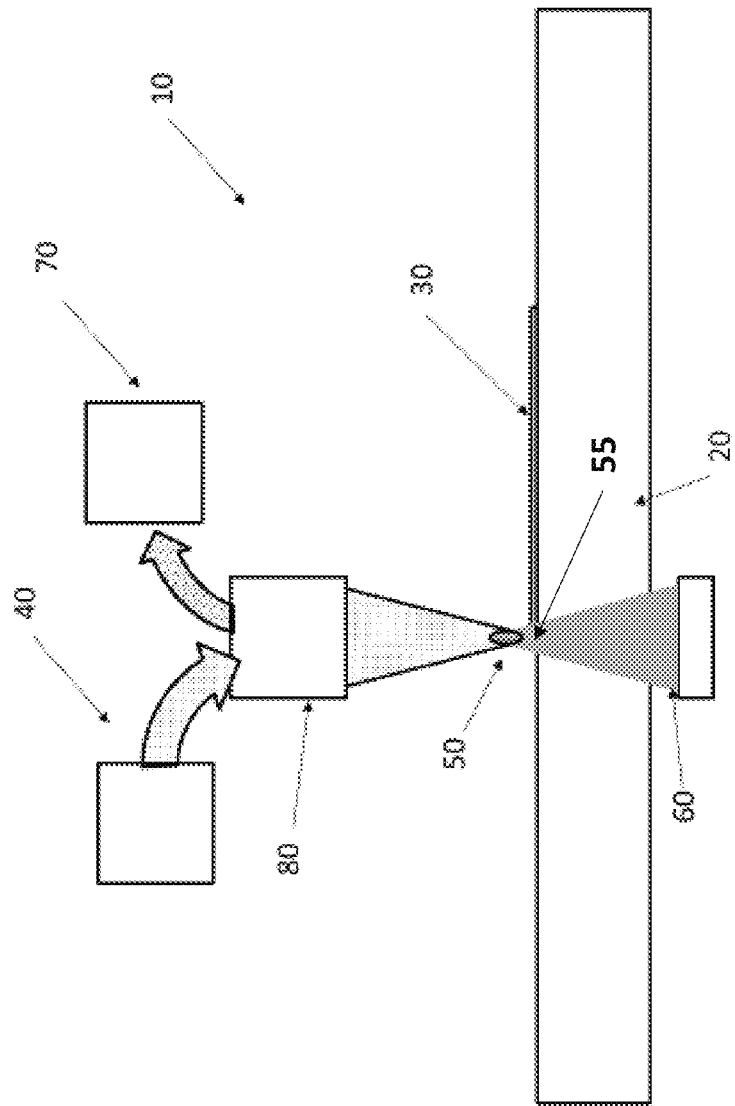
FIG. 9 is a schematic diagram of the optics arrangement of an apparatus for analysing a biological sample using \ laser post-ionisation of the sample, through the sample carrier.

FIG. 9 is a schematic diagram of the arrangement of a further exemplary embodiment of the invention. FIG. 9 includes elements in common with FIGS. 6 to 8 and these elements share the same reference numeral. Similarly to the embodiment shown in FIG. 8, in this embodiment of the invention, the source of charged particles and charged particle column, and first laser source and the first focusing optics are configured such that the beam of charged particles and the laser beam are directed towards the opposite sides of the sample stage. The sample 30 is positioned on sample stage 20 such the charged particles passed towards location 55 sputter material 50 from the sample 30. A first laser source 60 emits a laser beam and focusing optics (not shown) direct the laser beam towards the sample stage to ionise the sputtered material 50, forming a plume of material comprising sample ions. The ions can then be transferred to a mass detector, for example a time of flight detector, or any other mass detector which is discussed in more detail below.

Of note, in any of the above embodiments, the charged particle beam may be scanned across the sample to analyse an arbitrary region of interest, such as an organelle, as discussed earlier.

Accordingly, invention provides for an apparatus wherein the source of charged particles and charged particle column, and the first laser source and first focusing optics, are configured such that the beam of charged particles and laser beam are directed towards the same side of the sample stage. Examples of this type of apparatus are shown in FIGS. 6 and 7.

Accordingly, the invention provides an apparatus for analysing a sample, such as a biological sample, comprising:
- a sample stage;
- a source of charged particles and a charged particle column for passing a beam of charged particles to a location on the sample stage; and
- a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
- wherein the source of charged particles and charged particle column, and the first laser source and first focusing optics, are configured such that the beam of charged particles and laser beam are directed towards the same side of the sample stage.

The apparatus typically comprises a mass detector, such as a TOF detector.

Accordingly, the invention provides a sampling and ionisation system for analysing a sample, such as a biological sample, comprising:
- a sample stage;
- a source of charged particles and a charged particle column for passing a beam of charged particles to a location on the sample stage; and
- a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
- wherein the source of charged particles and charged particle column, and the first laser source and first focusing optics, are configured such that the beam of charged particles and laser beam are directed towards the same side of the sample stage.

For instance, the invention provides an apparatus for analysing a sample, such as a biological sample, comprising:
- a sample stage comprising a first face and a second face, the first and second faces being opposed, and wherein the first face is adapted to receive a sample;
- a source of charged particles and a charged particle column for passing a beam of charged particles to a location on the first face of the sample stage; and
- a first laser source and first focusing optics configured to direct a laser beam emitted by the first laser source towards the first face of the sample stage, wherein the first focusing optics is configured to synchronise a pulse of the laser beam to arrive at the location on the sample stage directly after a pulse of charged particles The apparatus typically comprises a mass detector, such as a TOF detector.

For instance, the invention provides a sampling and ionisation system for analysing a sample, such as a biological sample, comprising:
- a sample stage comprising a first face and a second face, the first and second faces being opposed, and wherein the first face is adapted to receive a sample;
- a source of charged particles and a charged particle column for passing a beam of charged particles to a location on the first face of the sample stage; and
- a first laser source and first focusing optics configured to direct a laser beam emitted by the first laser source towards the first face of the sample stage, wherein the first focusing optics is configured to synchronise a pulse of the laser beam to arrive at the location on the sample stage directly after a pulse of charged particles.

Accordingly, the invention provides an apparatus for analysing a sample, such as a biological sample, comprising:
- a sample stage;
- a source of charged particles and a charged particle column for passing a beam of charged particles to a location on the sample stage; and
- a first laser source and first focusing optics configured to direct a laser beam emitted by the first laser source towards the sample stage, wherein the first focusing optics is configured to synchronise a pulse of laser beam to ionise a plume of material sputtered by a pulse of charged particles from the source of charged particles; and
- wherein the source of charged particles and charged particle column, and the first laser source and first focusing optics, are configured such that the beam of charged particles and laser beam are directed towards the same side of the sample stage.

The apparatus typically comprises a mass detector, such as a TOF detector.

Accordingly, the invention provides a sampling and ionisation system for analysing a sample, such as a biological sample, comprising:
- a sample stage;
- a source of charged particles and a charged particle column for passing a beam of charged particles to a location on the sample stage; and
- a first laser source and first focusing optics configured to direct a laser beam emitted by the first laser source towards the sample stage, wherein the first focusing optics is configured to synchronise a pulse of laser beam to ionise a plume of material sputtered by a pulse of charged particles from the source of charged particles; and
- wherein the source of charged particles and charged particle column, and the first laser source and first focusing optics, are configured such that the beam of charged particles and laser beam are directed towards the same side of the sample stage.

For instance, the invention provides an apparatus for analysing a sample, such as a biological sample, comprising:
- a sample stage comprising a first face and a second face, the first and second faces being opposed, and wherein the first face is adapted to receive a sample;

a source of charged particles and a charged particle column for passing a beam of charged particles to a location on the first face of the sample stage; and a first laser source and first focusing optics configured to direct a laser beam emitted by the first laser source towards the first face of the sample stage, wherein the first focusing optics is configured to synchronise a pulse of laser beam to ionise a plume of material sputtered by from the sample by a pulse of charged particles from the source of charged particles.

The apparatus typically comprises a mass detector, such as a TOF detector.

For instance, the invention provides a sampling and ionisation system for analysing a sample, such as a biological sample, comprising:
a sample stage comprising a first face and a second face, the first and second faces being opposed, and wherein the first face is adapted to receive a sample;
a source of charged particles and a charged particle column for passing a beam of charged particles to a location on the first face of the sample stage; and
a first laser source and first focusing optics configured to direct a laser beam emitted by the first laser source towards the first face of the sample stage, wherein the first focusing optics is configured to synchronise a pulse of laser beam to ionise a plume of material sputtered by from the sample by a pulse of charged particles from the source of charged particles.

In addition, the invention provides an apparatus wherein the source of charged particles and charged particle column, and the first laser source and first focusing optics, are configured such that the beam of charged particles and laser beam are directed towards opposite sides of the sample stage. Examples of this type of apparatus are shown in FIGS. 8 and 9. An advantage of these types of set-up is that they minimise the mechanical complications of combining the charged particle column and the focusing optics. In certain aspects, the charged particle may be directed toward the sample through the support or substrate that is at least partially transparent to the charged particles, and ablate the sample or seed electrons in the sample. In such aspects, the sample may be thin, such as less than 200 nm, less than 100 nm, less than 50 nm, or less than 30 nm.

Accordingly, the invention provides an apparatus for analysing a sample, such as a biological sample, comprising:
a sample stage;
a source of charged particles and a charged particle column for passing a beam of charged particles to a location on the sample stage; and
a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
wherein the source of charged particles and charged particle column, and the first laser source and first focusing optics, are configured such that the beam of charged particles and laser beam are directed towards opposite sides of the sample stage.

The apparatus typically comprises a mass detector, such as a TOF detector.

Accordingly, the invention provides a sampling and ionisation system for analysing a sample, such as a biological sample, comprising:

a sample stage;
a source of charged particles and a charged particle column for passing a beam of charged particles to a location on the sample stage; and
a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
wherein the source of charged particles and charged particle column, and the first laser source and first focusing optics, are configured such that the beam of charged particles and laser beam are directed towards opposite sides of the sample stage.

For instance, the invention provides an apparatus for analysing a sample, such as a biological sample, comprising:
a sample stage comprising a first face and a second face, the first and second faces being opposed, and wherein the first face is adapted to receive a sample;
a source of charged particles and a charged particle column for passing a beam of charged particles to a location on the first face of the sample stage; and
a first laser source and first focusing optics configured to direct a laser beam emitted by the first laser source towards the second face of the sample stage, wherein the first focusing optics is configured to synchronise a pulse of the laser beam to arrive at the location on the sample stage directly after a pulse of charged particles The apparatus typically comprises a mass detector, such as a TOF detector.

For instance, the invention provides a sampling and ionisation system for analysing a sample, such as a biological sample, comprising:
a sample stage comprising a first face and a second face, the first and second faces being opposed, and wherein the first face is adapted to receive a sample;
a source of charged particles and a charged particle column for passing a beam of charged particles to a location on the first face of the sample stage; and
a first laser source and first focusing optics configured to direct a laser beam emitted by the first laser source towards the second face of the sample stage, wherein the first focusing optics is configured to synchronise a pulse of the laser beam to arrive at the location on the sample stage directly after a pulse of charged particles.

As explained elsewhere herein, and reiterated here for completeness, when the laser beam is recited through the sample stage to reach a sample on the first face, the stage should be transparent to the laser radiation (as should the sample carrier for the sample), or the sample stage should include a void through which laser radiation can pass to reach the sample (through the sample carrier)

Figure 10:
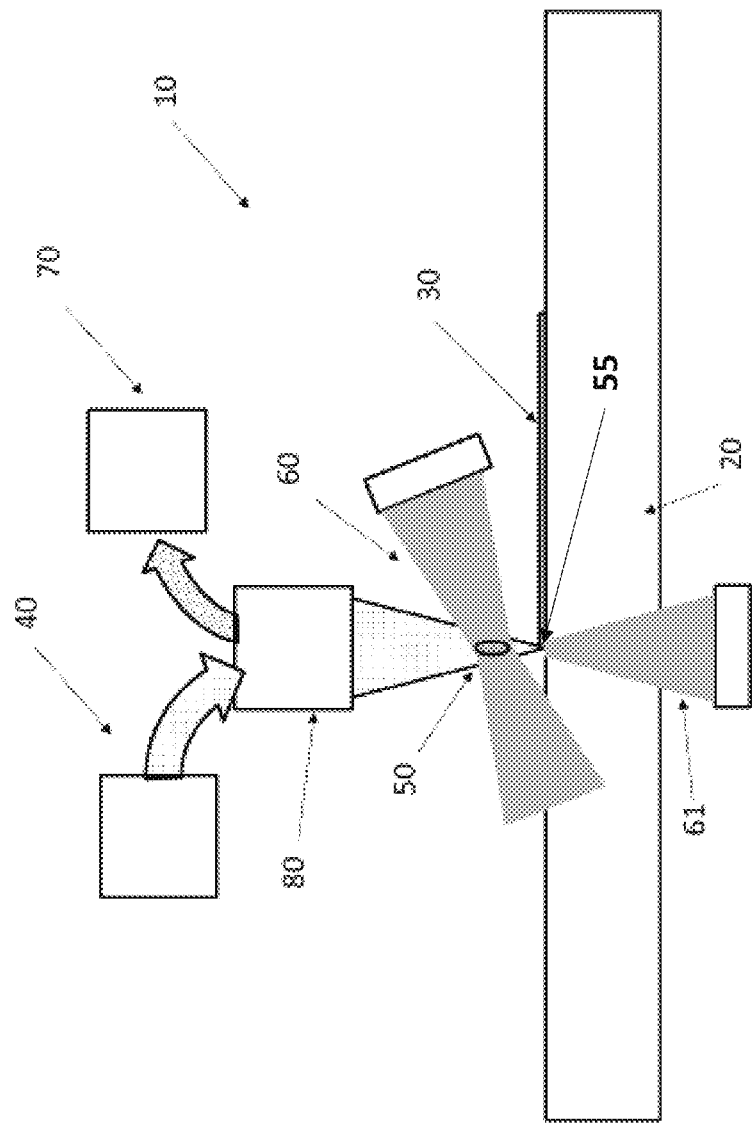
FIG. 10 is a schematic diagram of the optics arrangement of an apparatus for analysing a biological sample comprising at least two laser sources, one for laser post-ionisation and one for laser pumping of the sample.

The skilled person would also understand that the configurations of FIGS. 6 to 9 can be combined in various ways. FIG. 10 shows a further exemplary embodiment of the invention which is a combination of the configurations of FIGS. 6 to 9, again elements in common with FIGS. 6 to 9 are labelled with the same reference numeral.

The embodiment shown in FIG. 10 includes a second laser source 61 and second focusing optics (not shown). Similarly to the first laser source 60 and second focusing optics of FIG. 8, the second laser source 61 and second focusing optics of this embodiment are configured to direct a second laser beam towards location 55 on the sample stage. In the same way as the embodiments shown in FIGS. 7 and 8, the pulsed beam of charged particles provides a sample ignition state and a pulsed laser beam from the second laser source 61 provides an energy pumping state to result in a plume of material comprising sample ions. In this embodiment of the invention, the first laser source 60 and first focusing optics are configured to ionise a plume of material sputtered by the pulse of charged particles. Therefore, the first laser source 60 will ionise any neutral material sputtered from the surface not ionised by the energy pumping state. Hence, since both the first and second laser source are configured to ionise a plume of material to produce sample ions the present invention provides an apparatus which further improves ionisation probability and so increases signal-to-noise ratio. Thus, the invention provides an apparatus that analyses a sample with increased resolution.

Accordingly, the present invention provides for an apparatus as described above in this section comprising a second laser source and second focusing optics, wherein the second focusing optics are configured to synchronise a pulse of laser light from the second laser source to ionise a plume of material sputtered by a pulse of charged particles. In certain aspects, the first and second laser sources can comprise the same laser, wherein the control of the laser and/or optics allow for the two-step laser radiation described herein.

Accordingly, the invention provides an apparatus for analysing a sample, such as a biological sample, comprising:
  a sample stage;
  a source of charged particles and a charged particle column for passing a beam of charged particles to a location on the sample stage;
  a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
  a second laser source and second focusing optics, wherein the second focusing optics are configured to synchronise a pulse of the laser beam from the second laser source to ionise a plume of sample material from the location on the sample, generated by the pulse of charged particles and the pulse of the laser beam from the first laser source.

The apparatus typically comprises a mass detector, such as a TOF detector.

Accordingly, the invention provides a sampling and ionisation system for analysing a sample, such as a biological sample, comprising:
  a sample stage;
  a source of charged particles and a charged particle column for passing a beam of charged particles to a location on the sample stage;
  a first laser source and first focusing optics configured to direct a laser beam emitted by the first laser source towards the sample stage, wherein the first focusing optics is configured to synchronise a pulse of laser beam to ionise a plume of material sputtered by a pulse of charged particles from the source of charged particles; and
  a second laser source and second focusing optics, wherein the second focusing optics are configured to synchronise a pulse of the laser beam from the second laser source to ionise a plume of sample material from the location, generated by the pulse of charged particles and the pulse of the laser beam from the first laser source.

Accordingly, the present invention provides for an apparatus wherein the first laser source and first focusing optics and second laser source and second focusing optics, are configured such that the laser beam from the first laser source and laser beam from the second laser source are directed towards are directed towards the same side of the sample stage.

Accordingly, the invention provides an apparatus for analysing a sample, such as a biological sample, comprising:
  a sample stage;
  a source of charged particles and a charged particle column for passing a beam of charged particles to a location on the sample stage;
  a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
  a second laser source and second focusing optics, wherein the second focusing optics are configured to synchronise a pulse of the laser beam from the second laser source to ionise a plume of sample material from the location on the sample, generated by the pulse of charged particles and the pulse of the laser beam from the first laser source, wherein the source of charged particles and charged particle column, the first laser source and first focusing optics, and the second laser source and second focusing optics are configured such that the beam of charged particles, laser beam from the first laser source and laser beam from the second laser source are directed towards the same side of the sample stage.

The apparatus typically comprises a mass detector, such as a TOF detector.

Accordingly, the invention provides a sampling and ionisation system for analysing a sample, such as a biological sample, comprising:
  a sample stage;
  a source of charged particles and a charged particle column for passing a beam of charged particles to a location on the sample stage;
  a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and
  a second laser source and second focusing optics, wherein the second focusing optics are configured to synchronise a pulse of the laser beam from the second laser source to ionise a plume of sample material from the location on the sample, generated by the pulse of charged particles and the pulse of the laser beam from the first laser source, wherein the source of charged particles and charged particle column, the first laser source and first focusing optics, and the second laser source and second focusing optics are configured such that the beam of charged particles, laser beam from the first laser source and laser beam from the second laser source are directed towards the same side of the sample stage.

For instance, the invention provides an apparatus for analysing a sample, such as a biological sample, comprising:
  a sample stage comprising a first face and a second face, the first and second faces being opposed, and wherein the first face is adapted to receive a sample;

a source of charged particles and a charged particle column for passing a beam of charged particles to a location on the first face of the sample stage;

a first laser source and first focusing optics configured to direct a laser beam emitted by the first laser source towards the first face of the sample stage, wherein the first focusing optics is configured to synchronise a pulse of the laser beam to arrive at the location on the first face of the sample stage directly after a pulse of charged particles; and a second laser source and second focusing optics configured to direct a laser beam emitted by the second laser source towards the first face of the sample stage, wherein the second focusing optics are configured to synchronise a pulse of the laser beam from the second laser source to ionise a plume of sample material from the location on the sample, generated by the pulse of charged particles and the pulse of the laser beam from the first laser source.

The apparatus typically comprises a mass detector, such as a TOF detector.

Accordingly, the invention provides a sampling and ionisation system for analysing a sample, such as a biological sample, comprising:

a sample stage comprising a first face and a second face, the first and second faces being opposed, and wherein the first face is adapted to receive a sample;

a source of charged particles and a charged particle column for passing a beam of charged particles to a location on the first face of the sample stage;

a first laser source and first focusing optics configured to direct a laser beam emitted by the first laser source towards the first face of the sample stage, wherein the first focusing optics is configured to synchronise a pulse of the laser beam to arrive at the location on the first face of the sample stage directly after a pulse of charged particles; and a second laser source and second focusing optics configured to direct a laser beam emitted by the second laser source towards the first face of the sample stage, wherein the second focusing optics are configured to synchronise a pulse of the laser beam from the second laser source to ionise a plume of sample material from the location on the sample, generated by the pulse of charged particles and the pulse of the laser beam from the first laser source.

Accordingly, the invention provides an apparatus wherein the first laser source and first focusing optics and second laser source and second focusing optics, are configured such that the laser beam from the first laser source and laser beam from the second laser source are directed towards opposite sides of the sample stage.

Accordingly, the invention provides an apparatus for analysing a sample, such as a biological sample, comprising:

a sample stage;

a source of charged particles and a charged particle column for passing a beam of charged particles to a location on the sample stage;

a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and a second laser source and second focusing optics, wherein the second focusing optics are configured to synchronise a pulse of the laser beam from the second laser source to ionise a plume of sample material from the location on the sample, generated by the pulse of charged particles and the pulse of the laser beam from the first laser source, wherein the source of charged particles and charged particle column, and the second laser source and second focusing optics are configured such that the beam of charged particles and laser beam from the second laser source are directed towards the same side of the sample stage; and the first laser source and first focusing optics are configured such that the laser beam from the first laser source is directed towards the opposite side of the sample stage.

The apparatus typically comprises a mass detector, such as a TOF detector.

Accordingly, the invention provides a sampling and ionisation system for analysing a sample, such as a biological sample, comprising:

a sample stage;

a source of charged particles and a charged particle column for passing a beam of charged particles to a location on the sample stage;

a first laser source and first focusing optics configured to direct a laser beam emitted by the first laser source towards the sample stage, wherein the first focusing optics is configured to synchronise a pulse of the laser beam to arrive at the location on the sample stage directly after a pulse of charged particles; and a second laser source and second focusing optics, wherein the second focusing optics are configured to synchronise a pulse of the laser beam from the second laser source to ionise a plume of sample material from the location on the sample, generated by the pulse of charged particles and the pulse of the laser beam from the first laser source, wherein the source of charged particles and charged particle column, and the second laser source and second focusing optics are configured such that the beam of charged particles and laser beam from the second laser source are directed towards the same side of the sample stage; and the first laser source and first focusing optics are configured such that the laser beam from the first laser source is directed towards the opposite side of the sample stage.

For instance, the invention provides an apparatus for analysing a sample, such as a biological sample, comprising:

a sample stage comprising a first face and a second face, the first and second faces being opposed, and wherein the first face is adapted to receive a sample;

a source of charged particles and a charged particle column for passing a beam of charged particles to a location on the first face of the sample stage;

a first laser source and first focusing optics configured to direct a laser beam emitted by the first laser source towards the second face of the sample stage, wherein the first focusing optics is configured to synchronise a pulse of the laser beam to arrive at the location on the first face of the sample stage directly after a pulse of charged particles; and a second laser source and second focusing optics configured to direct a laser beam emitted by the second laser source towards the first face of the sample stage, wherein the second focusing optics are configured to synchronise a pulse of the laser beam from the second laser source to ionise a plume of sample material from the location, generated by the pulse of charged particles and the pulse of the laser beam from the first laser source.

The apparatus typically comprises a mass detector, such as a TOF detector.

Accordingly, the invention provides a sampling and ionisation system for analysing a sample, such as a biological sample, comprising:

- a sample stage comprising a first face and a second face, the first and second faces being opposed, and wherein the first face is adapted to receive a sample;
- a source of charged particles and a charged particle column for passing a beam of charged particles to a location on the first face of the sample stage;
- a first laser source and first focusing optics configured to direct a laser beam emitted by the first laser source towards the second face of the sample stage, wherein the first focusing optics is configured to synchronise a pulse of the laser beam to arrive at the location on the first face of the sample stage directly after a pulse of charged particles; and
- a second laser source and second focusing optics configured to direct a laser beam emitted by the second laser source towards the first face of the sample stage, wherein the second focusing optics are configured to synchronise a pulse of the laser beam from the second laser source to ionise a plume of sample material from the location,
- generated by the pulse of charged particles and the pulse of the laser beam from the first laser source.

The invention also provides methods of analysing a biological sample using an apparatus as described in this section. For instance, the invention provides a method comprising:

- passing a beam of charged particles towards a location on the sample; illuminating the sample with a first pulse of laser beam to produce a plume of material comprising sample ions; and
- detecting said sample ions by mass spectrometry.

In some instances, the method comprises passing the beam of charged particles towards a location on the sample to sputter material from the sample; and wherein the method comprises illuminating the sputtered sample material with the first pulse of laser beam and ionising the sputtered material to produce sample ions. That is to say, the method comprises passing the beam of charged particles towards a location on the sample to sputter material from the sample; and wherein the method comprises illuminating the sputtered sample material with the first pulse of laser beam thereby ionising the sputtered material to produce sample ions. Sometimes, passing the beam of charged particles towards a location on the sample produces a sample ignition state; and wherein illuminating the sample at the location produces a sample energy pumping state at the location on the sample.

In some of the methods, the beam of charged particles is passed towards a location on the sample from one side of the sample, and wherein the first pulse of laser beam illuminates the sample from the same side of the sample. In some embodiments the beam of charged particles is passed towards a location on the sample from one side of the sample, and wherein the first pulse of laser beam illuminates the sample from the opposite side of the sample. Sometimes, passing the beam of charged particles towards a location on the sample further comprises sputtering material from the sample; and wherein the method comprises illuminating the sputtered sample material with a second pulse of laser beam and ionising the sputtered material. The first and second pulses of laser beam illuminate the sample from the same side of the sample or the first and second pulses of laser beam illuminate the sample from opposite sides of the sample.

As the skilled person will appreciate, the laser ionisation of the sputtered material can be accomplished by various ionisation mechanisms including single photon ionisation, resonant and non-resonant multiphoton ionisation, avalanche ionisation and cold avalanche ionisation. Furthermore, different ionisation mechanisms can operate simultaneously, such as multiphoton ionisation and avalanche ionisation.

Single photon ionisation (SPI) is the process by which the absorption of one photon is sufficient to overcome the ionisation potential sputtered material. However, ionisation by this means requires very high energy ultraviolet or vacuum ultraviolet lasers, for example excimer lasers, or complex systems employing non-linear optical processes in gases. Accordingly, the present invention provides methods and apparatus wherein the first and/or second laser source is a high energy ultraviolet or vacuum ultraviolet laser.

Multiphoton ionisation (MPI) involves the absorption of more than one photon in order to overcome the ionisation potential, this absorption can be in non-resonant or resonant steps. Multiphoton ionisation requires short and intense laser pulses. Suitable lasers for resonant systems include pulsed Nd:YAG laser pumping two dye lasers, suitable lasers for non-resonant laser systems include a high-power excimer or Nd:YAg laser. Accordingly, the present invention provides methods and apparatus wherein the first and/or second laser source is a Nd:YAG laser pumping two dye lasers, a high-power excimer or Nd:YAG laser.

Avalanche ionisation (AI) is the process by which electrons collide with and ionise sputtered material, resulting in additional electrons which accelerate and collide with other sputtered material, thereby creating a chain reaction. In the present invention, the initial 'seed' electrons may be the result of any such ionisation mechanism that results from the application of a laser pulse, for example multiphoton ionisation or single photon ionisation. Some models imply that avalanche ionisation is unimportant when the laser pulse is shorter than 100 fs. However, various techniques have been demonstrated where avalanche ionisation persists at laser pulses shorter than 100 fs. The present invention provides methods utilising these techniques in order to ionise sputtered material by means of avalanche ionisation using laser pulses shorter than 100 fs.

In the first technique, the electric field imposed by an intense ionising laser on the sample is used to reduce the effective energy threshold at which collisional ionisation occurs and so thus allow collisional ionisation to drive avalanche ionisation even at short pulse lengths (less than 100 fs). This is a cold avalanche ionisation mechanism. Suitable lasers may be, for example a Ti:sapphire laser (800 nm, 40-45 fs pulse length, energy 75 nJ, e.g. Octavius Ti:Sapphire Lasers, available from Thorlabs) and it has been shown that avalanche ionisation of fused silica can be achieved with 800 nm laser pulses as low as 40 fs from a regenerative amplifier (Rajeev, Gertsvolf et al. 2009, PRL 201). Accordingly, the present invention provides methods and apparatus wherein the first and/or second laser source is a Ti:sapphire laser for ionising the sputtered material by avalanche ionisation. In certain aspects, the mechanism of ignition (e.g., electron seeding seeding) followed by plasma development (e.g., avalanche ionisation) may be similar for dielectrics and for biological samples. In the case of biological samples, the sample format may be in an epoxy resin which is a dielectric, though different than Silicon Oxide.

In the second technique, free carriers are injected into the sample to encourage exciton-seeded multiphoton ionisation in combination with avalanche ionisation. Free carriers can be injected into a dielectric from extreme ultraviolet sources created by high-harmonic or attosecond pulse generation and the sample can be ionised using a laser pulse as short as 45 fs (800 nm laser), (Grojo, Gertsvolf et al. 2010, PR 81). Accordingly, the present invention provides methods and apparatus wherein the first and/or second laser source is an extreme ultraviolet source.

Accordingly, the present invention provides methods and apparatus wherein the first and/or second laser is configured to ionise sputtered material by avalanche ionisation.

In this way, the present invention further addresses the two main challenges in enhancing the resolution of IMC to sub micrometer scales. Firstly, because laser pulses shorter than 100 fs can be used to effect avalanche ionisation, the risk of the area around the laser spot size being damaged due to heating effects is reduced. In this way, the present invention maintains the spot area to a size of around 200 nm or less. Secondly, the present invention improves the likelihood of multiphoton and avalanche ionisation and therefore improves overall ionisation rates. In this way, the overall amount of analyte in the ablated material provides a sufficient signal-to-noise ratio.

Components of Sputtering Based Sampling and Ionising System

Source of Charged Particles

As discussed above, in the present invention, a source of charged particles and a charged particle column may be used to pass a beam of charged particles to a location on the sample.

Primary Ion Beam:

Typically, the source of charged particles used in secondary neutral mass spectrometry is a primary ion beam source. The primary ions can be any suitable ion for generating sputtering from the sample to be analysed. Examples of primary ion sources are: the Duoplasmatron which generates oxygen ($^{16}O^-$, $^{16}O_2^+$, $^{16}O_2^-$), argon ($^{40}Ar^+$), xenon ($Xe^+$), $SF_5^+$, or $C_{60}^+$ primary ions; a surface ionisation source which generates $^{133}Cs^+$ primary ions; and liquid metal ion guns (LMIG) which generate $Ga^+$ primary ions. Other primary ions include cluster ions such as $Au_n^+$ (n=1-5), $Bi_n^{q+}$ (n=1-7, q=1 and 12), $C_{60}^{q+}$ probes (q=1-3) and large Ar clusters (Muramoto, Brison, & Castner, 2012).

The choice of ion source depends on the type of ion bombardment being deployed (i.e. static or dynamic) and the sample to be analysed. Static involves using a low primary ion beam current (1 nA/cm$^2$), usually a pulsed ion beam. Because of the low current, each ion strikes a new section of the sample surface, removing only a monolayer of particles (2 nm). Hence, static is suitable for imaging and surface analysis (Gamble & Anderton, 2016). Dynamic involves using a high primary ion beam current (10 mA/cm$^2$), usually a continuous primary ion beam, which results in the fast removal of surface particles. As a result, is possible to use dynamic for depth profiling. Furthermore, since more material is removed from the sample surface, dynamic SIMS gives a better detection limit than static. Dynamic typically produces high image resolution (less than 100 nm) (Vickerman & Briggs, 2013).

Oxygen primary ions enhance ionisation of electropositive elements (Malherbe, Penen, Isaure, & Frank, 2016) and are used in the commercially available Cameca IMS 1280-HR, whereas caesium primary ions are used to investigate electronegative elements (Kiss, 2012) and are used in the commercially available Cameca NanoSIMS 50.

For rapid analysis of a sample a high frequency of sputtering is needed, for example more than 200 Hz (i.e. more than 200 packets of ions directed at the sample per second). Commonly, the frequency of primary ion pulse generation by the primary ion source is at least 400 Hz, such as at least 500 Hz, or at least 1 kHz. For instance, the frequency of ion pulses in some embodiments is at least 10 kHz, at least 100 kHz, at least 1 MHz, or at least 10 MHz. For instance, the frequency of ion pulses is within the range 400-100 MHz, within the range 1 kHz-100 MHz, within the range 10 kHz-100 MHz, within the range 100 kHz-100 MHz or within the range 1 MHz-100 MHz.

Accordingly, the present invention provides an apparatus wherein the source of charged particles is a primary ion beam.

Electron Beam

Alternatively, in some embodiments of the present invention, the source of charged particles is an electron beam. Electron beams with the energy of 2 kV to 30 kV may be particularly suitable to interrogate a specimen with a thickness of 30 nm.

A high intensity pulsed electron beam is used to cause ablation/sputtering. When the pulse of the electron current is insufficient for ablation, its effect can be used just as an ignition event as described above, followed by energy pumping by the laser pulse set at the brightness level below the level of ablation of native material but above the level of energy pumping required for ablation of an already activated material. In the energy activated mode of ablation/sputtering, the electron energy can be lowered as the electrons only serve to inject charge carriers into otherwise insulating material.

In certain aspects, the electron beam may be focused at a smaller spot (at a higher resolution) than the laser beam. A laser of lower resolution may only ablate and/or ignite sample at the spot radiated by the electron beam, even when it impinges sample beyond the electron beam spot. For example, the electron beam may be focused to a spot of 200 nm, 100 nm, 50 nm, 30 nm, or 10 nm or less and the laser may be focussed to a spot of 200 nm, 300 nm, 500 nm, 800 nm, 1 um, 2 um or more that overlaps with the electron beam spot or is focused on an ablation plume release by the electron beam.

For rapid analysis of a sample a high frequency of sputtering is needed, for example more than 200 Hz (i.e. more than 200 packets of electrons directed at the sample per second). Commonly, the frequency of electron pulse generation by the electron source is at least 400 Hz, such as at least 500 Hz, or at least 1 kHz. For instance, the frequency of electron pulses in some embodiments is at least 10 kHz, at least 100 kHz, at least 1 MHz, or at least 10 MHz. For instance, the frequency of electron pulses is within the range 400-100 MHz, within the range 1 kHz-100 MHz, within the range 10 kHz-100 MHz, within the range 100 kHz-100 MHz or within the range 1 MHz-100 MHz.

An advantage of utilising an electron beam for the source of charged particles is that the whole instrument can be built on a platform containing an electron microscope. Accordingly, the present invention provides an apparatus further comprising an electron microscope. Accordingly, the present invention provides an apparatus wherein the source of charged particles is an electron beam wherein the electron beam is an electron source in the electron microscope.

Charged Particle Column

The charged particle column directs the charged particles to the sample. The charged particle column comprises: a mass filter in order to filter out impurities in the charged particle beam; lenses and apertures as appropriate in order to control the intensity and shape of the primary ion beam; and deflection plates in order to shape the primary ion beam and optionally raster the charged particle beam across the surface of the sample (Villacob, 2016). Ion lenses and other components for constructing the charged particle column are commercially available, e.g. from Agilent. Accordingly, the charged particle column of the present invention can provide a charged particle beam scanning system adapted to scan the beam of charged particles across a plurality of locations on the sample stage Typically, the charged particle beam used for secondary ion generation herein has a spot size (i.e. size of the charged particle beam when it hits the sample) of 100 µm or less, such as 20 µm or less, 5 µm or less, 1 µm or less, or 500 nm or less, or 300 nm or less, 200 nm or less, 100 nm or less, 50 nm or less, or 30 nm or less. The distance referred to as spot size corresponds to the longest internal dimension of the ion beam, e.g. for a circular beam it is a beam of diameter 2 µm, for a square beam corresponds to the length of the diagonal between opposed corners, for a quadrilateral it is the length of the longest diagonal etc. Beam shaping and beam masking can be employed to provide the spot shape and size.

When used for analysis of biological samples, in order to analyse individual cells, the spot size of ion beam used will depend on the size and spacing of the cells. For example, where the cells are tightly packed against one another (such as in a tissue section) the charged particle beam can have a spot size which is no larger than these cells if single cell analysis is to be conducted. This size will depend on the particular cells in a sample, but in general the ion beam spot will have a diameter of less than 4 µm e.g. within the range 0.1-4 µm, 0.25-3 µm, or 0.4-2 µm. Thus, a charged particle beam spot can have a diameter of about 3 µm or less, about 2 µm or less, about 1 µm or less, about 0.5 µm or less than 0.5 µm, such as about 400 nm or less, about 300 nm or less. In particular embodiments, the spot size is about 200 nm or less, about 100 nm or less than 100 nm. In order to analyse cells at a subcellular resolution the system uses a primary ion beam spot size which is no larger than these cells, and more specifically uses a primary ion beam spot size which can ablate material with a subcellular resolution. Sometimes, single cell analysis can be performed using a spot size larger than the size of the cell, for example where cells are spread out on the slide, with space between the cells. The particular spot size used can therefore be selected appropriately dependent upon the size of the cells being analysed. In biological samples, the cells will rarely all be of the same size, and so if subcellular resolution imaging is desired, the ion beam spot size should be smaller than the smallest cell, if constant spot size is maintained throughout the sputtering procedure.

Lasers

In the present invention, lasers can be used in order to ablate material, or to assist in sputtering of material by illuminating a location after a pulse of charged particles has been passed towards a location on a sample (see for example, FIGS. 7 and 8 and accompanying description). In addition, lasers can be used to ionise sputtered material previously sputtered by a beam of charged particles (see for example, FIGS. 6 and 9 and accompanying description). Furthermore, lasers can be used for a combination of the above, see for example FIG. 10 and accompanying description.

As the skilled person will appreciate, the requirements of a laser for ablating/assisting the sputtering of material differ from the requirements of a laser for ionising material. Generally, lasers for assisting in the sputtering of material or for ablation provide energies of the order of µJ for pulse lengths of the order of 300 to 400 fs or greater. In contrast, lasers for ionising sputtered material are more powerful, providing energies of the order of 1 mJ or greater for pulse lengths shorter than 100 fs. The apparatus of the present invention may use different lasers for the first and second laser source or may use one laser for the first and second laser source and a beam splitter to split the laser and provide the first and second laser sources.

A variety of different lasers can be used for SNMS, including commercial lasers as discussed above in relation to the laser of the laser ablation sampling system, adapted as appropriate to enable sputtering of material. Generally, the laser is operated at the maximum achievable intensity in order to maximise ionisation. Various types of laser which can be used with the present invention are described below. Femtosecond lasers as discussed above are also advantageous in particular SNMS applications. For example, in the embodiments of the invention set out above which include first and second laser sources, a single femtosecond laser can be used to provide both laser sources. The laser could have a repetition rate of 1 MHz and a pulse width of 200 fs with the energy pulse of 1 microJ. The skilled person would understand that a beamsplitter can be used to split the laser beam of the laser to provide the first and second laser sources of the claimed invention.

Generally, lasers useful for ionisation include those which supply energy on the scale of a few microJoules of energy per pulse, but which are capable of producing those pulses with high frequency. The laser is for generating elemental ions from the sample material. The elemental ions generated can then be analysed by the mass spectrometer in the apparatus. The laser may be a picosecond laser or a femtosecond laser, or a nanosecond laser. In some embodiments the laser is a femtosecond laser.

The femtosecond laser may be a solid state laser. Passively mode-locked solid-state bulk lasers can emit high-quality ultrashort pulses with typical durations between 30 fs and 30 µs. Examples of such lasers include diode-pumped lasers, such as those based on neodymium-doped or ytterbium-doped crystals. Titanium—sapphire lasers can be used for pulse durations below 10 fs, in extreme cases down to approximately 5 fs (e.g. Octavius Ti:Sapphire Lasers, available from Thorlabs). The pulse repetition rate is in most cases between 1 kHz and 500 MHz.

The femtosecond laser may be a fiber laser. Various types of ultrafast fiber lasers, which may also be passively mode-locked, typically offer pulse durations between 50 and 500 fs, repetition rates between 0.10 and 100 MHz, and average power between a few milliwatts and several watts (femtosecond fiber lasers are commercially available from Toptica, IMRA America, Coherent, Inc.).

The femtosecond laser may be a semiconductor laser. Some mode-locked diode lasers can generate pulses with femtosecond durations. Directly at the laser output, the pulses durations are usually at least several hundred femtoseconds, but with external pulse compression, much shorter pulse durations can be achieved.

In some embodiments, the laser is a nanosecond laser. The nanosecond laser can be a pumped laser such as the Quantel Q-smart DPSS, the Solar Laser LQ929 high power pulsed Nd:YAG laser, or the Litron High Energy Pulsed Nd:YAG laser. All of these lasers can produce deep ultraviolet radiation within the mJ regime so suitable for ionisation and with short pulse durations.

It is also possible to passively mode-lock vertical external-cavity surface-emitting lasers (VECSELs); these are interesting particularly because they can deliver a combination of short pulse durations, high pulse repetition rates, and sometimes high average output power, whereas they are not suitable for high pulse energies.

In some embodiments the laser is adapted to produce a pulse of nanosecond, picosecond or femtosecond scale pulse duration. For example, the laser may have a duration of 500 fs or less, such as 400 fs or less, 300 fs or less, 200 fs or less, 100 fs or less, 50 fs or less, 45 fs or less, 25 fs or less, 20 fs or less or 10 fs or less. A femtosecond laser is adapted to produce pulses with a duration of less than 1 µs.

In some embodiments, the laser is adapted to have a pulse repetition rate of at least 100,000 Hz, such as at least 1 MHz, at least 2 MHz, at least 3 MHz, at least 4 MHz, at least 5 MHz, at least 10 MHz, at least 20 MHz, at least 50 MHz, at least 100 MHz, at least 200 MHz, at least 500 MHz or 1 GHz or more.

In some embodiments, the laser is adapted to have beam width ($1/e^2$) of 50 µm or less, 20 µm or less, 10 µpm or less, or 5 µm or less. The focal point of the laser is where the beam's energy is most concentrated and accordingly where the greatest ionisation is achieved.

In some embodiments, the laser is adapted to have a pulse energy of between 1 nanoJoule up to 50 milliJoules. Lasers for assisting in the sputtering of material or for ablation of material can be adapted to have a pulse energy of between 1 nanoJoule and 100 microJoules, such as between 10 nanoJoules and 100 microJoules, between 100 nanoJoules and 10 microJoules, between 500 nanoJoules and 5 microJoules, such as around 1 microJoule, around 2 microJoules, around 3 microJoules or around 4 microJoules. Laser for post ionisation can be adapted to have a pulse energy of between 1 milliJoule and 50 milliJoules, such as between 5 milliJoules and 40 milliJoules, 10 milliJoules and 30 milliJoules, 20 milliJoules and 35 milliJoules, or around 25 milliJoules or 35 milliJoules.

In some embodiments, the laser is adapted to have a pulse energy of around 1 microJoule, to have a pulse repetition rate of at least 10 MHz, and to produce pulses with a duration of less than 100 fs, such as 50 fs or less, 45 fs or less, 25 fs or less, 20 fs or less or 10 fs or less.

As the skilled person will appreciate, the present invention can be used with one or a combination of the suitable lasers as described herein. For completeness however, a number of specific combinations of lasers which can be used with present invention are as follows:

| Laser for assisting in the sputtering of material or for ablation of material | Laser for post ionisation |
| --- | --- |
| 2nd harmonic 532 nm Nd:Yag laser (Spectra Physics GCR 150) | 355 nm laser (CNI Laser, PS-R-355) |
| 2nd harmonic of 283.3 nm dye laser pumped by another Nd:Yag laser (Spectra Physics GCR 230), average power of lasers 0.3 mW and 12 mW respectively | 283.8 nm laser (Spectra Physics GCR 230) |
| Excimer laser KrF 248 nm (AZO Optics) | Excimer laser ArF 193 nm (ThorLabs NM07-H01) |

Post-ionisation requires a high energy density from the laser radiation in a small volume, e.g. 5 µm³ or less. Because the post ionization volume is so small it sets the limit on the amount of material that can be ionized in one go. If a large amount of positive and negative charges is created in a small volume the motion of the ions formed will be dominated by the local fields resulting from the space charge induced by the ions and electrons. If there are too many charged ions in a small volume, external fields, such as the fields from ion optics present in mass spectrometers used to direct the resulting ions to the detector for detection, will not be effective at separating positive and negative charges and such ion clouds will eventually neutralise reducing ionisation efficiency. For example, an ion cloud on a scale of 10 µm (in diameter) containing 10000 elemental charges creates an electrostatic potential that is about 3 V. Since a few eV is the energy holding the electrons to the atoms it is also the likely energy level of free electrons after ionisation. As a result, the ion density on the scale of 10000 ions in a volume on the 10 micrometer scale is near the limit where the space charge behaviour starts to dominate.

Accordingly, such effects can be avoided by ensuring that the amount of sputtered material is kept reasonably small. For example, ablation of material on the scale of 10×10×10 nm cube to 30×30×30 nm cube or a similar volume represents the highest amount of material that can be transferred into the post ionization area of a few micrometers is size without creating a strong space change and ion neutralization. Since the system can only process 30×30×30 nm cube per single event this creates an opportunity to conduct the imaging with the spatial resolution of 30 nm or even 10 nm, to which ion beams can be focused (as discussed herein).

The post ionization beam is co-aligned with the sputtering beam to within a micrometer precision, as is commonly obtained in optical setups.

In some embodiments, the laser beam is directed at an angle to the sample and into the previously ablated area of the specimen (see FIG. 6). This configuration minimizes the interaction between the laser light and the unablated specimen. The laser beam can be focused to a tight focus that overlaps with the volume of ablation plume. The laser beam focusing can be done at high numerical aperture (NA) to facilitate sharp focusing in the overlapping region and enable rapid laser energy spreading outside of the overlapping region to minimize the possibility of damage to the sample in the regions surrounding that being sampled.

Due to constraints in FIG. 6 of the ion optics that focuses the primary beam and transfers the secondary beam for mass analysis, the space for the laser beam optics may be limited in some embodiments. As a result, in some embodiments, numerical aperture of the laser beam may be constrained in one of the planes. For example, the laser beam may have a low NA in the plane of the drawing to avoid interferences with ion optics and high NA in the plane perpendicular to the plane of the drawing. Such an arrangement results in an elliptical focal spot that is extended in the plane of low NA. The elliptical focal spot may improve the degree of overlap with the sputtered/ablated plume. Accordingly, in some embodiments, the laser of the post-ionisation system has an elliptical focal spot.

In addition to spatial co-ordination, the sputtering due to the primary ion or electron beam needs to be synchronised with the delivery of laser radiation to ionise the sputtered material. The speed at which the sputtered material leaves the target is typically on the scale of the speed of sound i.e. 1000 m/s. Thus, to ensure alignment of the sputtered cloud and the laser beam with 1 micrometer precision requires timing precision on the scale of 1 ns. Ion beam bunching and timing to 1 ns is commonly achieved with accelerating voltages on the order of 5 to 20 kV. The same or similar bunching technology can be applied to the primary beam. This technology is used, for instance, in current TOF MS apparatus.

Thus in this mode of operation, the primary ion beam or electron beam sputters material from the sample, and very shortly after that, the ejected material is post-ionised by a pulse of laser radiation.

To further facilitate consistent sputtering/ejection of material from the target, in some instances, the target may be illuminated with a pulse of a laser light that is synchronized with the pulse of primary ions (instead of, or in addition to, the post-ionisation discussed above). The energy of the laser pulse should be set below ablation threshold for the material that has not been exposed to the primary ion or electron beam. In the area where the primary ion beam or electron beam interacts with the target, the state of the matter resembles plasma and since it is confined to a nano-scale it is referred to herein as a nano-plasma. Thus, the optical beam can interact with the nano-plasma and pump additional energy into this volume leading to a consistent desorption of material. This mode of desorption can be viewed as an ignition state (provided by the primary ion beam or electron beam interacting with the target and creating nano-plasma) followed by an energy pumping state where the laser light pumps additional energy into the nano-plasma facilitating its ejection.

This mode of operation can help to overcome the limitation of relatively slow sputtering by the primary ion or electron beam. Sputtering rate due to the primary ion beam/electron beam is limited by the total number of primary ions/electrons impacting the given area. The focusing ability of the primary ion beam/electron beam is limited due to the ion/electron current and space charge effects. This, combined with the need to time the primary ion beam/electron beam to only sputter material when the post ionization laser is off places a limit on the sputtering rate. Use of laser radiation to enhance sputtering can overcome the limitation as fewer primary particles are needed to seed the sample material with excitation energy needed for the laser beam to affect the sputtering/ablation.

In instances where a laser is used both for post-ionization and enhancing sputtering, the same laser could also be suitable for energy pumping into the nano-plasma to facilitate material desorption. For example, a single femtosecond laser can service both needs in the apparatus. The laser could have a repetition rate of 1 MHz and a pulse width of 200 fs with the energy per pulse of 1 microJ (i.e. average power of 1 W). Such laser pulse could be split up (e.g. using a beam splitter) and a portion of it used as is for energy pumping of nano-plasma. The remaining part could be used for post ionization. A compression stage can be applied to the post ionization beam to reduce the amount of energy per pulse required for post-ionization.

In some embodiments, the post ionization with the laser beam is carried out by pumping the energy to the nano-plasma on the surface. Thus, the desorption pumping and post ionization processes are combined into a single process activated by the laser pulse delivered to the nano-plasma on the target.

Moreover, the energy pumping into plasma on the target can be accomplished by tuning the laser wavelength to the absorption band of the plasma while avoiding absorption band of the unionized target material. As such, the impact of the primary ion beam/electron beam serves to change the state of the matter in the target from non-absorbing the pumping light to absorbing the pumping light. The duration of the pumping light can be on the scale of picoseconds up to a few nanoseconds and down to a few femtoseconds. At the same time, the picosecond pulse is short enough to avoid significant diffusion broadening of the plasma volume in the sample.

In some embodiments, the laser radiation for energy pumping is delivered through the sample carrier (see FIG. 8). For example, the primary electron beam or the primary ion beam can be focused to a spot on the scale of 10 to 30 nm while the laser light focusing is limited by diffraction effects and will likely stay on the scale of 100 to 1000 nm.

Equipment known in the art can be used to introduce delay between laser pulses. Accordingly, in some embodiments, the apparatus comprises an optical delay line to introduce delay between laser pulses. Examples of optical delay line suitable for use in the present invention are any of the optical delay lines commercially available from Thor-Labs.

Variable delay lines can be used to synchronise the arrival of the ionisation pulse with respect to the packet of primary ions or electrons, thus enabling the same laser to act in post-ionisation or pumping modes, depending of the relative timing of the packet of primary ions or electrons and the laser pulse.

Sample Chamber

The sample chamber of the sputtering-based sampling system shares many features in common with the sample chamber of the laser ablation-based sampling system discussed above. It comprises a stage to support the sample. The stage may be a translation stage, movable in the x-y or x-y-z axes. The sample chamber will also comprise an outlet, through which material removed from the sample by the laser radiation can be directed. The outlet is connected to the detector, enabling analysis of the sample ions.

In some instances, the sample chamber is held under 133322-13.3 Pa, such as 1333.22-133.322 Pa. In some instances, the sample chamber is held under a vacuum. Accordingly, in some instances, the sample chamber pressure is lower than 50000 Pa, lower than 10000 Pa, lower than 5000 Pa, lower than 1000 Pa, lower than 500 Pa, lower than 100 Pa, lower than 10 Pa, lower than 1 Pa, around 0.1 Pa or less than 0.1 Pa, such as 0.01 Pa or lower. For instance, partial vacuum pressure may be around 50-2000 Pa, 100-1000 Pa, or 200-700 Pa, and vacuum pressure lower than 10 Pa, 1 Pa, or 0.2 Pa. Suitable gasses include Argon, Helium, Nitrogen and mixtures thereof.

The selection of whether the sample pressure is at atmospheric pressure, partial vacuum pressure, or under vacuum depends on the particular analysis being performed, as will be understood by one of skill in the art. For instance, at atmospheric pressure, sample handing is easier, and softer ionisation may be applied. Further, the presence of gas molecules may be desired so as to enable the phenomenon of collisional cooling to occur, which can be of interest when the label is a large molecule, the fragmentation of which is not desired, e.g. a molecular fragment comprising a labelling atom or combination thereof. Alternatively, in instances where laser radiation is used to post-ionise material, the presence of gas molecules (e.g. at partial vacuum pressure) may be advantageous. For example, collisional cooling may allow the cooling of the nanoplasma generated at the surface of the sample (e.g., following charged particle bombardment or laser illumination of the sample to generate the energy pumping state) and expansion of the plume of ablated material and before re-ionization in a post-ionization system. Collisions may also allow for at least partial charge reduction, reducing space-charge effects and/or improving the ability of ion optics to direct ions. Charge state reduction to just a single charge per ion makes it easier to read out signals for different mass tags.

Holding the sample chamber under vacuum can prevent collisions between sample ions generated and other particles within the chamber.

The principal difference between the sample chamber of the SNMS system and the sample chamber of the laser ablation-based system is that the chamber is held under vacuum in order to prevent collisions between sample ions and other particles within the chamber, which could result in loss of charge from the ions—on a similar basis contrary to the laser ablation and desorption-based sample chambers. Loss of secondary ions would result in reduced sensitivity for the apparatus.

Ion Microscope

The sample ions are captured from the sample via an electrostatic lens positioned near to the sample, known in the art as an immersion lens (or an extraction lens). The immersion lens removes the secondary ions immediately from the locality of the sample. This is typically achieved by the sample and the lens having a large difference in voltage potential. Depending on the polarity of the sample vis-à-vis the immersion lens, positive or negative secondary ions are captured by the immersion lens. The polarity of the sample ions as captured by the immersion lens is independent of the polarity of the ions of the charged particle beam.

The sample ions are then transferred to the detector by via one or more further electrostatic lenses (known as transfer lenses in the art). The transfer lens(es) focus(es) the beam of secondary ions into the detector. Typically, in systems with multiple transfer lenses, only one transfer lens is engaged in a given analysis. Each lens may provide a different magnification of the sample surface. Commonly, further ion manipulation components are present between the immersion lens and the detector, for example one or more apertures, mass filters or sets of deflector plates. Together, the immersion lens, transfer lens, and any further components, form the ion microscope. Components for the production of an ion microscope are available from commercial suppliers e.g. Agilent.

Camera

The system may also comprise a camera. Camera systems are discussed above in relation to laser ablation sampling systems, and the features of the above camera can also be present in the secondary ion generation system, except where incompatible (e.g. it can be connected to a light microscope, such as a confocal microscope, but it is not possible to focus a primary ion beam through the same optics as the light which is directed to the camera, because one beam is ions and the other photons).

c. Two-Pulse Laser Based Sampling and Ionising System

Akin to certain apparatus, systems and techniques discussed in section 1.b. above, electron seeding to generate a 'sample ignition state' can be achieved at a location by a pulse of laser radiation. Subsequent to this, a second laser pulse with a laser spot diameter greater than the location, but with a fluence lower than the ablation threshold of the sample, can be directed at the sample to cause ablation only at the location targeted with the first laser pulse, as the energy needed to ablate the pre-seeded location is lower than the surrounding area. Thus, a tightly focused, low energy, first pulse can be used can be used to seed electrons, and a higher energy, less focused, pulse can be used to cause ablation at the location at which electrons were seeded. Thus, the invention provides yet a further means for high resolution imaging based upon this technique.

It is well known optical behaviour that the minimum spot size generated by an optical system is directly proportional to the wavelength of the light and inversely proportional to the numerical aperture of the objective. Since the wavelength of visible light is around 500 nm and numerical aperture of typical objectives rarely exceeds 1.0, the size of the focusing spot with such light ends up just below one micrometer. Accordingly, by operating with a shorter wavelength laser, the light can be focused to a smaller spot on the sample. For example, a VUV light with a wavelength around 200 nm can be generated by excimer lasers. Moreover, modern lithography tools employ EUV light with a wavelength of 13.5 nm. Unfortunately, generation of VUV and EUV light pulse with the energy sufficient for ablation requires a large, complex and expensive apparatus.

The invention solves the problem of ablation spot reduction by pre-seeding the spot to be ablated with a small amount of UV, EUV or XUV light. This pre-seeding generates free electrons in the otherwise dielectric material. This change in material properties lowers the threshold for ablation by a subsequent pulse. The amount of energy needed for the pre-seeding is many orders of magnitude lower than the amount of energy needed for direct ablation. This makes the equipment for generating such pulse relatively economical. The pre-seeding pulse can be focussed to 100 or 30 nm diameter because of its short wavelength. Shortly after the pre-seeding is done a pulse with a more common wavelength such as IR or Visible is sent to the same sample. It deposits its energy much more efficiently in the pre-seeded area. As a result, the pre-seeded area can be ablated while the rest of the area covered by the IR light won't be ablated. Thus, the size of ablation spot is controlled by the diffraction limit imposed by the UV, VUV, EUV wavelength. This limit is substantially lower than the ablation resolution of a Visible or IR light applied on its own.

In addition, this invention can lead to ionization of ablated material. Ion composition of ablated material can be analyzed and provide imaging mass spectrometry or imaging mass cytometry workflow. The material being ablated will be ionized in a plasma leading to a significant fraction of elemental ions being generated. Efficiency of ionization and ion sampling from the plasma can become high enough to facilitate single copy detection of antibodies when utilizing MaxPar reagents or similar reagents. Here, the ions can be extracted directly for analysis via the ion microscope as discussed below.

Several analytical problems exist when operation at such a high spatial resolution (e.g. 30 nm). One problem is the total acquisition rate vs the field of view (or region of interest) dimensions. An existing Hyperion operates at 200 pixels/s with 1 micrometer pixel size. This results in ~5000 seconds needed to record an image of a biologically relevant ROI with 1×1 mm scale. If the pixel size is reduced 30 times (to ~30 nm) then the amount of time would grow to 500000 s to record an image from a similar area. It is obviously, an impractically long time. This invention solves this problem by operating ionization sampling in at least a partial vacuum (see discussion of sample chamber below for further details) where the pixel rate can be as high as 1 Mpixels/s which means the 1×1 mm area will be acquired in just 100 seconds. Multiple serial sections can be analyzed to provide 3D images on a biological scale of around 0.03 mm. It will take 1000 sections (30 nm each) and ~1 day of experiment. This is a very high speed considering the multiparametric and high spatial resolution nature of the data obtained. If acquisition rate is increased to 10 Mpixels/s the collection of such images will be permitted within 2.5 hours. Sample analysis will also go ~30× faster at the spatial resolution of 100 nm.

As noted above, the use of MaxPar reagents (mass tagged antibody reagents, as discussed below) can compensate for sensitivity loss due to the smaller ablations by having ~100 atoms per a copy of one antibody. Ion sampling and transmission above 5% enables detection of a single copy of antibody. When an object is imaged with a pixel size of 30 nm only a very few antibodies can be found in such pixel. Therefore, it becomes vital to enable single copy detection for imaging at such a small scale.

The plasma generated by the two-pulse technique of the invention can solve the problem of efficient ionization and sampling. The small scale of ablation leads to the small scale of plasma which in turn reduces the probability of plasma neutralization during ion sampling. Moreover, the density of the solid material being ablated leads to initial plasma pressure on the scale 10000 atm which in turn leads to a local thermal equilibrium model of the plasma. The local thermal equilibrium permits generation of an optimum plasma temperature to facilitate near 100% efficient ionization of labelling atoms from mass tags to form elemental ions, controllable via the parameters of the second pulse.

A two-pulse laser ablation system based apparatus typically comprises three components. The first component is a first laser source for seeding electrons in a sample (which would be housed on the sample stage in the apparatus and systems disclosed herein). The second component is a second laser source for ablating the sample where electrons have been seeded by the first laser source. (Together, these two components form a two-pulse laser sampling and ionisation system.) The third component is a detector component that detects the ionised material, for instance a mass detector. The laser sources are typically pulsed. In some instances, the first (pre-seeding) pulse can be derived from the same laser that delivers the second (ablating) pulse, for instance by means of harmonics generation. The mentions in this section of directing a laser beam towards/at a location on the sample stage refers to the arrangement of the components in the apparatus and system, but as will be appreciated by one in the art, when the apparatus/system is being used to analyse a sample, the laser radiation from the first and second laser sources will impinge upon the sample under analysis.

Accordingly, the invention provides an apparatus for analysing a sample, such as a biological sample, comprising:
  a sample stage;
  a first laser source, configured to seed electrons in a sample, and first focusing optics configured to direct a laser beam emitted by the first laser source towards the sample stage; and
  a second laser source, configured to ablate sample material pre-seeded with electrons by the first laser source, and second focusing optics configured to direct a laser beam emitted by the second laser source towards the sample stage.

The apparatus typically comprises a mass detector, such as a TOF detector.

Accordingly, the invention provides a two-pulse laser sampling and ionisation system for analysing a sample, such as a biological sample, comprising:
  a sample stage;
  a first laser source, configured to seed electrons in a sample, and first focusing optics configured to direct a laser beam emitted by the first laser source towards the sample stage; and
  a second laser source, configured to ablate sample material pre-seeded with electrons by the first laser source, and second focusing optics configured to direct a laser beam emitted by the second laser source towards the sample stage.

In some embodiments, the first focusing optics configured to direct a laser beam emitted by the first laser source towards the sample stage is configured to direct a laser beam emitted by the first laser source to a location on the sample stage, and the second focusing optics configured to direct a laser beam emitted by the second laser source towards the sample stage is configured to direct a laser beam emitted by second first laser source to the location on the sample stage.

For instance, the invention provides an apparatus for analysing a sample, such as a biological sample, comprising:
  a sample stage;
  a first laser source, configured to seed electrons in a sample, and first focusing optics configured to direct a laser beam emitted by the first laser source towards a location on the sample stage; and
  a second laser source, configured to ablate sample material pre-seeded with electrons by the first laser source, and second focusing optics configured to direct a laser beam emitted by the second laser source towards the location on the sample stage.

The apparatus typically comprises a mass detector, such as a TOF detector.

For instance, the invention provides a two-pulse laser sampling and ionisation system for analysing a sample, such as a biological sample, comprising:
  a sample stage;
  a first laser source, configured to seed electrons in a sample, and first focusing optics configured to direct a laser beam emitted by the first laser source towards a location on the sample stage; and
  a second laser source, configured to ablate sample material pre-seeded with electrons by the first laser source, and second focusing optics configured to direct a laser beam emitted by the second laser source towards the location on the sample stage.

Figure 13:
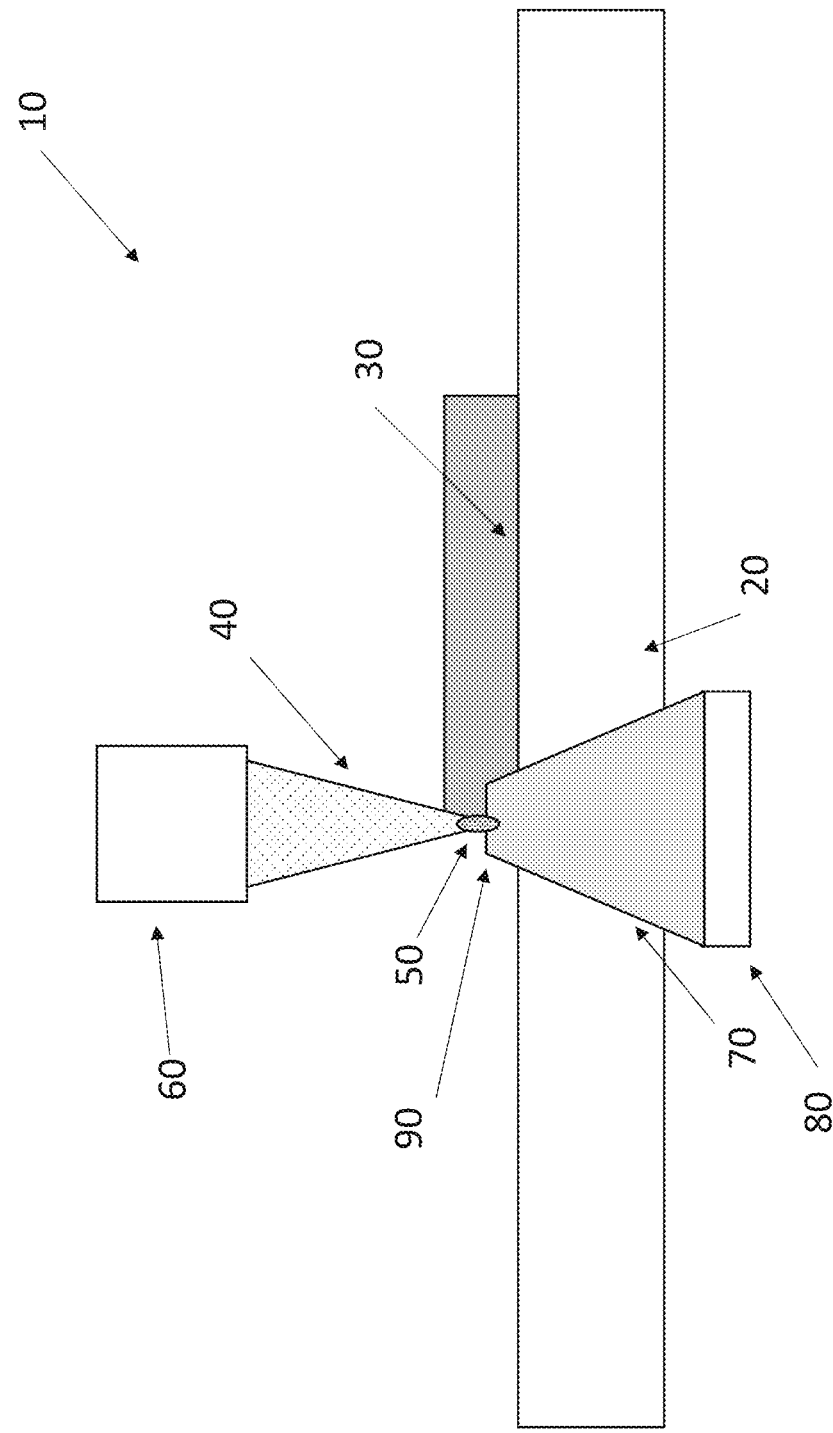
FIG. 13 is a schematic diagram of a two-pulse sampling and ionization system.

FIG. 13 is a schematic diagram of the arrangement of an exemplary embodiment of the invention that demonstrates reduction of the ablation spot size by two pulse ablation. A support target 20 holds a thin section of the specimen 30. In some embodiments (e.g. nano-machining applications) the support target and the specimen can be one body. A pulse of UV, or VUV or EUV or even XUV light 40 is focused 50 on the specimen 30 by an objective 60. Special objectives for UV, VUV, EUV optics are known in the art and are often based on reflective optical arrangements. The pulse of e.g. EUV light creates a seed of free electrons in the focal spot. Since the sample is generally non-conductive, pre-seeding with free electrons alters the properties on material in the focal spot of the laser. A second pulse of light 70 is sent to the same area, encompassing the location in which electrons were pre-seeded, to supply the energy to develop plasma in the preseeded location. The second pulse of light 70 is sent by another objective 80. Due to a significantly longer wavelength of the second pulse the focal spot 90 of the second pulse is much larger than the focal spot of the first pulse. The process by which electrons multiply in the specimen during the second pulse can be called avalanche ionization. In practice, many phenomena can contribute to the preferential excitation of the pre-seeded area. As long as the energy required for the preferential excitation is substantially lower than the threshold for direct ablation the scheme of defining ablation zone by the pre-seeding with the e.g. EUV pulse is effective.

Accordingly, the invention provides an apparatus and systems for analysing a sample, such as a biological sample, wherein the second focusing optics is configured to synchronise a second pulse, of laser radiation from the second laser source, to arrive at the location on the sample stage directly after a pulse of laser radiation from the first laser source Accordingly, the invention provides an apparatus for analysing a sample, such as a biological sample, comprising:
  a sample stage;
  a first laser source, configured to seed electrons in a sample, and first focusing optics configured to direct a laser beam emitted by the first laser source towards the sample stage; and
  a second laser source, configured to ablate sample material pre-seeded with electrons by the first laser source, and second focusing optics configured to direct a laser beam emitted by the second laser source towards the sample stage;
  wherein the second focusing optics is configured to synchronise a second pulse, of laser radiation from the second laser source, to arrive at the location on the sample stage directly after a pulse of laser radiation from the first laser source, The apparatus typically comprises a mass detector, such as a TOF detector.

Accordingly, the invention provides a two-pulse laser sampling and ionisation system for analysing a sample, such as a biological sample, comprising:
  a sample stage;
  a first laser source, configured to seed electrons in a sample, and first focusing optics configured to direct a laser beam emitted by the first laser source towards the sample stage; and
  a second laser source, configured to ablate sample material pre-seeded with electrons by the first laser source, and second focusing optics configured to direct a laser beam emitted by the second laser source towards the sample stage;
  wherein the second focusing optics is configured to synchronise a second pulse, of laser radiation from the second laser source, to arrive at the location on the sample stage directly after a pulse of laser radiation from the first laser source, In some embodiments, the first focusing optics configured to direct a laser beam emitted by the first laser source towards the sample stage is configured to direct a laser beam emitted by the first laser source to a location on the sample stage, and the second focusing optics configured to direct a laser beam emitted by the second laser source towards the sample stage is configured to direct a laser beam emitted by second first laser source to the location on the sample stage.

Accordingly, the invention provides an apparatus and systems for analysing a sample, such as a biological sample, wherein the first focusing optics and second focusing optics are configured to direct laser radiation to opposite sides of the sample stage.

Accordingly, the invention provides an apparatus for analysing a sample, such as a biological sample, comprising:
  a sample stage comprising a first face and a second face, the first and second faces being opposed, and wherein the first face is adapted to receive a sample;
  a first laser source, configured to seed electrons in a sample, and first focusing optics configured to direct a laser beam emitted by the first laser source towards the first face of the sample stage; and
  a second laser source, configured to ablate sample material pre-seeded with electrons by the first laser source, and second focusing optics configured to direct a laser beam emitted by the second laser source towards the second face of the sample stage;
  wherein the second focusing optics is configured to synchronise a second pulse, of laser radiation from the second laser source, to arrive at the location on the sample stage directly after a pulse of laser radiation from the first laser source.

The apparatus typically comprises a mass detector, such as a TOF detector.

Accordingly, the invention provides a two-pulse laser sampling and ionisation system for analysing a sample, such as a biological sample, comprising:
  a sample stage comprising a first face and a second face, the first and second faces being opposed, and wherein the first face is adapted to receive a sample;
  a first laser source, configured to seed electrons in a sample, and first focusing optics configured to direct a laser beam emitted by the first laser source towards the first face of the sample stage; and
  a second laser source, configured to ablate sample material pre-seeded with electrons by the first laser source, and second focusing optics configured to direct a laser beam emitted by the second laser source towards the second face of the sample stage;
  wherein the second focusing optics is configured to synchronise a second pulse, of laser radiation from the second laser source, to arrive at the location on the sample stage directly after a pulse of laser radiation from the first laser source.

The invention also provides an apparatus for analysing a sample, such as a biological sample, comprising:
  a sample stage comprising a first face and a second face, the first and second faces being opposed, and wherein the first face is adapted to receive a sample;
  a first laser source, configured to seed electrons in a sample, and first focusing optics configured to direct a laser beam emitted by the first laser source towards the second face of the sample stage; and
  a second laser source, configured to ablate sample material pre-seeded with electrons by the first laser source, and second focusing optics configured to direct a laser beam emitted by the second laser source towards the first face of the sample stage;
  wherein the second focusing optics is configured to synchronise a second pulse, of laser radiation from the second laser source, to arrive at the location on the sample stage directly after a pulse of laser radiation from the first laser source.

The apparatus typically comprises a mass detector, such as a TOF detector.

Accordingly, the invention provides a two-pulse laser sampling and ionisation system for analysing a sample, such as a biological sample, comprising:
  a sample stage comprising a first face and a second face, the first and second faces being opposed, and wherein the first face is adapted to receive a sample;
  a first laser source, configured to seed electrons in a sample, and first focusing optics configured to direct a laser beam emitted by the first laser source towards the second face of the sample stage; and
  a second laser source, configured to ablate sample material pre-seeded with electrons by the first laser source, and second focusing optics configured to direct a laser beam emitted by the second laser source towards the first face of the sample stage;

wherein the second focusing optics is configured to synchronise a second pulse, of laser radiation from the second laser source, to arrive at the location on the sample stage directly after a pulse of laser radiation from the first laser source.

Figure 14:
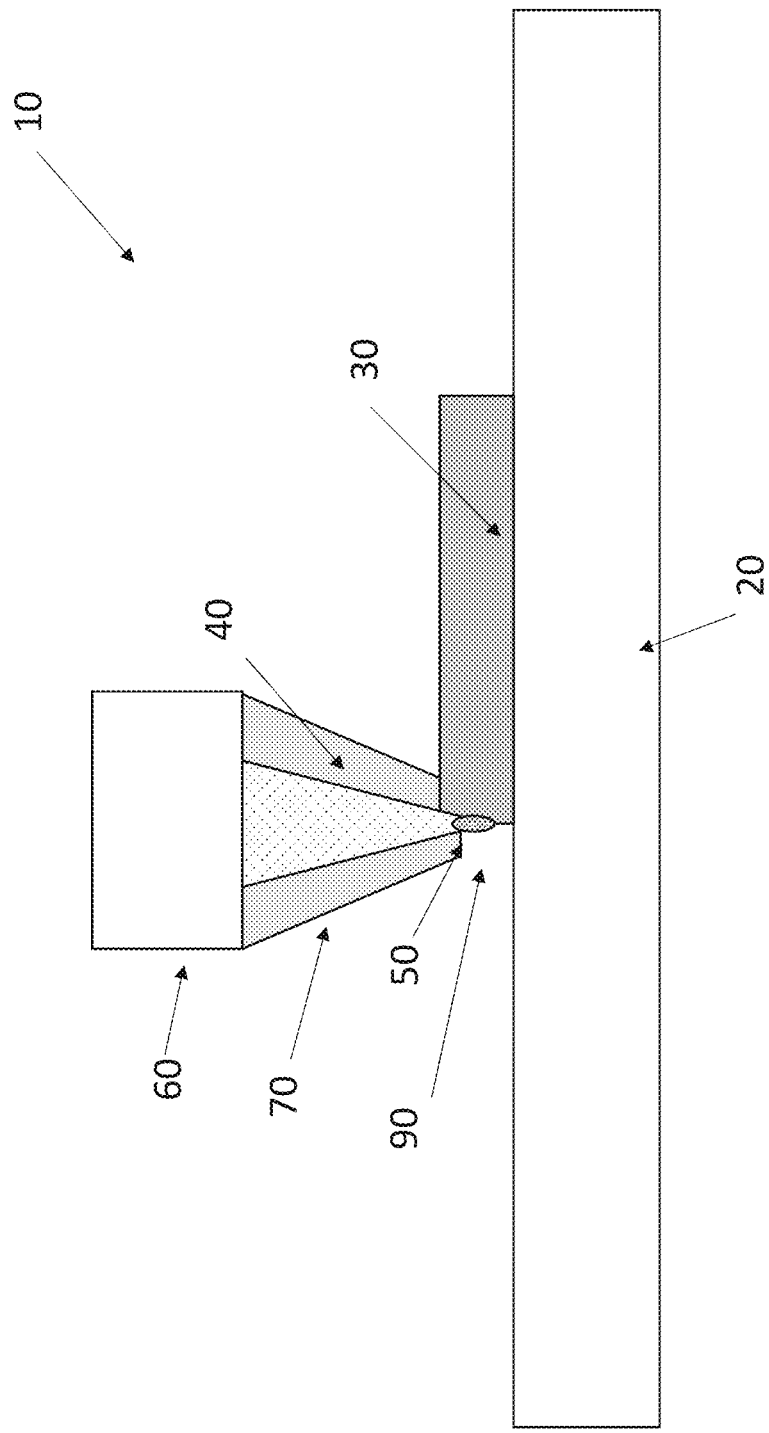
FIG. 14 is a schematic diagram of a two-pulse sampling and ionization system in which the first and second pulse are focused onto the specimen from the same side.

FIG. 14 shows another preferred embodiment for invention. Here, the first pulse 40 and the second pulse 70 are focused onto the specimen from the same side. A single objective 60 is used to combine and focus two light pulses. Accordingly, the invention provides an apparatus and systems for analysing a sample, such as a biological sample, wherein the first focusing optics and second focusing optics are configured to direct laser radiation to opposite sides of the sample stage.

Accordingly, the invention provides an apparatus for analysing a sample, such as a biological sample, comprising:
- a sample stage comprising a first face and a second face, the first and second faces being opposed, and wherein the first face is adapted to receive a sample;
- a first laser source, configured to seed electrons in a sample, and first focusing optics configured to direct a laser beam emitted by the first laser source towards the first face of the sample stage; and
- a second laser source, configured to ablate sample material pre-seeded with electrons by the first laser source, and second focusing optics configured to direct a laser beam emitted by the second laser source towards the first face of the sample stage;
- wherein the second focusing optics is configured to synchronise a second pulse, of laser radiation from the second laser source, to arrive at the location on the sample stage directly after a pulse of laser radiation from the first laser source;
- and wherein the first focusing optics and second focusing optics use the same objective lens to focus radiation from the first and second laser sources.

The apparatus typically comprises a mass detector, such as a TOF detector.

Accordingly, the invention provides a two-pulse laser sampling and ionisation system for analysing a sample, such as a biological sample, comprising:
- a sample stage comprising a first face and a second face, the first and second faces being opposed, and wherein the first face is adapted to receive a sample;
- a first laser source, configured to seed electrons in a sample, and first focusing optics configured to direct a laser beam emitted by the first laser source towards the first face of the sample stage; and
- a second laser source, configured to ablate sample material pre-seeded with electrons by the first laser source, and second focusing optics configured to direct a laser beam emitted by the second laser source towards the first face of the sample stage;
- wherein the second focusing optics is configured to synchronise a second pulse, of laser radiation from the second laser source, to arrive at the location on the sample stage directly after a pulse of laser radiation from the first laser source; and
- wherein the first focusing optics and second focusing optics use the same objective lens to focus radiation from the first and second laser sources.

Figure 15:
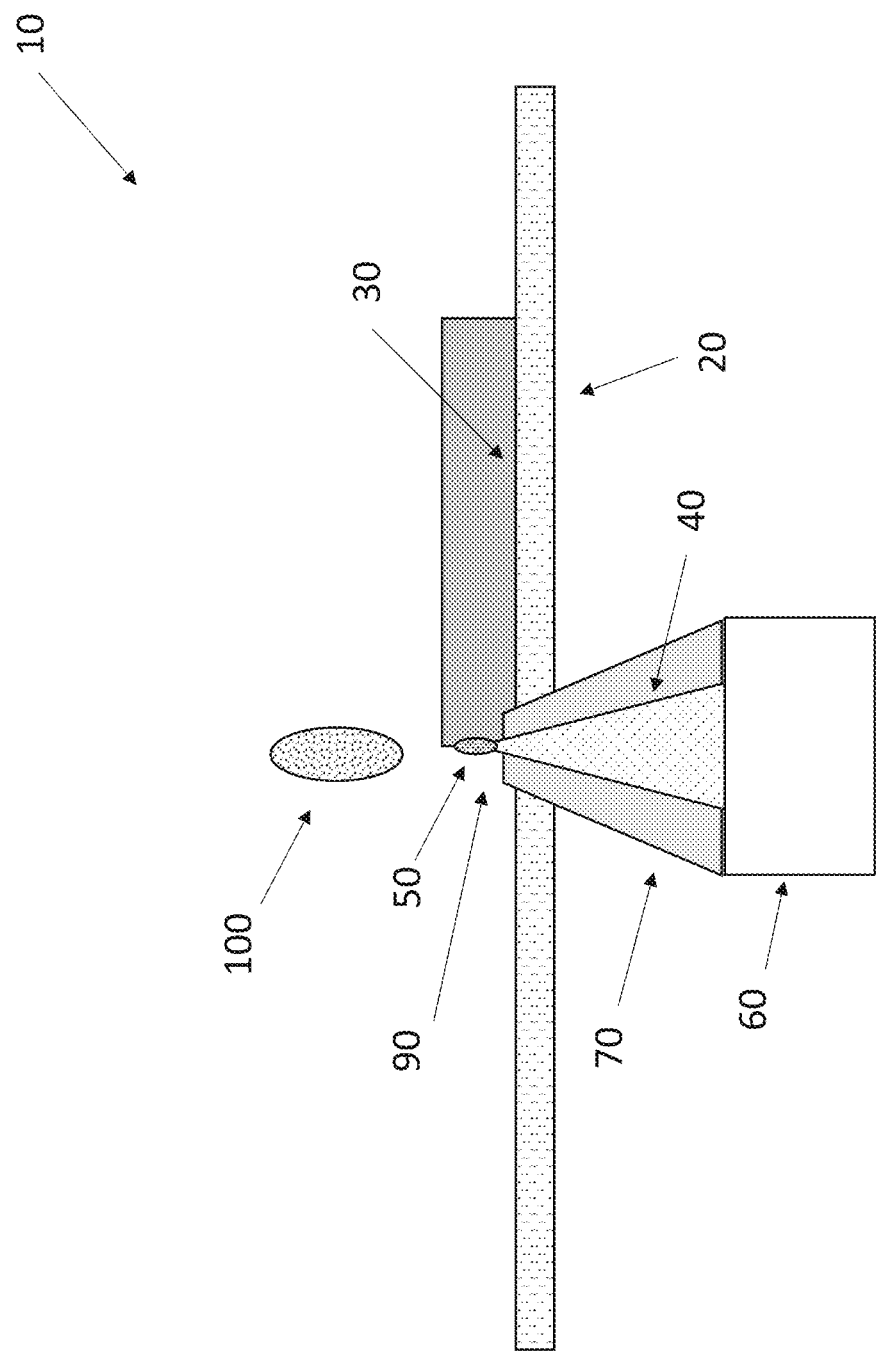
FIG. 15 is a schematic diagram of a two-pulse sampling and ionization system in which the sample is resting on a material that is at least semi-transparent to the first and second pulse.

FIG. 15 shows yet another embodiment where the sample (30) is resting on a material that is at least semi-transparent to the first pulse and even more transparent to the second pulse. This material may be in the form of a metal mesh used in electron microscopy. This geometry allows for the ablated plasma to expand into a cloud 100 of ions, electrons and neutral material. The ions here can be sampled into a mass spectrometer for imaging mass spectrometry an imaging mass cytometry applications.

Accordingly, in some embodiments of the two-pulse laser based apparatus and sampling and ionisation system disclosed herein, the sample stage is at least in part composed of a material at least semi-transparent to the laser radiation from the first laser source and even more transparent to radiation from the second laser source. Alternatively, as explained elsewhere herein, and reiterated here for completeness, when the laser radiation is directed through the sample stage to reach a sample on the first face, the sample stage should include a void through which laser radiation can pass to reach the sample (through the sample carrier). In the situation where the sample stage comprises a void, the sample is placed on a sample carrier that is at least in part composed of a material at least semi-transparent to radiation from the first laser source and even more transparent to radiation from the second laser source.

Figure 16:
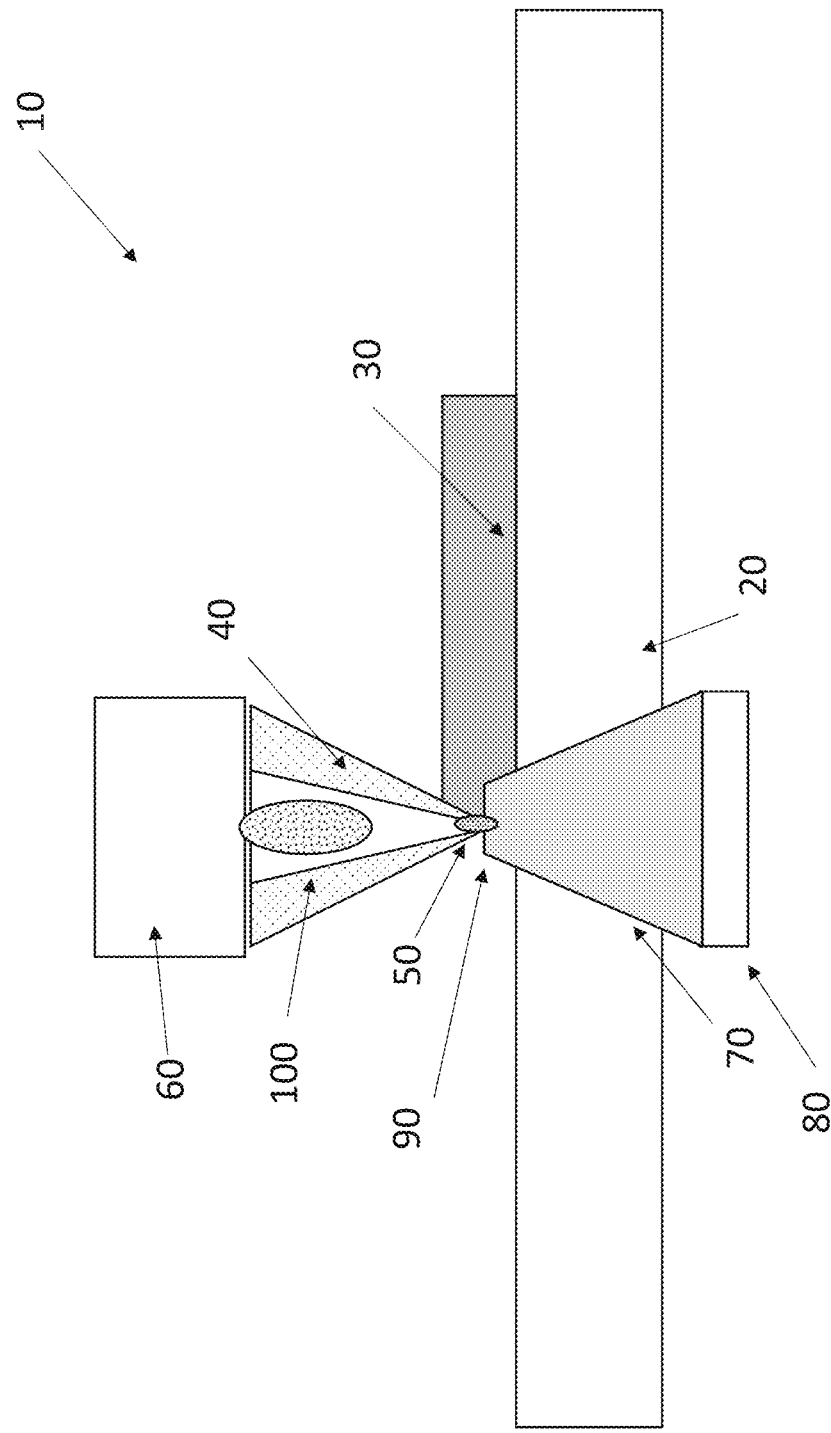
FIG. 16 is a schematic diagram of a two-pulse sampling and ionization system in which the objective has an opening to allow passage of ions generated after ablation.

FIG. 16 shows another embodiment that facilitates efficient sampling of ablated ions. Here the first laser pulse 40 is sent from the first side. The first laser pulse is formed by an objective 60 that has an opening in the middle to allow for the passage of ions 100 generated after the ablation.

Accordingly, in some embodiments of the two-pulse laser based apparatus and sampling and ionisation system disclosed herein, the objective of the first focusing optics has an opening in the middle to allow for the passage of ionized material from a sample through the opening.

Components of Two-Laser Sampling and Ionisation System

First Laser Source—Lasers for Pre-Seeding Electrons

As set out above, the requirement to achieve high resolution imaging is a wavelength of laser radiation that can be focused to a focal spot of 100 nm diameter or smaller. Accordingly, the wavelength of laser radiation emitted by the first laser source must be UV light. In some embodiments, the laser radiation emitted by the first laser source is UV, VUV, EUV or XUV. In some embodiments, the laser radiation emitted by the first laser source is 200 nm or shorter, 175 nm or shorter, 150 nm or shorter, 125 nm or shorter, 100 nm or shorter, 75 nm or shorter, 50 nm or shorter, 25 nm or shorter, 20 nm or shorter or 15 nm. For instance, in some embodiments, the laser radiation emitted by the first laser source is between 10-200 nm, between 10-175 nm, between 10-150 nm, between 10-125 nm, between 10-100 nm, between 10-75 nm, between 10-50 nm, between 10-25 nm, between 10-20 nm, or between 10-15 nm.

In line with the discussions above, the pulse energy of the first laser source is chosen such that it seeds electrons in a material but does not ablate the material. In some embodiments, the pulse energy of the first laser source is in the picoJ to femtoJ range. For instance between 1 picoJ-100 femtoJ, between 10 picoJ-100 femtoJ, or between 100 picoJ-1 femtoJ.

The duration of the pulse must be short enough to minimise diffusion of the seeded electrons prior to the second laser pulse that causes ablation of the sample. The total time between the start of the first pulse (from the first laser source) and end of the second (from the second laser source) should be kept below 10 ps. Accordingly, in some embodiments, the duration of a pulse from the first laser source is 5 µs or shorter, such as 2 µs or shorter, 1 µs or shorter, 500 fs or shorter, 400 fs or shorter, 300 fs or shorter, 200 fs or shorter or 100 fs or shorter, 50 fs or shorter, 40 fs or shorter, 30 fs or shorter, 20 fs or shorter or 10 fs or shorter.

First Focusing Optics

The first focusing optics direct the radiation from the first laser source to the sample, and focus it onto the sample. To achieve high resolution imaging, the first focusing optics must focus the laser radiation to a spot size at the sample of around 100 nm or shorter, such as 75 nm or shorter, 50 nm or shorter or around 30 nm.

In some embodiments, the objective lens of the first focusing optics is a reflective objective.

Second Laser Source—Lasers for Ablation of Pre-Seeded Sample Locations

The requirements for the second laser source in the system differ because of its different function. The pulse of laser radiation from the second laser source supplies the energy to develop the plasma at the sample and to control its temperature.

Accordingly, the wavelength of laser radiation emitted by the second laser source can be IR or visible light. If visible light is emitted by the second laser source, it can be focused tighter and will therefore require less energy per pulse for ablation. In some embodiments, the laser radiation emitted by the second laser source is 400 nm or longer, 500 nm or longer, 600 nm or longer, 700 nm or longer, 800 nm or longer, or 1 µm or longer. For instance, in some embodiments, the laser radiation emitted by the second laser source is between 400 nm-100 µm, such as between 200 nm-100 µm, between 200 nm-10 µm, between 200 nm-1 µm, between 400 nm-10 µm, between 400 nm-1 µm, between 400 nm-900 nm, between 400 nm-800 nm, between 400 nm-700 nm, between 400 nm-600 nm or between 500 nm-600 nm.

In line with the discussions above, the pulse energy of the second laser source is chosen such that it ablates only the sample material in the laser spot that has been pre-seeded with electrons—i.e. the pulse fluence is below the ablation threshold of the material. In some embodiments, the pulse energy of the second laser source is in the nanoJoule range. For instance between 1 nanoJ-1 pJ, between 10 nanoJ-500 nanoJ, between 50 nanoJ-250 nanoJ, or around 100 nanoJ.

The duration of the pulse must be short enough to minimise diffusion of the seeded electrons prior to the second laser pulse that causes ablation of the sample. The total time between the start of the first pulse (from the first laser source) and end of the second (from the second laser source) should be kept below 10 µs. Accordingly, in some embodiments, the duration of a pulse from the second laser source is 5 µs or shorter, such as 2 µs or shorter, 1 µs or shorter, 500 fs or shorter, 400 fs or shorter, 300 fs or shorter, 200 fs or shorter or 100 fs or shorter, 50 fs or shorter, 40 fs or shorter, 30 fs or shorter, 20 fs or shorter or 10 fs or shorter.

Second Focusing Optics

The second focusing optics direct the radiation from the second laser source to the sample, and focus it onto the sample. High resolution imaging is achieved by the tightness of the focusing of the first short wavelength pulse, accordingly the spot size may be bigger than the first pulse. Nonetheless, a relatively small spot size minimises the irradiation of sample around the seeded location. Accordingly, in some embodiments, the second focusing optics focus the laser radiation to a spot size at the sample of around 2 µm or shorter, such as 1 µm or shorter, 750 nm or shorter, 500 nm, 250 nm or shorter, 200 nm or shorter, 150 nm or shorter or around 100 nm.

In some embodiments, the objective lens of the second focussing optics is a refractive or reflective objective, such as a lens with an NA above 0.7, above 0.8 or above 0.9. In some embodiments, the objective lens of the second focussing optics is also the objective lens of the first focussing optics as discussed above.

Synchronisation of First and Second Laser Sources

The apparatus of the present invention may use different lasers for the first and second laser source. Here, techniques routine in the art, such as programmed module comprising instructions can be used to co-ordinate delivering of a first pulse, from the first laser source, and a second pulse, from the second laser source, to the sample, such that pre-seeding and ablation of the pre-seeded area occur in line with the discussions above. In some embodiments, the first and second pulses are synchronised such that the time elapsed from the start of the pulse from the first laser source to the end of the pulse from the second laser source has a duration less than 50 ps, such as shorter than 25 ps. In some embodiments, the time is shorter than 10 ps, such as shorter than 5 ps, shorter than 2 ps, or shorter than 1 ps, In some embodiments, the apparatus and systems use one laser for the first and second laser source and a beam splitter to split the laser and provide the first and second laser sources.

For instance, a single laser engine that generates an IR pulse can be used. The pulse can be converted into visible light by a second or third harmonic generator. To generate short wavelength radiation for the first pulse, the laser can be coupled into a high-harmonics generation stage. Optical delay lines can be employed control time separation between the first and the second pulse as well as beyond the second and the third pulse.

Accordingly, in some embodiments, the apparatus or sampling system comprising a first laser source and a second laser source comprises a single laser, beam splitter, and two harmonics generators, wherein one of the harmonics generators is adapted to produce UV, VUV, EUV or XUV laser radiation (as discussed above for the first laser source) from the single laser as a first laser source, and the other of the harmonics generators IR or visible wavelength laser radiation (as discussed above for the second laser source) from the single laser as a second laser source.

Accordingly, in some embodiments, the apparatus or sampling system comprising a first laser source and a second laser source comprises a single laser, beam splitter, two harmonics generators, and an optical delay line, wherein one of the harmonics generators is adapted to produce UV, VUV, EUV or XUV laser radiation (as discussed above for the first laser source) from the single laser as a first laser source, and the other of the harmonics generators is adapted to produce IR or visible wavelength laser radiation (as discussed above for the second laser source) from the single laser as a second laser source; and wherein the optical delay line is adapted so as to deliver a pulse from the second laser source derived from a pulse of the single laser after the pulse from the first laser source derived from the same pulse of the single laser, such that the end of the second pulse is shorter than 50 ps following the start of the first pulse, such as shorter than 25 ps, shorter than 10 ps, such as shorter than 5 ps, shorter than 2 ps, or shorter than 1 ps.

Optionally, the output of the harmonics generator adapted to produce UV, VUV, EUV or XUV laser radiation can be filtered out to contain the range of the wavelengths that are of interest for pre-seeding the area to be ablated.

A magnetic sector instrument is probably more suited for high rate of recording of 1 Mpixel and above. For the rate of recording of 100 kpixels/s a Time-Of-Flight mass analyzer is suitable and might be simpler to design and build.

Because the ion source of this type produces a very tight ion spot the properties of the ion beam in this technique make the ion beam suitable for many types of mass analyzers (known at present and to be invented).

General Laser Considerations

The femtosecond laser may be a solid state laser. Passively mode-locked solid-state bulk lasers can emit high-quality ultrashort pulses with typical durations between 30 fs and 30 ps. Examples of such lasers include diode-pumped lasers, such as those based on neodymium-doped or ytterbium-doped crystals. Titanium—sapphire lasers can be used for pulse durations below 10 fs, in extreme cases down to approximately 5 fs (e.g. Octavius Ti:Sapphire Lasers, available from Thorlabs). The pulse repetition rate is in most cases between 1 kHz and 500 MHz.

The femtosecond laser may be a fiber laser. Various types of ultrafast fiber lasers, which may also be passively mode-locked, typically offer pulse durations between 50 and 500 fs, repetition rates between 0.10 and 100 MHz, and average power between a few milliwatts and several watts (femtosecond fiber lasers are commercially available from Toptica, IMRA America, Coherent, Inc.). Femtosecond fiber lasers are particularly suitable for this application. The lasers are reasonably priced when the energy output is <1 uJ. The repetition rate of laser pulses is >1 MHz potentially leading to the acquisition rate of 1 Mpixel/s. The pulse duration of such lasers ~200 fs is well within the upper limit of 10 µs dictated by diffusion broadening of the plasma area.

The femtosecond laser may be a semiconductor laser. Some mode-locked diode lasers can generate pulses with femtosecond durations. Directly at the laser output, the pulses durations are usually at least several hundred femtoseconds, but with external pulse compression, much shorter pulse durations can be achieved.

In some embodiments, the laser is a nanosecond laser. The nanosecond laser can be a pumped laser such as the Quantel Q-smart DPSS, the Solar Laser LQ929 high power pulsed Nd:YAG laser, or the Litron High Energy Pulsed Nd:YAG laser. All of these lasers can produce deep ultraviolet radiation within the mJ regime so suitable for ionisation and with short pulse durations.

It is also possible to passively mode-lock vertical external-cavity surface-emitting lasers (VECSELs); these are interesting particularly because they can deliver a combination of short pulse durations, high pulse repetition rates, and sometimes high average output power, whereas they are not suitable for high pulse energies.

Figure 17:
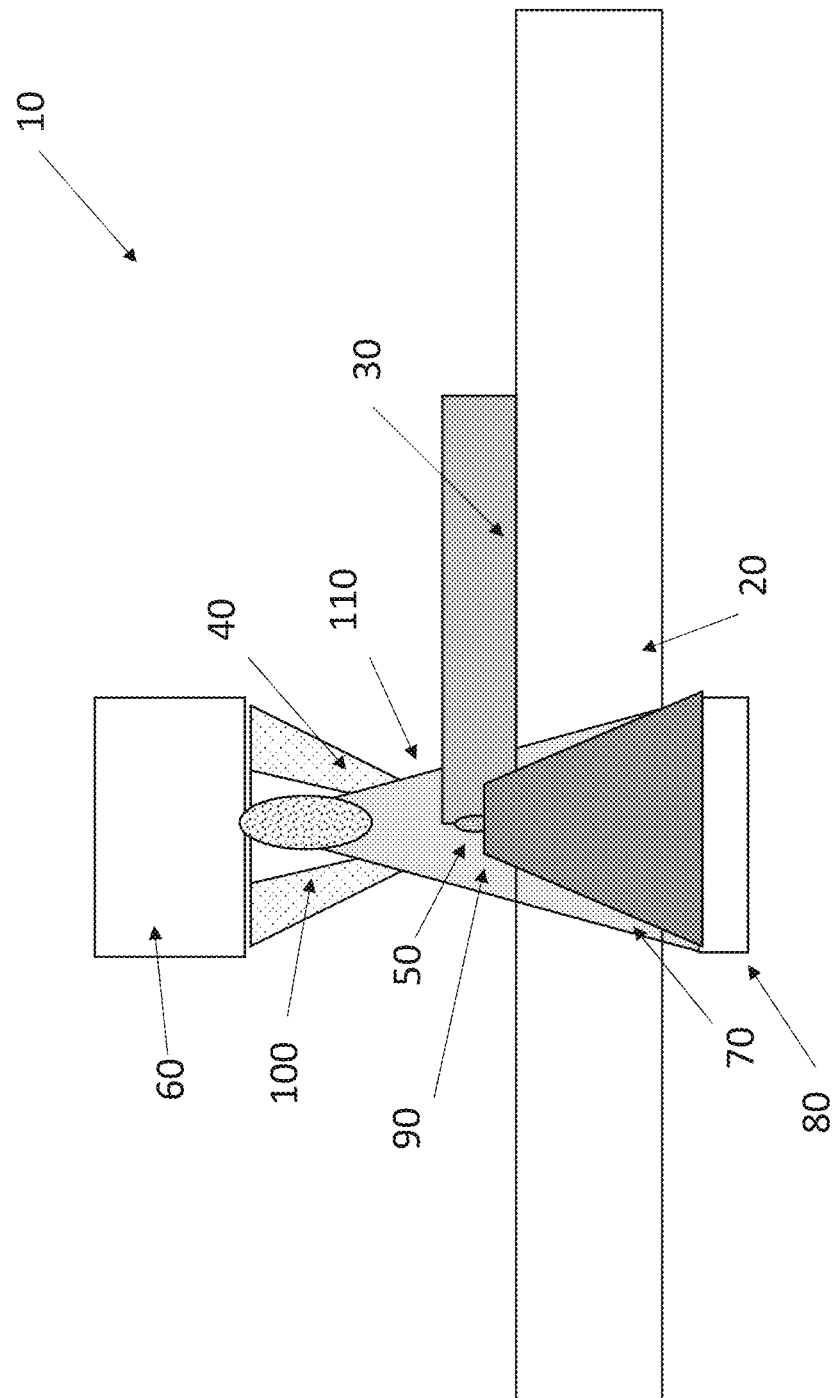
FIG. 17 is a schematic diagram of a three-pulse sampling and ionization system.

Post Ionisiation in Two-Pulse Laser Ablation Based Sampling Systems and Apparatus FIG. 17 shows an embodiment where three laser pulses are used to provide ablation and post-ionization. Here the first two pulses 40 and 70 are used to ablate material on the small scale similar to the embodiment of FIG. 13. The third pulse 110 is sent to overlap with the plume of ablated material. It is used to provide further ionization for this material. This step could be necessary to suppress effects of neutralization that can occur in the ablated plume. The ions are then extracted through the opening (not shown) in the objective 60.

Post-ionisation requires a high energy density from the laser radiation in a small volume, e.g. 5 µm$^3$ or less. Because the post ionization volume is so small it sets the limit on the amount of material that can be ionized in one go. If a large amount of positive and negative charges is created in a small volume the motion of the ions formed will be dominated by the local fields resulting from the space charge induced by the ions and electrons. If there are too many charged ions in a small volume, external fields, such as the fields from ion optics present in mass spectrometers used to direct the resulting ions to the detector for detection, will not be effective at separating positive and negative charges and such ion clouds will eventually neutralise reducing ionisation efficiency. For example, an ion cloud on a scale of 10 µm (in diameter) containing 10000 elemental charges creates an electrostatic potential that is about 3 V. Since a few eV is the energy holding the electrons to the atoms it is also the likely energy level of free electrons after ionisation. As a result, the ion density on the scale of 10000 ions in a volume on the 10 micrometer scale is near the limit where the space charge behaviour starts to dominate.

Accordingly, such effects can be avoided by ensuring that the amount of ablated material is kept reasonably small. For example, ablation of material on the scale of 10×10×10 nm cube to 30×30×30 nm cube or a similar volume represents the highest amount of material that can be transferred into the post ionization area of a few micrometers in size without creating a strong space change and ion neutralization. Since the system can only process 30×30×30 nm cube per single event this creates an opportunity to conduct the imaging with the spatial resolution of 30 nm or even 10 nm, to which ion beams can be focused (as discussed herein).

The post ionization laser beam/radiation is co-aligned with the beam of the second laser source to within a micrometer precision, as is commonly obtained in optical setups.

In some embodiments, the post-ionization laser beam/radiation is directed at an angle to the sample and into the previously ablated area of the specimen (the arrangement in FIG. 6 for a charged particle-based sampling and ionization system). This configuration minimizes the interaction between the laser radiation for post-ionization and the unablated specimen. The laser beam can be focused to a tight focus that overlaps with the volume of ablation plume. The laser beam focusing can be done at high numerical aperture (NA) to facilitate sharp focusing in the overlapping region and enable rapid laser energy spreading outside of the overlapping region to minimize the possibility of damage to the sample in the regions surrounding that being sampled.

In some embodiments, numerical aperture of the post-ionization laser beam/radiation may be constrained in one of the planes. Such an arrangement results in an elliptical focal spot that is extended in the plane of low NA. The elliptical focal spot may improve the degree of overlap with the sputtered/ablated plume. Accordingly, in some embodiments, the laser of the post-ionisation system has an elliptical focal spot.

In addition to spatial co-ordination, plume generation by the combined action of the first and second laser sources described above needs to be synchronised with the delivery of laser radiation to ionise the ablated material. The speed at which the ablated material may leave the target on the scale of the speed of sound i.e. 1000 m/s. Thus, to ensure alignment of the ablated plume and the post-ionization laser radiation/beam with 1 micrometer precision requires timing precision on the scale of 1 ns. In certain aspects, the velocity may be between 1 km/s and 10 km/s, such as between 2 km/s and 5 km/s, depending on the temperature and composition of ablated material. The ablation may be into atmospheric pressure, partial vacuum pressure, or vacuum pressure as described herein.

Thus, in this mode of operation, the first and second laser sources act together to ablate material from the sample, and very shortly after that, the ejected material is post-ionised by a pulse of laser radiation from a third laser source.

The nano-plasma generated by the action of the first and second lasers contains elemental ions, but where post-ionization is used, these ions are not extracted directly. Rather, the ejected plume is allowed to expand, during which time at least some charge neutralization occurs (because the plasma at that point is under high pressure and so dense, meaning that collisional cooling and charge reduction quite rapidly occurs. As noted above, the speed of expansion of the nanoplasma plume is around 1000-5000 m/s. Thus, after a few picoseconds, the plasma generated from ablation of e.g. a 10 nm diameter spot on the sample will have expanded by an order of magnitude, e.g. to a 100 nm$^3$ volume. Additional or re-ionization of the plume after a 10-100 fold dimensional expansion of the original nano-plasma volume means that the components of the original plume are now significantly more spread out, such that when ionized to reinstate a micrometer scale plasma, collisions are much less likely (and thus less likely charge neutralisation) and thus a higher proportion of elemental ions can be extracted from the plume. With higher efficiency extraction of ions, including elemental ions derived from labelling atoms, greater sensitivity is achieved.

Accordingly, in some embodiments, two-pulse laser based sampling and ablation systems and apparatus comprises a third laser source, configured to ionize plumes of sample material ablated from the sample.

Thus the invention provides a two-pulse laser sampling and ionisation system for analysing a sample, such as a biological sample, comprising:

a sample stage;
a first laser source, configured to seed electrons in a sample, and first focusing optics configured to direct a laser beam emitted by the first laser source towards the sample stage;
a second laser source, configured to ablate sample material pre-seeded with electrons by the first laser source, and second focusing optics configured to direct a laser beam emitted by the second laser source towards sample stage;
a third laser source, configured to ionize plumes of sample material ablated from the sample, and third focusing optics configured to direct a laser beam emitted by the third laser source to the volume in which ablated sample material forms a plume;
wherein the second focusing optics is configured to synchronise a second pulse of laser radiation, from the second laser source, to arrive at a location on the sample stage directly after the first pulse of laser radiation, from the first laser source; and
wherein the third focusing optics is configured to synchronise a third pulse of laser radiation to arrive at a volume above the location on the sample stage directly after the second pulse of laser radiation.

The third laser provide a fast pulse, an may be less than 30 ps, less than 10 ps, less than 1 ps, or less than 500 fs or less than 100 fs, such as at or between 1 fs and 10 ps, at or between 1 fs and 1 ps, at or between 1 fs and 500 ps, at or between 100 fs and 500 fs. In some embodiments, the first focusing optics configured to direct a laser beam emitted by the first laser source towards the sample stage is configured to direct a laser beam emitted by the first laser source to a location on the sample stage, and the second focusing optics configured to direct a laser beam emitted by the second laser source towards the sample stage is configured to direct a laser beam emitted by second first laser source to the location on the sample stage.

The discussion above of the volume to which the laser radiation from the third laser source refers to volume above the sample. This is the volume in which an ablation plume forms when material is ejected from the sample. Above is used in this scenario as a term relative to the sample, were the sample in a horizontal plane. If the sample were held in the vertical plane such that the plume following ablation were ejected in the horizontal axis, the volume "above the sample" to which the laser radiation from the third laser source would be lateral to the sample. In some embodiments the volume is 5 $\mu m^3$ or smaller, such as 2.5 $\mu m^3$ or smaller, 2 $\mu m^3$ or smaller, 1 $\mu m^3$ or smaller, or 100 $nm^3$ or smaller. In some embodiments the volume is 5 $\mu m^3$ or smaller, such as 2.5 $\mu m^3$ or smaller, 2 $\mu m^3$ or smaller, 1 $\mu m^3$ or smaller, or 100 $nm^3$ or smaller. In some embodiments, the volume extends less than 2 $\mu m$, such as less than 1 $\mu m$, or less than 100 nm from the surface of the sample.

As noted above, the first and second laser sources may represent discrete lasers or may be derived from the same single laser. Likewise, the third laser source may be a discrete laser or may be derived from (i) the same single laser as the first laser source; (ii) the same single laser as the first laser source or (iii) the first, second and third laser sources may all be derived from the same single laser.

Where different lasers are used, techniques routine in the art, such as programmed module comprising instructions can be used to co-ordinate delivering of the first and second pulses to the sample, such that pre-seeding and ablation of the pre-seeded area occur in line with the discussions above, and the pulse from the third laser source to the volume above the surface of the sample at the ablated location.

In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 100 ns after the end of the pulse from the second laser source, In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 10 ns after the end of the pulse from the second laser source, In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 1 ns after the end of the pulse from the second laser source, In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 100 ps after the end of the pulse from the second laser source, In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 50 ps after the end of the pulse from the second laser source. In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 30 ps after the end of the pulse from the second laser source. In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 $\mu$s, shorter than 2 ps, or shorter than 1 ps, and the pulse from the third laser source arrives a t the volume above the surface of the sample at the ablated location shorter than 20 ps after the end of the pulse from the second laser source. In some embodiments, the first and second pulses are synchronised such that the time elapsed from the start of the pulse from the first laser source to the end of the pulse from the second laser source has a duration less than 50 ps, such as shorter than 25 ps, shorter than 10 ps, such as shorter than 5 ps, shorter than 2 ps, or shorter than 1 ps, and the pulse from the third laser source arrives at the volume above the surface of the sample at the ablated location shorter than 10 ps after the end of the pulse from the second laser source.

Thus the invention provides a two-pulse laser sampling and ionisation system for analysing a sample, such as a biological sample, comprising:
 a sample stage;
 a first laser source, configured to seed electrons in a sample, and first focusing optics configured to direct a laser beam emitted by the first laser source towards the sample stage;
 a second laser source, configured to ablate sample material pre-seeded with electrons by the first laser source, and second focusing optics configured to direct a laser beam emitted by the second laser source towards sample stage;
 a third laser source, configured to ionize plumes of sample material ablated from the sample, and third focusing optics configured to direct a laser beam emitted by the third laser source to the volume in which ablated sample material forms a plume;
 wherein the first laser source, the second laser source and the third laser source are derived from a single laser, further comprising at least one beam splitter, at least one two harmonics generators, and at least one two optical delay lines,
 wherein one of the harmonics generators is adapted to produce UV, VUV, EUV or XUV laser radiation (as discussed above for the first laser source) from the single laser as the first laser source, and another of the harmonics generators is adapted to produce IR or visible wavelength laser radiation (as discussed above for the second laser source) from the single laser as the second laser source and the third laser source,
 wherein the second focusing optics comprises an optical delay line configured to synchronise a second pulse of laser radiation to arrive at a location on the sample stage such that the end of the second pulse is shorter than 50 ps following the start of the first pulse, such as shorter than 25 ps, shorter than 10 ps, shorter than 5 ps, shorter than 2 ps, or shorter than 1 ps; and
 wherein the third focusing optics comprises another optical delay line configured to synchronise a third pulse of laser radiation to arrive at a volume above the location on the sample stage shorter than 100 ps after the end of the pulse from the second laser source, such as shorter than 50 ps, shorter than 30 ps or shorter than 10 ps.

Equipment known in the art can be used to introduce delay between laser pulses. Accordingly, in some embodiments, the apparatus comprises an optical delay line to introduce delay between laser pulses. Examples of optical delay line suitable for use in the present invention are any of the optical delay lines commercially available from Thor-Labs.

Sample Chamber

The sample chamber of the two-pulse based sampling system may have features in common with the sample chamber of the laser ablation-based sampling system discussed above. It comprises a stage to support the sample. The stage may be a translation stage, movable in the x-y or x-y-z axes. The sample chamber will also comprise an outlet, through which material removed from the sample by the laser radiation can be directed. The outlet is connected to the detector, enabling analysis of the sample ions.

In some instances, the sample chamber is held under 133322-13.3 Pa, such as 1333.22-133.322 Pa. In some instances, the sample chamber is held under a vacuum. Accordingly, in some instances, the sample chamber pressure is lower than 50000 Pa, lower than 10000 Pa, lower than 5000 Pa, lower than 1000 Pa, lower than 500 Pa, lower than 100 Pa, lower than 10 Pa, lower than 1 Pa, around 0.1 Pa or less than 0.1 Pa, such as 0.01 Pa or lower. For instance, partial vacuum pressure may be around 200-700 Pa, and vacuum pressure 0.2 Pa or lower. Typical gases such as Argon, Helium, Nitrogen and mixtures thereof.

The selection of whether the sample pressure is at atmospheric pressure under a (partial) vacuum depends on the particular analysis being performed, as will be understood by one of skill in the art. For instance, at atmospheric pressure, sample handing is easier, and softer ionisation may be applied. Further, the presence of gas molecules may be desired so as to enable the phenomenon of collisional cooling to occur, which can be of interest when the label is a large molecule, the fragmentation of which is not desired, e.g. a molecular fragment comprising a labelling atom or combination thereof. Alternatively, in instances where laser radiation is used to post-ionise material the presence of gas molecules and collisional cooling may be advantageous to allow the cooling of the nanoplasma generated at the surface of the sample (i.e. following charged particle bombardment and laser illumination of the sample to generate the energy pumping state) and expansion of the plume of ablated material and before re-ionization in a post-ionization system.

The selection of whether the sample pressure is at atmospheric pressure under a (partial) vacuum depends on the particular analysis being performed, as will be understood by one of skill in the art. For instance, at atmospheric pressure, sample handing is easier, and softer ionisation may be applied. Further, the presence of gas molecules may be desired so as to enable the phenomenon of collisional cooling to occur, which can be of interest when the label is a large molecule, the fragmentation of which is not desired, e.g. a molecular fragment comprising a labelling atom or combination thereof.

Holding the sample chamber under vacuum can prevent collisions between sample ions generated and other particles within the chamber.

Ion Microscope and Optics

The sample ions are captured from the sample via an electrostatic lens positioned near to the sample, known in the art as an immersion lens (or an extraction lens). The immersion lens removes the secondary ions immediately from the locality of the sample. This is typically achieved by the sample and the lens having a large difference in voltage potential. Depending on the polarity of the sample vis-à-vis the immersion lens, positive or negative secondary ions are captured by the immersion lens. The polarity of the sample ions as captured by the immersion lens is independent of the polarity of the ions of the charged particle beam.

The sample ions are then transferred to the detector by via one or more further electrostatic lenses (known as transfer lenses in the art). The transfer lens(es) focus(es) the beam of secondary ions into the detector. Typically, in systems with multiple transfer lenses, only one transfer lens is engaged in a given analysis. Each lens may provide a different magnification of the sample surface. Commonly, further ion manipulation components are present between the immersion lens and the detector, for example one or more apertures, mass filters or sets of deflector plates. Together, the immersion lens, transfer lens, and any further components, form the ion microscope. Components for the production of an ion microscope are available from commercial suppliers e.g. Agilent.

Camera

The system may also comprise a camera. Camera systems are discussed above in relation to laser ablation sampling systems, and the features of the above camera can also be present in the secondary ion generation system, except where incompatible (e.g. it can be connected to a light microscope, such as a confocal microscope, but it is not possible to focus a primary ion beam through the same optics as the light which is directed to the camera, because one beam is ions and the other photons).

Methods of Using a Two-Pulse Laser Based Apparatus

The invention also provides methods of analysing a biological sample using an apparatus or sampling and ionisation system as described in this section. Accordingly, the features discussed above with respect to the apparatus are suitable features for incorporation in the method claims. Accordingly, the invention provides a method for analysing a sample comprising the steps of:
  (i) seeding electrons in a location on a sample using laser radiation emitted by a first laser source; and
  (ii) ablating sample material, from the location on the sample pre-seeded with electrons by the first laser source, using laser radiation emitted by a second laser source.

Step (ii) may also ionize (e.g., sustainably ionize) the seeded sample. In some embodiments, step (ii) is completed within shorter than 50 ps following the start of the first pulse, such as shorter than 25 ps, shorter than 10 ps, such as shorter than 5 ps, shorter than 2 ps, or shorter than 1 ps. of the commencement of step (i). In some embodiments, step (i) is performed with a pulse of laser radiation of 5 ps or shorter, such as 2 ps or shorter, 1 ps or shorter, 500 fs or shorter, 400 fs or shorter, 300 fs or shorter, 200 fs or shorter or 100 fs or shorter, 50 fs or shorter, 40 fs or shorter, 30 fs or shorter, 20 fs or shorter or 10 fs or shorter. In some embodiments, the laser radiation emitted by the first lase-r source is 200 nm or shorter, 175 nm or shorter, 150 nm or shorter, 125 nm or shorter, 100 nm or shorter, 75 nm or shorter, 50 nm or shorter, 25 nm or shorter, 20 nm or shorter or 15 nm. In some embodiments, the laser radiation emitted by the first laser source is between 10-200 nm, between 10-175 nm, between 10-150 nm, between 10-125 nm, between 10-100 nm, between 10-75 nm, between 10-50 nm, between 10-25 nm, between 10-20 nm, or between 10-15 nm. In some embodiments, the pulse energy of the first laser source is in the picoJ to femtoJ range, such as between 1 picoJ-999 femtoJ, between 10 picoJ-100 femtoJ, or between 100 picoJ-1 femtoJ. In some embodiments, the diameter of the location is 100 nm or shorter, such as 75 nm or shorter, 50 nm or shorter or around 30 nm.

In some embodiments, step (ii) is performed with a pulse of laser radiation of 5 ps or shorter, such as 2 ps or shorter, 1 ps or shorter, 500 fs or shorter, 400 fs or shorter, 300 fs or shorter, 200 fs or shorter or 100 fs or shorter, 50 fs or shorter, 40 fs or shorter, 30 fs or shorter, 20 fs or shorter or 10 fs or shorter. In some embodiments, the wavelength of laser radiation emitted by the second laser source is between 400 nm-100 µm, such as between 400 nm-10 µm, between 400 nm-1 µm, between 400 nm-900 nm, between 400 nm-800 nm, between 400 nm-700 nm, between 400 nm-600 nm or between 500 nm-600 nm, between 200 nm-100 µm, between 200 nm-10 µm, or between 200 nm-1 µm. In some embodiments, the pulse energy of the second laser source is in the nanoJoule range, such as between 1 nanoJ-1 µJ, between 10 nanoJ-500 nanoJ, between 50 nanoJ-250 nanoJ, or around 100 nanoJ.

In some embodiments, the method further comprises illuminating the plume of material ablated from the sample in step (ii) with laser radiation from a third laser source. In some embodiments, the laser radiation from the third laser source arrives at a volume above the location on the sample shorter than 10 ns after the end of the pulse from the second laser source, such as shorter than 1 ns, shorter than 100 ps, shorter than 50 ps, shorter than 30 ps or shorter than 10 ps Post-Ionisation Systems and Methods In any of the method of sampling described herein, including by initial radiation from a first energy source (e.g., a laser, ion beam, or electron beam), material released from the sample may be ionized by a laser at or near the sample surface. The laser used for ionisation may be an IR or visible laser, and may be on the picosecond scale (e.g., 1-1000 ps, 5-100 ps, 10-50 ps). The material released may be ionized by the laser within 100 ps to 10 ns of the initial radiation, allowing the material to expand past the critical density (before which neutralization would significantly reduce long-term ion formation). This may create a microplasma (above the surface), as oppose to a nanoplasma that would be formed from direct ionization at the sample surface. The sample (e.g., chamber housing the sample) may be held at vacuum or partial vacuum pressure to allow expansion of the ablation plume past the critical density and/or improve the ability of ion optics to direct resulting ions. Partial vacuum pressure (e.g., 10-10,000 Pa or 100-1,000 Pa) may allow for collisional cooling and/or charge reduction, and may improve the ion optics.

2. Mass Detector System

Exemplary types of mass detector system include quadrupole, time of flight (TOF), magnetic sector, high resolution, single or multicollector based mass spectrometers. A magnetic sector instrument is particularly suited for a high rate of recording of 1 megapixel per second and above.

The time taken to analyse the ionised material will depend on the type of mass analyser which is used for detection of ions. For example, instruments which use Faraday cups are generally too slow for analysing rapid signals. Overall, the desired imaging speed, resolution and degree of multiplexing will dictate the type(s) of mass analyser which should be used (or, conversely, the choice of mass analyser will determine the speed, resolution and multiplexing which can be achieved).

Mass spectrometry instruments that detect ions at only one mass-to-charge ratio (m/Q, commonly referred to as m/z in MS) at a time, for example using a point ion detector, will give poor results in imaging detecting. Firstly, the time taken to switch between mass-to-charge ratios limits the speed at which multiple signals can be determined, and secondly, if ions are at low abundance then signals can be missed when the instrument is focused on other mass-to-charge ratios. Thus it is preferred to use a technique which offers substantially simultaneous detection of ions having different m/Q values.

Detector Types

Quadrupole Detector

Quadrupole mass analysers comprise four parallel rods with a detector at one end. An alternating RF potential and fixed DC offset potential is applied between one pair of rods and the other so that one pair of rods (each of the rods opposite each other) has an opposite alternative potential to the other pair of rods. The ionised sample is passed through the middle of the rods, in a direction parallel to the rods and towards the detector. The applied potentials affect the trajectory of the ions such that only ions of a certain mass-charge ratio will have a stable trajectory and so reach the detector. Ions of other mass-charge ratios will collide with the rods.

Magnetic Sector Detector

In magnetic sector mass spectrometry, the ionised sample is passed through a curved flight tube towards an ion detector. A magnetic field applied across the flight tube causes the ions to deflect from their path. The amount of deflection of each ion is based on the mass to charge ratio of each ion and so only some of the ions will collide with the detector—the other ions will be deflected away from the detector. In multicollector sector field instruments, an array of detectors is be used to detect ions of different masses. In some instruments, such as the ThermoScientific Neptune Plus, and Nu Plasma II, the magnetic sector is combined with an electrostatic sector to provide a double-focussing magnetic sector instrument that analyses ions by kinetic energy, in addition to mass to charge ratio. In particular those multidetectors having a Mattauch-Herzog geometry can be used (e.g. the SPECTRO MS, which can simultaneously record all elements from lithium to uranium in a single measurement using a semiconductor direct charge detector). These instruments can measure multiple m/Q signals substantially simultaneously. Their sensitivity can be increased by including electron multipliers in the detectors. Array sector instruments are always applicable, however, because, although they are useful for detecting increasing signals, they are less useful when signal levels are decreasing, and so they are not well suited in situations where labels are present at particularly highly variable concentrations.

Time of Flight (TOF) Detector

A time of flight mass spectrometer comprises a sample inlet, an acceleration chamber with a strong electric field applied across it, and an ion detector. A packet of ionised sample molecules is introduced through the sample inlet and into the acceleration chamber. Initially, each of the ionised sample molecules has the same kinetic energy but as the ionised sample molecules are accelerated through the acceleration chamber, they are separated by their masses, with the lighter ionised sample molecules travelling faster than heaver ions. The detector then detects all the ions as they arrive. The time taking for each particle to reach the detector depends on the mass to charge ratio of the particle.

Thus a TOF detector can quasi-simultaneously register multiple masses in a single sample. In theory TOF techniques are not ideally suited to ICP ion sources because of their space charge characteristics, but TOF instruments can in fact analyse an ICP ion aerosol rapidly enough and sensitively enough to permit feasible single-cell imaging. Whereas TOF mass analyzers are normally unpopular for atomic analysis because of the compromises required to deal with the effects of space charge in the TOF accelerator and flight tube, tissue imaging according to the subject disclosure can be effective by detecting only the labelling atoms, and so other atoms (e.g. those having an atomic mass below 100) can be removed. This results in a less dense ion beam, enriched in the masses in (for example) the 100-250 dalton region, which can be manipulated and focused more efficiently, thereby facilitating TOF detection and taking advantage of the high spectral scan rate of TOF. Thus rapid imaging can be achieved by combining TOF detection with choosing labelling atoms that are uncommon in the sample and ideally having masses above the masses seen in an unlabelled sample e.g. by using the higher mass transition elements. Using a narrower window of label masses thus means that TOF detection to be used for efficient imaging.

Suitable TOF instruments are available from Tofwerk, GBC Scientific Equipment (e.g. the Optimass 9500 ICP-TOFMS), and Fluidigm Canada (e.g. the CyTOF™ and CyTOF™2 pinstruments). These CyTOF™ instruments have greater sensitivity than the Tofwerk and GBC instruments and are known for use in mass cytometry because they can rapidly and sensitively detect ions in the mass range of rare earth metals (particularly in the m/Q range of 100-200; see Bandura et al. (2009; *Anal. Chem.*, 81:6813-22)). Thus these are preferred instruments for use with the disclosure, and they can be used for imaging with the instrument settings already known in the art e.g. Bendal et al. (2011; *Science* 332, 687-696) & Bodenmiller et al. (2012; *Nat. Biotechnol.* 30:858-867). Their mass analysers can detect a large number of markers quasi-simultaneously at a high mass-spectrum acquisition frequency on the timescale of high-frequency laser ablation or sample desorption. They can measure the abundance of labelling atoms with a detection limit of about 100 per cell, permitting sensitive construction of an image of the tissue sample. Because of these features, mass cytometry can now be used to meet the sensitivity and multiplexing needs for tissue imaging at subcellular resolution. By combining the mass cytometry instrument with a high-resolution laser ablation sampling system and a rapid-transit low-dispersion sample chamber it has been possible to permit construction of an image of the tissue sample with high multiplexing on a practical timescale.

The TOF may be coupled with a mass-assignment corrector. The vast majority of ionisation events generate $M^+$ ions, where a single electron has been knocked out of the atom. Because of the mode of operation of the TOF MS there is sometimes some bleeding (or cross-talk) of the ions of one mass (M) into the channels for neighbouring masses (M±1), in particular where a large number of ions of mass M are entering the detector (i.e. ion counts which are high, but not so high that an ion deflector positioned between the sampling ionisation system and MS would prevent them from entering the MS, if the apparatus were to comprise such an ion deflector). As the arrival time of each $M^+$ ion at the detector follows a probability distribution about a mean (which is known for each M), when the number of ions at mass $M^+$ is high, then some will arrive at times that would normally be associated with the $M-1^+$ or $M+1^+$ ions. However, as each ion has a known distribution curve upon entering the TOF MS, based on the peak in the mass M channel it is possible to determine, the overlap of ions of mass M into the M±1 channels (by comparison to the known peak shape). The calculation is particularly applicable for TOF MS, because the peak of ions detected in a TOF MS is asymmetrical. Accordingly it is therefore possible to correct the readings for the M-1, M and M+1 channels to appropriately assign all of the detected ions to the M channel. Such corrections have particular use in correcting imaging data due to the nature of the large packets of ions produced by sampling and ionisation systems such as those disclosed herein involving laser ablation (or desorption as discussed below) as the techniques for removing material from the sample. Programs and methods for improving the quality of data by de-convoluting the data from TOF MS are discussed in WO2011/098834, U.S. Pat. No. 8,723,108 and WO2014/091243.

Dead-Time Corrector

As noted above, signals in the MS are detected on the basis of collisions between ions and the detector, and the release of electrons from the surface of the detector hit by the ions. When a high count of ions is detected by the MS resulting in the release of a large number of electrons, the detector of the MS can become temporarily fatigued, with the result that the analog signal output from the detector is temporarily depressed for one or more of the subsequent packets of ions. In other words, a particularly high count of ions in a packet of ionised sample material causes a lot of electrons to be released from the detector surface and secondary multiplier in the process of detecting the ions from that packet of ionised sample material, meaning that fewer electrons are available to be released when the ions in subsequent packets of ionised sample material hit the detector, until the electrons in the detector surface and secondary amplifier are replenished.

Based on a characterisation of the behaviour of the detector, it is possible to compensate for this dead-time phenomenon. A first step is to analyse the ion peak in the analog signal resulting from the detection of the nth packet of ionised sample material by the detector. The magnitude of the peak may be determined by the height of the peak, by the area of the peak, or by a combination of peak height and peak area.

The magnitude of the peak is then compared to see if it exceeds a predetermined threshold. If the magnitude is below this threshold, then no correction is necessary. If the magnitude is above the threshold, then correction of the digital signal from at least one subsequent packet of ionised sample material will be performed (at least the (n+1)th packet of ionised sample material, but possibly further packets of ionised sample material, such as (n+2)th, (n+3)th, (n+4)th etc.) to compensate for the temporary depression of the analog signal from these packets of ionised sample material resulting from the fatiguing of the detector caused by the nth packet of ionised sample material. The greater the magnitude of the peak of the nth packet of ionised sample material, the more peaks from subsequent packets of ionised sample material will need to be corrected and the magnitude of correction will need to be greater. Methods for correcting such phenomena are discussed in Stephan et al. (1994; Vac. Sci. Technol. 12:405), Tyler and Peterson (2013; Surf Interface Anal. 45:475-478), Tyler (2014; Surf Interface Anal. 46:581-590), WO2006/090138 and U.S. Pat. No. 6,229,142, and these methods can be applied by the dead-time corrector to the data, as described herein.

Analyser Apparatus Based on Optical Emission Spectra Detection

1. Sampling and Ionisation Systems a. Laser Ablation Based Sampling and Ionising System The laser ablation sampling system comprising a laser scanning system described above in relation to mass-based analysers can be employed in an OES detector-based system. For detection of atomic emission spectra, most preferably, an ICP is used to ionise the sample material removed from the sample, but any hard ionisation technique that can produce elemental ions can be used.

As appreciated by one of skill in the art, certain optional further components of the laser ablation based sampling and ionising system above, described in relation to avoiding overload of the mass-based detector, may not be applicable to all OES detector-based systems, and would not be incorporated, if inappropriate, by the skilled artisan.

2. Photodetectors Exemplary types of photodetectors include photomultipliers and charged-coupled devices (CCDs). Photodetetors may be used to image the sample and/or identify a feature/region of interest prior to imaging by elemental mass spectrometry.

Photomultipliers comprise a vacuum chamber comprising a photocathode, several dynodes, and an anode. A photon incident on the photocathode causes the photocathode to emit an electron as a consequence of the photoelectric effect. The electron is multiplied by the dynodes due to the process of secondary emission to produce a multiplied electron current, and then the multiplied electron current is detected by the anode to provide a measure of detection of electromagnetic radiation incident on the photocathode. Photomultipliers are available from, for example, ThorLabs.

A CCD comprises a silicon chip containing an array of light-sensitive pixels. During exposure to light, each pixel generates an electric charge in proportion to the intensity of light incident on the pixel. After the exposure, a control circuit causes a sequence of transfers of electric charge to produce a sequence of voltages. These voltages can then be analysed to produce an image. Suitable CCDs are available from, for example, Cell Biosciences.

Constructing an Image

The apparatus above can provide signals for multiple atoms in packets of ionised sample material removed from the sample. Detection of an atom in a packet of sample material reveals its presence at the position of ablation, be that because the atom is naturally present in the sample or because the atom has been localised to that location by a labelling reagent. By generating a series of packets of ionised sample material from known spatial locations on the sample's surface the detector signals reveal the location of the atoms on the sample, and so the signals can be used to construct an image of the sample. By labelling multiple targets with distinguishable labels it is possible to associate the location of labelling atoms with the location of cognate targets, so the method can build complex images, reaching levels of multiplexing which far exceed those achievable using traditional techniques such as fluorescence microscopy.

Assembly of signals into an image will use a computer and can be achieved using known techniques and software packages. For instance, the GRAPHIS package from Kylebank Software may be used, or other packages such as TERAPLOT can also be used. Imaging using MS data from techniques such as MALDI-MSI is known in the art e.g. Robichaud et al. (2013; *J Am Soc Mass Spectrom* 24 5:718-21) discloses the 'MSiReader' interface to view and analyze MS imaging files on a Matlab platform, and Klinkert et al. (2014; Int J Mass Spectrom http://dx.doi.org/10.1016/j.ijms.2013.12.012) discloses two software instruments for rapid data exploration and visualization of both 2D and 3D MSI data sets in full spatial and spectral resolution e.g. the 'Datacube Explorer' program. In addition, systems and methods described herein may be run according to software. For example, Images obtained using the methods disclosed herein can be further analysed e.g. in the same way that IHC results are analysed. For instance, the images can be used for delineating cell sub-populations within a sample, and can provide information useful for clinical diagnosis. Similarly, SPADE analysis can be used to extract a cellular hierarchy from the high-dimensional cytometry data which methods of the disclosure provide (Qiu et al. (2011; Nat. Biotechnol. 29:886-91)).

Samples

Certain aspects of the disclosure provide a method of imaging a biological sample. Such samples can comprise a plurality of cells which can be subjected to imaging mass cytometry (IMC) in order to provide an image of these cells in the sample. In general, the invention can be used to analyse tissue samples which are now studied by immunohistochemistry (IHC) techniques, but with the use of labelling atoms which are suitable for detection by mass spectrometry (MS) or optical emission spectrometry (OES). Furthermore, the present invention provides various techniques for preparing tissue samples in order to provide improved resolution over IMC and IMS techniques using samples prepared in a traditional manner. In particular, the present invention provides techniques for preparing samples which are suitable for imaging by electron microscopy, for preparing ultrathin samples, and a combination thereof. These methods are described further herein.

Any suitable tissue sample can be used in the methods described herein. For example, the tissue can include tissue from one or more of epithelium, muscle, nerve, skin, intestine, pancreas, kidney, brain, liver, blood (e.g. a blood smear), bone marrow, buccal swipes, cervical swipes, or any other tissue. The biological sample may be an immortalized cell line or primary cells obtained from a living subject. For diagnostic, prognostic or experimental (e.g., drug development) purposes the tissue can be from a tumor. In some embodiments, a sample may be from a known tissue, but it might be unknown whether the sample contains tumor cells. Imaging can reveal the presence of targets which indicate the presence of a tumor, thus facilitating diagnosis. Tissue from a tumor may comprise immune cells that are also characterized by the subject methods, and may provide insight into the tumor biology. The tissue sample may comprise formalin-fixed, paraffin-embedded (FFPE) tissue. The tissues can be obtained from any living multicellular organism, such as a mammal, an animal research model (e.g., of a particular disease, such as an immunodeficient rodent with a human tumor xenograft), or a human patient.

The tissue sample may be a section e.g. having a thickness within the range of 2-10 µm, such as between 4-6 µm. Techniques for preparing such sections are well known from the field of IHC e.g. using microtomes, including dehydration steps, fixation, embedding, permeabilization, sectioning etc. Thus, a tissue may be chemically fixed and then sections can be prepared in the desired plane. Cryosectioning or laser capture microdissection can also be used for preparing tissue samples. Samples may be permeabilised e.g. to permit uptake of reagents for labelling of intracellular targets (see above).

The size of a tissue sample to be analysed will be similar to current IHC methods, although the maximum size will be dictated by the laser ablation apparatus, and in particular by the size of sample which can fit into its sample chamber. A size of up to 5 mm×5 mm is typical, but smaller samples (e.g. 1 mm×1 mm) are also useful (these dimensions refer to the size of the section, not its thickness).

In addition to being useful for imaging tissue samples, the disclosure can instead be used for imaging of cellular samples such as monolayers of adherent cells or of cells which are immobilised on a solid surface (as in conventional immunocytochemistry). These embodiments are particularly useful for the analysis of adherent cells that cannot be easily solubilized for cell-suspension mass cytometry. Thus, as well as being useful for enhancing current immunohistochemical analysis, the disclosure can be used to enhance immunocytochemistry.

Ultrathin Samples

As discussed above, traditional IMC and IMS techniques use tissue samples that are several micrometres thick. However, some of the embodiments of the invention described herein, for example the apparatus for analysing a biological sample comprising an immersion medium positioned between the objective lens and the sample stage (see page 9 above), are not suitable for use with samples of such a thickness because the ablation region is typically of the order of 100 nm in all three dimensions, or at least in the lateral dimensions.

Therefore, the present invention provides a method of preparing a biological sample for analysis comprising labelling the sample with labelling atoms (labelling atoms are described further herein) and sectioning the sample into thin sections, optionally wherein the sample is sectioned into sections of thickness of less than 10 micrometers or below, such as 1 micrometer or below, or 100 nm or below, or 50 nm or below, or 30 nm or below. The invention also provides a method of preparing a biological sample for analysis comprising sectioning the sample into thin sections and labelling the sample with labelling atoms (labelling atoms are described further herein), optionally wherein the sample is sectioned into sections of thickness of less than 10 micrometers or below, such as 1 micrometer or below, or 100 nm or below, or 50 nm or below, or 30 nm or below. An automated microtome, such as the ATUMtome available from RM Boeckeler, can be used to section the sample into sections of a thickness in accordance with the method of the present invention.

Samples prepared according to the method set out above can be used with any of the IMC and IMS techniques described herein. However, samples prepared according to the method set out above are particularly suited to analysis by any of the apparatus comprising an immersion medium positioned between the objective lens and the sample stage described herein.

Furthermore, samples prepared according to the method set out above are also suited to analysis by any one of the sputtering based sampling and ionising systems set out above.

Sample Carrier

In certain embodiments, the sample may be immobilized on a solid support (i.e. a sample carrier), to position it for imaging mass spectrometry. The solid support may be optically transparent, for example made of glass or plastic. Where the sample carrier is optically transparent, it enables ablation of the sample material through the carrier, as illustrated in FIGS. 3-5 and 8-10. Ablation through the material of the sample carrier has particular advantages when laser radiation is directed onto the sample through an immersion medium.

Sometimes, the sample carrier will comprise features that act as reference points for use with the apparatus and methods described herein, for instance to allow the calculation of the relative position of features/regions of interest that are to be ablated or desorbed and analysed. The reference points may be optically resolvable, or may be resolvable by mass analysis.

Target Elements

In imaging mass spectrometry, the distribution of one or more target elements (i.e., elements or elemental isotopes) may be of interest. In certain aspects, target elements are labelling atoms as described herein. A labelling atom may be directly added to the sample alone or covalently bound to or within a biologically active molecule. In certain embodiments, labelling atoms (e.g., metal tags) may be conjugated to a member of a specific binding pair (SBP), such as an antibody (that binds to its cognate antigen), aptamer or oligonucleotide for hybridizing to a DNA or RNA target, as described in more detail below. Labelling atoms may be attached to an SBP by any method known in the art. In certain aspects, the labelling atoms are a metal element, such as a lanthanide or transition element or another metal tag as described herein. The metal element may have a mass greater than 60 amu, greater than 80 amu, greater than 100 amu, or greater than 120 amu. Mass spectrometers described herein may deplete elemental ions below the masses of the metal elements, so that abundant lighter elements do not create space-charge effects and/or overwhelm the mass detector.

Labelling of the Tissue Sample

The disclosure produces images of samples which have been labelled with labelling atoms, for example a plurality of different labelling atoms, wherein the labelling atoms are detected by an apparatus capable of sampling specific, preferably subcellular, areas of a sample (the labelling atoms therefore represent an elemental tag). The reference to a plurality of different atoms means that more than one atomic species is used to label the sample. These atomic species can be distinguished using a mass detector (e.g. they have different m/Q ratios), such that the presence of two different labelling atoms within a plume gives rise to two different MS signals. The atomic species can also be distinguished using an optical spectrometer (e.g. different atoms have different emission spectra), such that the presence of two different labelling atoms within a plume gives rise to two different emission spectral signals.

Labelling for Electron Microscopy (EM) Techniques

Immunoelectron microscopy is the use of electron microscopy to study the ultrastructure of tissues or cells. In immunoelectron microscopy, electron microscopy is used to detect the antibody SPBs labelled with heavy metal particles, such as those described further herein. Scanning electron microscopy (SEM) and transmission electron microscopy (TEM) are both well known electron microscopy techniques and can be used to detect the antibody SPBs. Scanning electron microscopy (SEM) is used to detect signals resulting from the interaction of electrons with the surface of the sample. Transmission electron microscopy (TEM) is used to detect images produced by electrons passing through ultrathin specimens (less than 50 nm). Standard protocol for preparing samples for immunoelectron microscopy involves tissue fixation, inclusion in an appropriate embedding resin and subsequent ultrathin sectioning (to sections of thickness of 50 nm or less) and incubation with specific antibodies for the molecules whose ultrastructural location needs to be determined.

The present invention utilises techniques for preparing samples that are suitable for analysis by electron microscopy. In one aspect, the present invention provides a method for preparing a biological sample for analysis comprising staining the sample with a contrast agent for electron microscopy (EM); and labelling the sample with labelling atoms. In some embodiments, the method comprises prior to staining or labelling, the step of preparing an ultrathin section of the biological sample, such as 100 nm or thinner, 50 nm or thinner or 30 nm or thinner. In this way, the present invention provides samples which are suitable for imaging using EM prior to analysis using any of the IMC and IMS techniques discussed herein. Thus, the present invention provides opportunities to provide imaging of a higher resolution and/or multiplexity than traditional IMC and IMS techniques.

In some embodiments of the invention, the contrast agent for EM is visible in an imaging mass cytometer or imaging mass spectrometer. Accordingly, the present invention provides a method of preparing a biological sample in which the contrast agent includes at least one of osmium tetroxide, gold, silver and iridium. Thus, the biological sample prepared according to the method of the present invention can be read first by EM, thereby providing spatial resolution on a 3 nm scale for one (affinity) channel (the EM contrast agent), and then read by IMC/IMS with a spatial resolution of 100 nm with as many affinity channels as provided by the labelling atoms (for example, over 40 affinity channels). One advantage of utilising contrast agents for EM which are also visible in a mass cytometer, such as osmium tetroxide or iridium, is that the IMC/IMS can easily read out the contrast agents and so the images obtained by EM and IMC/IMS can be overlaid and co-registered. The EM provides fine detail and IMC/IMS provides the advantage of monitoring biological states of the specimen on many affinity channels. In this way, preparing a biological sample for analysis according to the present invention provides an opportunity to expand IMC capabilities to ultrastructural analysis of cells, obtaining higher resolution images than those provided by traditional IMC and IMS.

Furthermore, preparing a biological sample in a style suitable for electron microscopy generally includes preparing the samples in a resin, as opposed to formalin fixed paraffin-embedded (FFPE; which is discussed above). FFPE based samples can shift and smear when drying, reducing image resolution. On the other hand, resin in the specimen facilitates uniformity of ablation further increases the resolution.

Moreover, preparing a biological in a style suitable for electron microscopy generally includes sectioning the sample into thin samples, as described for example on page 40. Accordingly, the present invention provides a method of preparing a biological sample for analysis comprising: first comprising sectioning the sample into thin sections; optionally wherein the sample is sectioned into sections of thickness of less than 10 micrometers or below, such as 1 micrometer or below, or 100 nm or below, or 30 nm or below.

In some embodiments of the invention, the labelling atoms include at least one of gold and lanthanide labelled antibodies.

Samples prepared according to the method set out above can be used with any of the IMC and IMS techniques described herein. Accordingly, the present invention provides a method of analysing a biological sample comprising:
 directing a beam of radiation emitted by the laser source towards a location on the sample to produce an ablated plume of sample material;
 ionising the ablated plume of sample material; and
 detecting the sample ions from the sample material;
 optionally, wherein the method of the present invention comprises first performing electron microscopy. In some embodiments, the ions are detected by a TOF MS. In some embodiments, the sample material is ionised by ICP.

In order to reconstruct the image of a single layer of the thickness of a biological cell or to read a thicker specimen layer by layer and generate a 3D image, as discussed further herein, the sample preferably has a thickness of 100 micrometers or below, such as 10 micrometers or below, or 100 nm or below, or 50 nm or below, or 30 nm or below. In some embodiments described in more detail herein, the immersion medium is referred to as an immersion lens. The invention also provides use of a biological sample with a thickness of 100 nm or less in a method of imaging mass cytometry. The invention also provides use of a biological sample labelled with lanthanide and/or actinide atoms in an electron microscopy method.

The present invention also provides a method of analysing a biological sample comprising performing electron microscopy (such as transmission electron microscopy) on the sample, and then performing IMC on the sample. In some embodiments, the invention provides a method of analysing a biological sample comprising the steps of:
 a) performing transmission electron microscopy on the sample to generate an EM image;
 b) sampling and ionising material from one or more locations on the sample, comprising the step of directing laser radiation at each location on the sample to generate a plume of sample material from each location,
 c) detecting ions in the plumes of sample material, whereby detection of the ions in the plumes permits construction of an element image of the sample.

This method sometimes further comprises the step of overlaying the EM image and the element image. In some embodiments, the locations are known locations.

In some embodiments, the invention provides a method of analysing a biological sample comprising the steps of:
 a) staining the biological sample with a contrast reagent for EM and labelling one or more a target molecules in the tissue sample with labelling atoms, to provide a stained and labelled sample;
 b) performing transmission electron microscopy on the stained and labelled sample to generate an EM image;
 c) sampling and ionising material from one or more known locations on the stained and labelled sample, comprising the step of directing laser radiation at each known location on the sample to generate a plume of sample material from each known location,
 d) detecting ions in the plumes of sample material, whereby detection of ions of the labelling atoms in the plumes permits construction of an element image of the sample.

This method sometimes further comprises the step of overlaying the EM image and the element image. In some embodiments, the laser radiation samples material and ionises it. In some embodiments, ionisation to generate ions for detection is performed separately from sampling by an ICP.

Mass Tagged Reagents

Mass-tagged reagents as used herein comprise a number of components. The first is the SBP. The second is the mass tag. The mass tag and the SBP are joined by a linker, formed at least in part of by the conjugation of the mass tag and the SBP. The linkage between the SBP and the mass tag may also comprise a spacer. The mass tag and the SBP can be conjugated together by a range of reaction chemistries. Exemplary conjugation reaction chemistries include thiol maleimide, NHS ester and amine, or click chemistry reactivities (preferably Cu(I)-free chemistries), such as strained alkyne and azide, strained alkyne and nitrone and strained alkene and tetrazine.

Mass Tags

The mass tag used in the present invention can take a number of forms. Typically, the tag comprises at least one labelling atom. A labelling atom is discussed herein below.

Accordingly, in its simplest form, the mass tag may comprise a metal-chelating moiety which is a metal-chelating group with a metal labelling atom co-ordinated in the ligand. In some instances, detecting only a single metal atom per mass tag may be sufficient. However, in other instances, it may be desirable of each mass tag to contain more than one labelling atom. This can be achieved in a number of ways, as discussed below.

A first means to generate a mass tag that can contain more than one labelling atom is the use of a polymer comprising metal-chelating ligands attached to more than one subunit of the polymer. The number of metal-chelating groups capable of binding at least one metal atom in the polymer can be between approximately 1 and 10,000, such as 5-100, 10-250, 250-5,000, 500-2,500, or 500-1,000. At least one metal atom can be bound to at least one of the metal-chelating groups. The polymer can have a degree of polymerization of between approximately 1 and 10,000, such as 5-100, 10-250, 250-5,000, 500-2,500, or 500-1,000. Accordingly, a polymer based mass tag can comprise between approximately 1 and 10,000, such as 5-100, 10-250, 250-5,000, 500-2,500, or 500-1,000 labelling atoms.

The polymer can be selected from the group consisting of linear polymers, copolymers, branched polymers, graft copolymers, block polymers, star polymers, and hyperbranched polymers. The backbone of the polymer can be derived from substituted polyacrylamide, polymethacrylate, or polymethacrylamide and can be a substituted derivative of a homopolymer or copolymer of acrylamides, methacrylamides, acrylate esters, methacrylate esters, acrylic acid or methacrylic acid. The polymer can be synthesised from the group consisting of reversible addition fragmentation polymerization (RAFT), atom transfer radical polymerization (ATRP) and anionic polymerization. The step of providing the polymer can comprise synthesis of the polymer from compounds selected from the group consisting of N-alkyl acrylamides, N,N-dialkyl acrylamides, N-aryl acrylamides, N-alkyl methacrylamides, N,N-dialkyl methacrylamides, Naryl methacrylamides, methacrylate esters, acrylate esters and functional equivalents thereof.

The polymer can be water soluble. This moiety is not limited by chemical content. However, it simplifies analysis if the skeleton has a relatively reproducible size (for example, length, number of tag atoms, reproducible dendrimer character, etc.). The requirements for stability, solubility, and non-toxicity are also taken into consideration. Thus, the preparation and characterization of a functional water soluble polymer by a synthetic strategy that places many functional groups along the backbone plus a different reactive group (the linking group), that can be used to attach the polymer to a molecule (for example, an SBP), through a linker and optionally a spacer. The size of the polymer is controllable by controlling the polymerisation reaction. Typically the size of the polymer will be chosen so as the radiation of gyration of the polymer is as small as possible, such as between 2 and 11 nanometres. The length of an IgG antibody, an exemplary SBP, is approximately 10 nanometres, and therefore an excessively large polymer tag in relation to the size of the SBP may sterically interfere with SBP binding to its target.

The metal-chelating group that is capable of binding at least one metal atom can comprise at least four acetic acid groups. For instance, the metal-chelating group can be a diethylenetriaminepentaacetate (DTPA) group or a 1,4,7,10-tetraazacyclododecane-1,4,7,10-tetraacetic acid (DOTA) group. Alternative groups include Ethylenediaminetetraacetic acid (EDTA) and ethylene glycol-bis(β-aminoethyl ether)-N,N,N',N'-tetraacetic acid (EGTA)

The metal-chelating group can be attached to the polymer through an ester or through an amide. Examples of suitable metal-chelating polymers include the X8 and DM3 polymers available from Fluidigm Canada, Inc.

The polymer can be water soluble. Because of their hydrolytic stability, N-alkyl acrylamides, N-alkyl methacrylamides, and methacrylate esters or functional equivalents can be used. A degree of polymerization (DP) of approximately 1 to 1000 (1 to 2000 backbone atoms) encompasses most of the polymers of interest. Larger polymers are in the scope of the invention with the same functionality and are possible as would be understood by practitioners skilled in the art. Typically the degree of polymerization will be between 1 and 10,000, such as 5-100, 10-250, 250-5,000, 500-2,500, or 500-1,000. The polymers may be amenable to synthesis by a route that leads to a relatively narrow polydispersity. The polymer may be synthesized by atom transfer radical polymerization (ATRP) or reversible addition-fragmentation (RAFT) polymerization, which should lead to values of Mw (weight average molecular weight)/Mn (number average molecular weight) in the range of 1.1 to 1.2. An alternative strategy involving anionic polymerization, where polymers with Mw/Mn of approximately 1.02 to 1.05 are obtainable. Both methods permit control over end groups, through a choice of initiating or terminating agents. This allows synthesizing polymers to which the linker can be attached. A strategy of preparing polymers containing functional pendant groups in the repeat unit to which the liganded transition metal unit (for example a Ln unit) can be attached in a later step can be adopted. This embodiment has several advantages. It avoids complications that might arise from carrying out polymerizations of ligand containing monomers.

To minimize charge repulsion between pendant groups, the target ligands for ($M^{3+}$) should confer a net charge of −1 on the chelate.

Polymers that be used in the invention include:
random copolymer poly(DMA-co-NAS): The synthesis of a 75/25 mole ratio random copolymer of N-acryloxysuccinimide (NAS) with N,N-dimethyl acrylamide (DMA) by RAFT with high conversion, excellent molar mass control in the range of 5000 to 130,000, and with Mw/Mn≈1.1 is reported in Relógio et al. (2004) (Polymer, 45, 8639-49). The active NHS ester is reacted with a metal-chelating group bearing a reactive amino group to yield the metal-chelating copolymer synthesised by RAFT polymerization.

poly(NMAS): NMAS can be polymerised by ATRP, obtaining polymers with a mean molar mass ranging from 12 to 40 KDa with Mw/Mn of approximately 1.1 (see e.g. Godwin et al., 2001; Angew. Chem.Int.Ed, 40: 594-97).

poly(MAA): polymethacrylic acid (PMAA) can be prepared by anionic polymerization of its t-butyl or trimethylsilyl (TMS) ester.

poly(DMAEMA): poly(dimethylaminoethyl methacrylate) (PDMAEMA) can be prepared by ATRP (see Wang et al, 2004, J.Am.Chem.Soc, 126, 7784-85). This is a well-known polymer that is conveniently prepared with mean Mn values ranging from 2 to 35 KDa with Mw/Mn of approximately 1.2 This polymer can also be synthesized by anionic polymerization with a narrower size distribution.

polyacrylamide, or polymethacrylamide.

The metal-chelating groups can be attached to the polymer by methods known to those skilled in the art, for example, the pendant group may be attached through an ester or through an amide. For instance, to a methylacrylate based polymer, the metal-chelating group can be attached to the polymer backbone first by reaction of the polymer with ethylenediamine in methanol, followed by subsequent reaction of DTPA anhydride under alkaline conditions in a carbonate buffer.

A second means is to generate nanoparticles which can act as mass tags. A first pathway to generating such mass tags is the use of nanoscale particles of the metal which have been coated in a polymer. Here, the metal is sequestered and shielded from the environment by the polymer, and does not react when the polymer shell can be made to react e.g. by functional groups incorporated into the polymer shell. The functional groups can be reacted with linker components (optionally incorporating a spacer) to attach click chemistry reagents, so allowing this type of mass tag to plug in to the synthetics strategies discussed above in a simple, modular fashion.

Grafting-to and grafting-from are the two principle mechanism for generating polymer brushes around a nanoparticle. In grafting to, the polymers are synthesised separately, and so synthesis is not constrained by the need to keep the nanoparticle colloidally stable. Here reversible addition-fragmentation chain transfer (RAFT) synthesis has excelled due to a large variety of monomers and easy functionalization. The chain transfer agent (CTA) can be readily used as functional group itself, a functionalized CTA can be used or the polymer chains can be post-functionalized. A chemical reaction or physisorption is used to attach the polymers to the nanoparticle. One drawback of grafting-to is the usually lower grafting density, due to the steric repulsion of the coiled polymer chains during attachment to the particle surface. All grafting-to methods suffer from the drawback that a rigorous workup is necessary to remove the excess of free ligand from the functionalized nanocomposite particle. This is typically achieved by selective precipitation and centrifugation. In the grafting-from approach molecules, like initiators for atomic transfer radical polymerization (ATRP) or CTAs for (RAFT) polymerizations, are immobilized on the particle surface. The drawbacks of this method are the development of new initiator coupling reactions. Moreover, contrary to grafting-to, the particles have to be colloidally stable under the polymerization conditions.

An additional means of generating a mass tag is via the use of doped beads. Chelated lanthanide (or other metal) ions can be employed in miniemulsion polymerization to create polymer particles with the chelated lanthanide ions embedded in the polymer. The chelating groups are chosen, as is known to those skilled in the art, in such a way that the metal chelate will have negligible solubility in water but reasonable solubility in the monomer for miniemulsion polymerization. Typical monomers that one can employ are styrene, methylstyrene, various acrylates and methacrylates, among others as is known to those skilled in the art. For mechanical robustness, the metal-tagged particles have a glass transition temperature (Tg) above room temperature. In some instances, core-shell particles are used, in which the metal-containing particles prepared by miniemulsion polymerization are used as seed particles for a seeded emulsion polymerization to control the nature of the surface functionality. Surface functionality can be introduced through the choice of appropriate monomers for this second-stage polymerization. Additionally, acrylate (and possible methacrylate) polymers are advantageous over polystyrene particles because the ester groups can bind to or stabilize the unsatisfied ligand sites on the lanthanide complexes. An exemplary method for making such doped beads is: (a) combining at least one labelling atom-containing complex in a solvent mixture comprising at least one organic monomer (such as styrene and/or methyl methacrylate in one embodiment) in which the at least one labelling atom-containing complex is soluble and at least one different solvent in which said organic monomer and said at least one labelling atom-containing complex are less soluble, (b) emulsifying the mixture of step (a) for a period of time sufficient to provide a uniform emulsion; (c) initiating polymerization and continuing reaction until a substantial portion of monomer is converted to polymer; and (d) incubating the product of step (c) for a period of time sufficient to obtain a latex suspension of polymeric particles with the at least one labelling atom-containing complex incorporated in or on the particles therein, wherein said at least one labelling atom-containing complex is selected such that upon interrogation of the polymeric mass tag, a distinct mass signal is obtained from said at least one labelling atom. By the use of two or more complexes comprising different labelling atoms, doped beads can be made comprising two or more different labelling atoms. Furthermore, controlling the ration of the complexes comprising different labelling atoms, allows the production of doped beads with different ratios of the labelling atoms. By use of multiple labelling atoms, and in different radios, the number of distinctively identifiable mass tags is increased. In core-shell beads, this may be achieved by incorporating a first labelling atom-containing complex into the core, and a second labelling atom-containing complex into the shell.

A yet further means is the generation of a polymer that include the labelling atom in the backbone of the polymer rather than as a co-ordinated metal ligand. For instance, Carerra and Seferos (Macromolecules 2015, 48, 297-308) disclose the inclusion of tellurium into the backbone of a polymer. Other polymers incorporating atoms capable as functioning as labelling atoms tin-, antimony- and bismuth-incorporating polymers. Such molecules are discussed inter alia in Priegert et al., 2016 (Chem. Soc. Rev., 45, 922-953).

Thus the mass tag can comprise at least two components: the labelling atoms, and a polymer, which either chelates, contains or is doped with the labelling atom. In addition, the mass tag comprises an attachment group (when not-conjugated to the SBP), which forms part of the chemical linkage between the mass tag and the SBP following reaction of the two components, in a click chemistry reaction in line with the discussion above.

A polydopamine coating can be used as a further way to attach SBPs to e.g. doped beads or nanoparticles. Given the range of functionalities in polydopamine, SBPs can be conjugated to the mass tag formed from a PDA coated bead or particle by reaction of e.g. amine or sulhydryl groups on the SBP, such as an antibody. Alternatively, the functionalities on the PDA can be reacted with reagents such as bifunctional linkers which introduce further functionalities in turn for reaction with the SBP. In some instances, the linkers can contain spacers, as discussed below. These spacers increase the distance between the mass tag and the SBP, minimising steric hindrance of the SBP. Thus the invention comprises a mass-tagged SBP, comprising an SBP and a mass tag comprising polydopamine, wherein the polydopamine comprises at least part of the link between the SBP and the mass tag. Nanoparticles and beads, in particular polydopamine coated nanoparticles and beads, may be useful for signal enhancement to detect low abundance targets, as they can have thousands of metal atoms and may have multiple copies of the same affinity reagent. The affinity reagent could be a secondary antibody, which could further boost signal.

Labelling Atom

Labelling atoms that can be used with the disclosure include any species that are detectable by MS or OES and that are substantially absent from the unlabelled tissue sample. Thus, for instance, $^{12}C$ atoms would be unsuitable as labelling atoms because they are naturally abundant, whereas $^{11}C$ could in theory be used for MS because it is an artificial isotope which does not occur naturally. Often the labelling atom is a metal. In preferred embodiments, however, the labelling atoms are transition metals, such as the rare earth metals (the 15 lanthanides, plus scandium and yttrium). These 17 elements (which can be distinguished by OES and MS) provide many different isotopes which can be easily distinguished (by MS). A wide variety of these elements are available in the form of enriched isotopes e.g. samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium, (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). In addition to rare earth metals, other metal atoms are suitable for detection e.g. gold (Au), platinum (Pt), iridium (Ir), rhodium (Rh), bismuth (Bi), etc. The use of radioactive isotopes is not preferred as they are less convenient to handle and are unstable e.g. Pm is not a preferred labelling atom among the lanthanides.

In order to facilitate time-of-flight (TOF) analysis (as discussed herein) it is helpful to use labelling atoms with an atomic mass within the range 80-250 e.g. within the range 80-210, or within the range 100-200. This range includes all of the lanthanides, but excludes Sc and Y. The range of 100-200 permits a theoretical 101-plex analysis by using different labelling atoms, while taking advantage of the high spectral scan rate of TOF MS. As mentioned above, by choosing labelling atoms whose masses lie in a window above those seen in an unlabelled sample (e.g. within the range of 100-200), TOF detection can be used to provide rapid imaging at biologically significant levels.

Various numbers of labelling atoms can be attached to a single SBP member dependent upon the mass tag used (and so the number of labelling atoms per mass tag) and the number of mass tags that are attached to each SBP). Greater sensitivity can be achieved when more labelling atoms are attached to any SBP member. For example, greater than 10, 20, 30, 40, 50, 60, 70, 80, 90 or 100 labelling atoms can be attached to a SBP member, such as up to 10,000, for instance as 5-100, 10-250, 250-5,000, 500-2,500, or 500-1,000 labelling atoms. As noted above, monodisperse polymers containing multiple monomer units may be used, each containing a chelator such as diethylenetriaminepentaacetic acid (DTPA) or DOTA. DTPA, for example, binds 3+ lanthanide ions with a dissociation constant of around $10^{31\ 6}$ M. These polymers can terminate in a thiol which can be used for attaching to a SBP via reaction of that with a maleimide to attach a click chemistry reactivity in line with those discussed above. Other functional groups can also be used for conjugation of these polymers e.g. amine-reactive groups such as N-hydroxy succinimide esters, or groups reactive against carboxyls or against an antibody's glycosylation. Any number of polymers may bind to each SBP. Specific examples of polymers that may be used include straight-chain ("X8") polymers or third-generation dendritic ("DN3") polymers, both available as MaxPar™ reagents. Use of metal nanoparticles can also be used to increase the number of atoms in a label, as also discussed above.

In some embodiments, all labelling atoms in a mass tag are of the same atomic mass. Alternatively, a mass tag can comprise labelling atoms of differing atomic mass. Accordingly, in some instances, a labelled sample may be labelled with a series of mass-tagged SBPs each of which comprises just a single type of labelling atom (wherein each SBP binds its cognate target and so each kind of mass tag is localised on the sample to a specific e.g. antigen). Alternatively, in some instance, a labelled sample may be labelled with a series of mass-tagged SBPs each of which comprises a mixture of labelling atoms. In some instances, the mass-tagged SBPs used to label the sample may comprise a mix of those with single labelling atom mass tags and mixes of labelling atoms in their mass tags.

Spacer

As noted above, in some instances, the SBP is conjugated to a mass tag through a linker which comprises a spacer. There may be a spacer between the SBP and the click chemistry reagent (e.g. between the SBP and the strained cycloalkyne (or azide); strained cycloalkene (or tetrazine); etc.). There may be a spacer between the between the mass tag and the click chemistry reagent (e.g. between the mass tag and the azide (or strained cycloalkyne); tetrazine (or strained cycloalkene); etc.). In some instances there may be a spacer both between the SNP and the click chemistry reagent, and the click chemistry reagent and the mass tag.

The spacer might be a polyethylene glycol (PEG) spacer, a poly(N-vinylpyrolide) (PVP) spacer, a polyglycerol (PG) spacer, poly(N-(2-hydroxylpropyl)methacrylamide) spacer, or a polyoxazoline (POZ, such as polymethyloxazoline, polyethyloxazoline or polypropyloxazoline) or a C5-C20 non-cyclic alkyl spacer. For example, the spacer may be a PEG spacer with 3 or more, 4 or more, 5 or more, 6 or more, 7 or more, 8 or more, 9 or more, 10 or more, 11 or more, 12 or more, 15 or more of 20 or more EG (ethylene glycol) units. The PEG linker may have from 3 to 12 EG units, from 4 to 10, or may have 4, 5, 6, 7, 8, 9, or 10 EG units. The linker may include cystamine or derivatives thereof, may include one or more disulfide groups, or may be any other suitable linker known to one of skill in the art.

Spacers may be beneficial to minimize the steric effect of the mass tag on the SBP to which is conjugated. Hydrophilic spacers, such as PEG based spacers, may also act to improve the solubility of the mass-tagged SBP and act to prevent aggregation.

SBPs

Mass cytometry, including imaging mass cytometry is based on the principle of specific binding between members of specific binding pairs. The mass tag is linked to a specific binding pair member, and this localises the mass tag to the target/analyte which is the other member of the pair. Specific binding does not require binding to just one molecular species to the exclusion of others, however. Rather it defines that the binding is not-nonspecific, i.e. not a random interaction. An example of an SBP that binds to multiple targets would therefore be an antibody which recognises an epitope that is common between a number of different proteins. Here, binding would be specific, and mediated by the CDRs of the antibody, but multiple different proteins would be detected by the antibody. The common epitopes may be naturally occurring, or the common epitope could be an artificial tag, such as a FLAG tag. Similarly, for nucleic acids, a nucleic acid of defined sequence may not bind exclusively to a fully complementary sequence, but varying tolerances of mismatch can be introduced under the use of hybridisation conditions of a differing stringencies, as would be appreciated by one of skill in the art. Nonetheless, this hybridisation is not non-specific, because it is mediated by homology between the SBP nucleic acid and the target analyte. Similarly, ligands can bind specifically to multiple receptors, a facile example being TNFa which binds to both TNFR1 and TNFR2.

The SBP may comprise any of the following: a nucleic acid duplex; an antibody/antigen complex; a receptor/ligand pair; or an aptamer/target pair. Thus a labelling atom can be attached to a nucleic acid probe which is then contacted with a tissue sample so that the probe can hybridise to complementary nucleic acid(s) therein e.g. to form a DNA/DNA duplex, a DNA/RNA duplex, or a RNA/RNA duplex. Similarly, a labelling atom can be attached to an antibody which is then contacted with a tissue sample so that it can bind to its antigen. A labelling atom can be attached to a ligand which is then contacted with a tissue sample so that it can bind to its receptor. A labelling atom can be attached to an aptamer ligand which is then contacted with a tissue sample so that it can bind to its target. Thus, labelled SBP members can be used to detect a variety of targets in a sample, including DNA sequences, RNA sequences, proteins, sugars, lipids, or metabolites.

The mass-tagged SBP therefore can be a protein or peptide, or a polynucleotide or oligonucleotide.

Examples of protein SBPs include an antibody or antigen binding fragment thereof, a monoclonal antibody, a polyclonal antibody, a bispecific antibody, a multispecific antibody, an antibody fusion protein, scFv, antibody mimetic, avidin, streptavidin, neutravidin, biotin, or a combination thereof, wherein optionally the antibody mimetic comprises a nanobody, affibody, affilin, affimer, affitin, alphabody, anticalin, avimer, DARPin, Fynomer, kunitz domain peptide, monobody, or any combination thereof, a receptor, such as a receptor-Fc fusion, a ligand, such as a ligand-Fc fusion, a lectin, for example an agglutinin such as wheat germ agglutinin.

The peptide may be a linear peptide, or a cyclical peptide, such as a bicyclic peptide. One example of a peptide that can be used is Phalloidin.

A polynucleotide or oligonucleotide generally refers to a single- or double-stranded polymer of nucleotides containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), yPNAs, morpholino polynucleotides, locked nucleic acids (LNAs), threose nucleic acid (TNA), 2'-0-Methyl polynucleotides, 2'-0-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding.

Antibody SBP Members

In a typical embodiment, the labelled SBP member is an antibody. Labelling of the antibody can be achieved through conjugation of one or more labelling atom binding molecules to the antibody, by attachment of a mass tag using e.g. NHS-amine chemistry, sulfhydryl-maleimide chemistry, or the click chemistry (such as strained alkyne and azide, strained alkyne and nitrone, strained alkene and tetrazine etc.). Antibodies which recognise cellular proteins that are useful for imaging are already widely available for IHC usage, and by using labelling atoms instead of current labelling techniques (e.g. fluorescence) these known antibodies can be readily adapted for use in methods disclosure herein, but with the benefit of increasing multiplexing capability. Antibodies can recognise targets on the cell surface or targets within a cell. Antibodies can recognise a variety of targets e.g. they can specifically recognise individual proteins, or can recognise multiple related proteins which share common epitopes, or can recognise specific post-translational modifications on proteins (e.g. to distinguish between tyrosine and phosphor-tyrosine on a protein of interest, to distinguish between lysine and acetyl-lysine, to detect ubiquitination, etc.). After binding to its target, labelling atom(s) conjugated to an antibody can be detected to reveal the location of that target in a sample.

The labelled SBP member will usually interact directly with a target SBP member in the sample. In some embodiments, however, it is possible for the labelled SBP member to interact with a target SBP member indirectly e.g. a primary antibody may bind to the target SBP member, and a labelled secondary antibody can then bind to the primary antibody, in the manner of a sandwich assay. Usually, however, the method relies on direct interactions, as this can be achieved more easily and permits higher multiplexing. In both cases, however, a sample is contacted with a SBP member which can bind to a target SBP member in the sample, and at a later stage label attached to the target SBP member is detected.

Nucleic Acid SBPs, and Labelling Methodology Modifications

RNA is another biological molecule which the methods and apparatus disclosed herein are capable of detecting in a specific, sensitive and if desired quantitative manner. In the same manner as described above for the analysis of proteins, RNAs can be detected by the use of a SBP member labelled with an elemental tag that specifically binds to the RNA (e.g. an poly nucleotide or oligonucleotide of complementary sequence as discussed above, including a locked nucleic acid (LNA) molecule of complementary sequence, a peptide nucleic acid (PNA) molecule of complementary sequence, a plasmid DNA of complementary sequence, an amplified DNA of complementary sequence, a fragment of RNA of complementary sequence and a fragment of genomic DNA of complementary sequence). RNAs include not only the mature mRNA, but also the RNA processing intermediates and nascent pre-mRNA transcripts.

In certain embodiments, both RNA and protein are detected using methods of the claimed invention.

To detect RNA, cells in biological samples as discussed herein may be prepared for analysis of RNA and protein content using the methods and apparatus described herein. In certain aspects, cells are fixed and permeabilized prior to the hybridization step. Cells may be provided as fixed and/or pemeabilized. Cells may be fixed by a crosslinking fixative, such as formaldehyde, glutaraldehyde. Alternatively or in addition, cells may be fixed using a precipitating fixative, such as ethanol, methanol or acetone. Cells may be permeabilized by a detergent, such as polyethylene glycol (e.g., Triton X-100), Polyoxyethylene (20) sorbitan monolaurate (Tween-20), Saponin (a group of amphipathic glycosides), or chemicals such as methanol or acetone. In certain cases, fixation and permeabilization may be performed with the same reagent or set of reagents. Fixation and permeabilization techniques are discussed by Jamur et al. in "Permeabilization of Cell Membranes" (Methods Mol. Biol., 2010).

Detection of target nucleic acids in the cell, or "in-situ hybridization" (ISH), has previously been performed using fluorophore-tagged oligonucleotide probes. As discussed herein, mass-tagged oligonucleotides, coupled with ionization and mass spectrometry, can be used to detect target nucleic acids in the cell. Methods of in-situ hybridization are known in the art (see Zenobi et al. "Single-Cell Metabolomics: Analytical and Biological Perspectives," Science vol. 342, no. 6163, 2013). Hybridization protocols are also described in U.S. Pat. No. 5,225,326 and US Pub. No. 2010/0092972 and 2013/0164750, which are incorporated herein by reference.

Prior to hybridization, cells present in suspension or immobilized on a solid support may be fixed and permeabilized as discussed earlier. Permeabilization may allow a cell to retain target nucleic acids while permitting target hybridization nucleotides, amplification oligonucleotides, and/or mass-tagged oligonucleotides to enter the cell. The cell may be washed after any hybridization step, for example, after hybridization of target hybridization oligonucleotides to nucleic acid targets, after hybridization of amplification oligonucleotides, and/or after hybridization of mass-tagged oligonucleotides.

Cells can be in suspension for all or most of the steps of the method, for ease of handling. However, the methods are also applicable to cells in solid tissue samples (e.g., tissue sections) and/or cells immobilized on a solid support (e.g., a slide or other surface). Thus, sometimes, cells can be in suspension in the sample and during the hybridization steps. Other times, the cells are immobilized on a solid support during hybridization.

Target nucleic acids include any nucleic acid of interest and of sufficient abundance in the cell to be detected by the subject methods. Target nucleic acids may be RNAs, of which a plurality of copies exist within the cell. For example, 10 or more, 20 or more, 50 or more, 100 or more, 200 or more, 500 or more, or 1000 or more copies of the target RNA may be present in the cell. A target RNA may be a messenger NA (mRNA), ribosomal RNA (rRNA), transfer RNA (tRNA), small nuclear RNA (snRNA), small interfering RNA (siRNA), long noncoding RNA (lncRNA), or any other type of RNA known in the art. The target RNA may be 20 nucleotides or longer, 30 nucleotides or longer, 40 nucleotides or longer, 50 nucleotides or longer, 100 nucleotides or longer, 200 nucleotides or longer, 500 nucleotides or longer, 1000 nucleotides or longer, between 20 and 1000 nucleotides, between 20 and 500 nucleotides in length, between 40 and 200 nucleotides in length, and so forth.

In certain embodiments, a mass-tagged oligonucleotide may be hybridized directly to the target nucleic acid sequence. However, hybridization of additional oligonucleotides may allow for improved specificity and/or signal amplification.

In certain embodiments, two or more target hybridization oligonucleotides may be hybridized to proximal regions on the target nucleic acid, and may together provide a site for hybridization of an additional oligonucleotides in the hybridization scheme.

In certain embodiments, the mass-tagged oligonucleotide may be hybridized directly to the two or more target hybridization oligonucleotides. In other embodiments, one or more amplification oligonucleotides may be added, simultaneously or in succession, so as to hybridize the two or more target hybridization oligonucleotides and provide multiple hybridization sites to which the mass-tagged oligonucleotide can bind. The one or more amplification oligonucleotides, with or without the mass-tagged oligonucleotide, may be provided as a multimer capable of hybridizing to the two or more target hybridization oligonucleotides.

While the use of two or more target hybridization oligonucleotides improves specificity, the use of amplification oligonucleotides increases signal. Two target hybridization oligonucleotides are hybridized to a target RNA in the cell. Together, the two target hybridization oligonucleotides provide a hybridization site to which an amplification oligonucleotide can bind. Hybridization and/or subsequent washing of the amplification oligonucleotide may be performed at a temperature that allows hybridization to two proximal target hybridization oligonucleotides, but is above the melting temperature of the hybridization of the amplification oligonucleotide to just one target hybridization oligonucleotide. The first amplification oligonucleotide provides multiple hybridization sites, to which second amplification oligonucleotides can be bound, forming a branched pattern. Mass-tagged oligonucleotides may bind to multiple hybridization sites provided by the second amplification nucleotides. Together, these amplification oligonucleotides (with or without mass-tagged oligonucleotides) are referred to herein as a "multimer". Thus the term "amplification oligonucleotide" includes oligonucleotides that provides multiple copies of the same binding site to which further oligonucleotides can anneal. By increasing the number of binding sites for other oligonucleotides, the final number of labels that can be found to a target is increased. Thus, multiple labelled oligonucleotides are hybridized, indirectly, to a single target RNA. This is enables the detection of low copy number RNAs, by increasing the number of detectable atoms of the element used per RNA.

One particular method for performing this amplification comprises using the RNAscope® method from Advanced cell diagnostics, as discussed in more detail below. A further alternative is the use of a method that adapts the QuantiGene® FlowRNA method (Affymetrix eBioscience). The assay is based on oligonucleotide pair probe design with branched DNA (bDNA) signal amplification. There are more than 4,000 probes in the catalog or custom sets can be requested at no additional charge. In line with the previous paragraph, the method works by hybridization of target hybridization oligonucleotides to the target, followed by the formation of a branched structure comprising first amplification oligonucleotides (termed preamplification oligonucleotides in the QuantiGene® method) to form a stem to which multiple second amplification oligonucleotides can anneal (termed simply amplification oligonucleotides in the QuantiGene® method). Multiple mass-tagged oligonucleotides can then bind.

Another means of amplification of the RNA signal relies on the rolling circle means of amplification (RCA). There are various means why which this amplification system can be introduced into the amplification process. In a first instance, a first nucleic acid is used as the hybridisation nucleic acid wherein the first nucleic acid is circular. The first nucleic acid can be single stranded or may be double-stranded. It comprises as sequence complementary to the target RNA. Following hybridisation of the first nucleic acid to the target RNA, a primer complementary to the first nucleic acid is hybridised to the first nucleic acid, and used for primer extension using a polymerase and nucleic acids, typically exogenously added to the sample. In some instances, however, when the first nucleic acid is added to sample, it may already have the primer for extension hybridised to it. As a result of the first nucleic acid being circular, once the primer extension has completed a full round of replication, the polymerase can displace the primer and extension continues (i.e. without 5'→3' exonuclase activity), producing linked further and further chained copies of the complement of the first nucleic acid, thereby amplifying that nucleic acid sequence. Oligonucleotides comprising an elemental tag (RNA or DNA, or LNA or PNA and the like) as discussed above) may therefore be hybridised to the chained copies of the complement of the first nucleic acid. The degree of amplification of the RNA signal can therefore be controlled by the length of time allotted for the step of amplification of the circular nucleic acid.

In another application of RCA, rather than the first, e.g., oligonucleotide that hybridises to the target RNA being circular, it may be linear, and comprise a first portion with a sequence complementary to its target and a second portion which is user-chosen. A circular RCA template with sequence homologous to this second portion may then be hybridised to this the first oligonucleotide, and RCA amplification carried out as above. The use of a first, e.g., oligonucleotide having a target specific portion and user-chosen portion is that the user-chosen portion can be selected so as to be common between a variety of different probes. This is reagent-efficient because the same subsequent amplification reagents can be used in a series of reactions detecting different targets. However, as understood by the skilled person, when employing this strategy, for individual detection of specific RNAs in a multiplexed reaction, each first nucleic acid hybridising to the target RNA will need to have a unique second sequence and in turn each circular nucleic acid should contain unique sequence that can be hybridised by the labelled oligonucleotide. In this manner, signal from each target RNA can be specifically amplified and detected.

Other configurations to bring about RCA analysis will be known to the skilled person. In some instances, to prevent the first, e.g., oligonucleotide dissociating from the target during the following amplification and hybridisation steps, the first, e.g., oligonucleotide may be fixed following hybridisation (such as by formaldehyde).

Further, hybridisation chain reaction (HCR) may be used to amplify the RNA signal (see, e.g., Choi et al., 2010, Nat. Biotech, 28:1208-1210). Choi explains that an HCR amplifier consists of two nucleic acid hairpin species that do not polymerise in the absence of an initiator. Each HCR hairpin consists of an input domain with an exposed single-stranded toehold and an output domain with a single-stranded toehold hidden in the folded hairpin. Hybridization of the initiator to the input domain of one of the two hairpins opens the hairpin to expose its output domain. Hybridization of this (previously hidden) output domain to the input domain of the second hairpin opens that hairpin to expose an output domain identical in sequence to the initiator. Regeneration of the initiator sequence provides the basis for a chain reaction of alternating first and second hairpin polymerization steps leading to formation of a nicked double-stranded 'polymer'. Either or both of the first and second hairpins can be labelled with an elemental tag in the application of the methods and apparatus disclosed herein. As the amplification procedure relies on output domains of specific sequence, various discrete amplification reactions using separate sets of hairpins can be performed independently in the same process. Thus this amplification also permits amplification in multiplex analyses of numerous RNA species. As Choi notes, HCR is an isothermal triggered self-assembly process. Hence, hairpins should penetrate the sample before undergoing triggered self-assembly in situ, suggesting the potential for deep sample penetration and high signal-to-background ratios Hybridization may include contacting cells with one or more oligonucleotides, such as target hybridization oligonucleotides, amplification oligonucleotides, and/or mass-tagged oligonucleotides, and providing conditions under which hybridization can occur. Hybridization may be performed in a buffered solution, such as saline sodium-citrate (SCC) buffer, phosphate-buffered saline (PBS), saline-sodium phosphate-EDTA (SSPE) buffer, TNT buffer (having Tris-HCl, sodium chloride and Tween 20), or any other suitable buffer. Hybridization may be performed at a temperature around or below the melting temperature of the hybridization of the one or more oligonucleotides.

Specificity may be improved by performing one or more washes following hybridization, so as to remove unbound oligonucleotide. Increased stringency of the wash may improve specificity, but decrease overall signal. The stringency of a wash may be increased by increasing or decreasing the concentration of the wash buffer, increasing temperature, and/or increasing the duration of the wash. RNAse inhibitor may be used in any or all hybridization incubations and subsequent washes.

A first set of hybridization probes, including one or more target hybridizing oligonucleotides, amplification oligonucleotides and/or mass-tagged oligonucleotides, may be used to label a first target nucleic acid. Additional sets of hybridization probes may be used to label additional target nucleic acids. Each set of hybridization probes may be specific for a different target nucleic acid. The additional sets of hybridization probes may be designed, hybridized and washed so as to reduce or prevent hybridization between oligonucleotides of different sets. In addition, the mass-tagged oligonucleotide of each set may provide a unique signal. As such, multiple sets of oligonucleotides may be used to detect 2, 3, 5, 10, 15, 20 or more distinct nucleic acid targets.

Sometimes, the different nucleic acids detected are splice variants of a single gene. The mass-tagged oligonucleotide can be designed to hybridize (directly or indirectly through other oligonucleotides as explained below) within the sequence of the exon, to detect all transcripts containing that exon, or may be designed to bridge the splice junctions to detect specific variants (for example, if a gene had three exons, and two splice variants—exons 1-2-3 and exons 1-3—then the two could be distinguished: variant 1-2-3 could be detected specifically by hybridizing to exon 2, and variant 1-3 could be detected specifically by hybridizing across the exon 1-3 junction.

Histochemical Stains

The histochemical stain reagents having one or more intrinsic metal atoms may be combined with other reagents and methods of use as described herein. For example, histochemical stains may be colocalized (e.g., at cellular or subcellular resolution) with metal containing drugs, metal-labelled antibodies, and/or accumulated heavy metals. In certain aspects, one or more histochemical stains may be used at lower concentrations (e.g., less than half, a quarter, a tenth, etc.) from what is used for other methods of imaging (e.g., fluorescence microscopy, light microscopy, or electron microscopy).

To visualize and identify structures, a broad spectrum of histological stains and indicators are available and well characterized. The metal-containing stains have a potential to influence the acceptance of the imaging mass cytometry by pathologists. Certain metal containing stains are well known to reveal cellular components, and are suitable for use in the subject invention. Additionally, well defined stains can be used in digital image analysis providing contrast for feature recognition algorithms. These features are strategically important for the development of imaging mass cytometry.

Often, morphological structure of a tissue section can be contrasted using affinity products such as antibodies. They are expensive and require additional labelling procedure using metal-containin tags, as compared to using histochemical stains. This approach was used in pioneering works on imaging mass cytometry using antibodies labelled with available lanthanide isotopes thus depleting mass (e.g. metal) tags for functional antibodies to answer a biological question.

The subject invention expands the catalog of available isotopes including such elements as Ag, Au, Ru, W, Mo, Hf, Zr (including compounds such as Ruthenium Red used to identify mucinous stroma, Trichrome stain for identification of collagen fibers, osmium tetroxide as cell counterstain). Silver staining is used in karyotyping. Silver nitrate stains the nucleolar organization region (NOR)-associated protein, producing a dark region wherein the silver is deposited and denoting the activity of rRNA genes within the NOR. Adaptation to IMC may require that the protocols (e.g., oxidation with potassium permanganate and a silver concentration of 1% during) be modified for use lower concentrations of silver solution, e.g., less than 0.5%, 0.01%, or 0.05% silver solution.

Autometallographic amplification techniques have evolved into an important tool in histochemistry. A number of endogenous and toxic heavy metals form sulfide or selenide nanocrystals that can be autocatalytically amplified by reaction with Ag ions. The larger Ag nanocluster can then be readily visualized by IMC. At present, robust protocols for the silver amplified detection of Zn—S/Se nanocrystals have been established as well as detection of selenium through formation of silver-selenium nanocrystals. In addition, commercially available quantum dots (detection of Cd) are also autocatalytically active and may be used as histochemical labels.

Aspects of the subject invention may include histochemical stains and their use in imaging by elemental mass spectrometry. Any histochemical stain resolvable by elemental mass spectrometry may be used in the subject invention. In certain aspects, the histochemical stain includes one or more atoms of mass greater than a cut-off of the elemental mass spectrometer used to image the sample, such as greater than 60 amu, 80 amu, 100 amu, or 120 amu. For example, the histochemical stain may include a metal tag (e.g., metal atom) as described herein. The metal atom may be chelated to the histochemical stain, or covalently bound within the chemical structure of the histochemical stain. In certain aspects, the histochemical stain may be an organic molecule. Histochemical stains may be polar, hydrophobic (e.g., lipophilic), ionic or may comprise groups with different properties. In certain aspects, a histochemical stain may comprise more than one chemical.

Histochemical stains include small molecules of less than 2000, 1500, 1000, 800, 600, 400, or 200 amu. Histochemical stains may bind to the sample through covalent or non-covalent (e.g., ionic or hydrophobic) interactions. Histochemical stains may provide contrast to resolve the morphology of the biological sample, for example, to help identify individual cells, intracellular structures, and/or extracellular structures. Intracellular structures that may be resolved by histochemical stains include cell membrane, cytoplasm, nucleus, Golgi body, ER, mitochondria, and other cellular organelles. Histochemical stains may have an affinity for a type of biological molecule, such as nucleic acids, proteins, lipids, phospholipids or carbohydrates. In certain aspects, a histochemical stain may bind a molecule other than DNA. Suitable histochemical stains also include stains that bind extracellular structures (e.g., structures of the extracellular matrix), including stroma (e.g., mucosal stroma), basement membrane, interstitial stroma, proteins such as collage or elastin, proteoglycans, non-proteoglycan polysaccharides, extracellular vesicles, fibronectin, laminin, and so forth.

In certain aspects, histochemical stains and/or metabolic probes may indicate a state of a cell or tissue. For example, histochemical stains may include vital stains such as cisplatin, eosin, and propidium iodide. Other histochemical stains may stain for hypoxia, e.g., may only bind or deposit under hypoxic conditions. Probes such as Iododeoxyuridine (IdU) or a derivative thereof, may stain for cell proliferation. In certain aspects, the histochemical stain may not indicate the state of the cell or tissue. Probes that detect cell state (e.g., viability, hypoxia and/or cell proliferation) but are administered in-vivo (e.g., to a living animal or cell culture) be used in any of the subject methods but do not qualify as histochemical stains.

Histochemical stains may have an affinity for a type of biological molecule, such as nucleic acids (e.g., DNA and/or RNA), proteins, lipids, phospholipids, carbohydrates (e.g., sugars such as mono-saccharides or di-saccharides or polyols; oligosaccharides; and/or polysaccharides such as starch or glycogen), glycoproteins, and/or glycolipids. In certain aspects the histochemical stain may be a counterstain.

The following are examples of specific histochemical stains and their use in the subject methods:

Ruthenium Red stain as a metal-containing stain for mucinous stroma detection may be used as follows: Immunostained tissue (e.g., de-paraffinized FFPE or cryosection) may be treated with 0.0001-0.5%, 0.001-0.05%, less than 0.1%, less than 0.05%, or around 0.0025% Ruthenium Red (e.g., for at least 5 minutes, at least 10 minutes, at least 30 minutes, or around 30 min at 4-42° C., or around room temperature). The biological sample may be rinsed, for example with water or a buffered solution. Tissue may then be dried before imaging by elemental mass spectrometry.

Phosphotungstic Acid (e.g., as a Trichrome stain) may be used as a metal-containing stain for collagen fibers. Tissue sections on slides (de-paraffinized FFPE or cryosection) may be fixed in Bouin's fluid (e.g., for at least 5 minutes, at least 10 minutes, at least 30 minutes, or around 30 minutes at 4-42° C. or around room temperature). The sections may then be treated with 0.0001%-0.01%, 0.0005%-0.005%, or around 0.001% Phosphotangstic Acid for (e.g., for at least 5 minutes, at least 10 minutes, at least 30 minutes, or around 15 minutes at 4-42° C. or around room temperature). Sample may then be rinsed with water and/or buffered solution, and optionally dried, prior to imaging by elemental mass spectrometry. Triichrome stain may be used at a dilution (e.g., 5 fold, 10 fold, 20 fold, 50 fold or great dilution) compared to concentrations used for imaging by light (e.g., fluorescence) microscopy.

In some embodiments, the histochemical stain is an organic molecule. In some embodiments, the second metal is covalently bound. In some embodiments, the second metal is chelated. In some embodiments, the histochemical stain specifically binds cell membrane. In some embodiments, the histochemical stain is osmium tetroxide. In some embodiments, the histochemical stain is lipophilic. In some embodiments, the histochemical stain specifically binds an extracellular structure. In some embodiments, the histochemical stain specifically binds extracellular collagen. In some embodiments, the histochemical stain is a trichrome stain comprising phosphotungstic/phosphomolybdic acid. In some embodiments, trichrome stain is used after contacting the sample with the antibody, such as at a lower concentration than would be used for optical imaging, for instance wherein the concentration is a 50 fold dilution of trichrome stain or greater.

Metal-Containing Drugs

Metals in medicine is a new and exciting field in pharmacology. Little is known about the cellular structures that are involved in transiently storing metal ions prior to their incorporation into metalloproteins, nucleic acid metal complexes or metal-containing drugs or the fate of metal ions upon protein or drug degradation. An important first step towards unravelling the regulatory mechanisms involved in trace metal transport, storage, and distribution represents the identification and quantitation of the metals, ideally in context of their native physiological environment in tissues, cells, or even at the level of individual organelles and subcellular compartments. Histological studies are typically carried out on thin sections of tissue or with cultured cells.

A number of metal-containing drugs are being used for treatment of various diseases, however not enough is known about their mechanism of action or biodistribution: cisplatin, ruthenium imidazole, metallocene-based anti-cancer agents with Mo, tungstenocenes with W, B-diketonate complexes with Hf or Zr, auranofin with Au, polyoxomolybdate drugs. Many metal complexes are used as MRI contrast agents (Gd(III) chelates). Characterization of the uptake and biodistribution of metal-based anti-cancer drugs is of critical importance for understanding and minimizing the underlying toxicity.

The atomic masses of certain metals present in drugs fall into the range of mass cytometry. Specifically, cisplatin and others with Pt complexes (iproplatin, lobplatin) are extensively used as a chemotherapeutic drug for treating a wide range of cancers. The nephrotoxicity and myelotoxicity of platinum-based anti-cancer drugs is well known. With the methods and reagents described herein, their subcellular localization within tissue sections, and colocalization with mass-(e.g. metal-) tagged antibodies and/or histochemical stains can now be examined. Chemotherepeutic drugs may be toxic to certain cells, such as proliferating cells, through direct DNA damage, inhibition of DNA damage repair pathways, radioactivity, and so forth. In certain aspects, chemotherapeutic drugs may be targeted to tumor through an antibody intermediate.

In certain aspects, the metal containing drug is a chemotherapeutic drug. Subject methods may include administering the metal containing drug to a living animal, such as an animal research model or human patient as previously described, prior to obtaining the biological sample. The biological sample may be, for example, a biopsy of cancerous tissue or primary cells. Alternatively, the metal containing drug may be added directly to the biological sample, which may be an immortalized cell line or primary cells. When the animal is a human patient, the subject methods may include adjusting a treatment regimen that includes the metal containing drug, based on detecting the distribution of the metal containing drug.

The method step of detecting the metal containing drug may include subcellular imaging of the metal containing drug by elemental mass spectrometry, and may include detecting the retention of the metal containing drug in an intracellular structure (such as membrane, cytoplasm, nucleus, Golgi body, ER, mitochondria, and other cellular organelles) and/or extracellular structure (such as including stroma, mucosal stroma, basement membrane, interstitial stroma, proteins such as collage or elastin, proteoglycans, non-proteoglycan polysaccharides, extracellular vesicles, fibronectin, laminin, and so forth).

A histochemical stain and/or mass-(e.g. metal-) tagged SBP that resolves (e.g., binds to) one or more of the above structures may be colocalized with the metal containing drug to detected retention of the drug at specific intracellular or extracellular structures. For example, a chemotherapeutic drug such as cisplatin may be colocalized with a structure such as collagen. Alternatively or in addition, the localization of the drug may be related to presence of a marker of cell viability, cell proliferation, hypoxia, DNA damage response, or immune response.

In some embodiments, the metal containing drug comprises a non-endogenous metal, such as wherein the non-endogenous metal is platinum, palladium, cerium, cadmium, silver or gold. In certain aspects, the metal containing drug is one of cisplatin, ruthenium imidazole, metallocene-based anti-cancer agents with Mo, tungstenocenes with W, B-diketonate complexes with Hf or Zr, auranofin with Au, poly-oxomolybdate drugs, N-myristoyltransferase-1 inhibitor (Tris(dibenzylideneacetone) dipalladium) with Pd, or a derivative thereof. For example the drug may comprise Pt, and may be, for example, cisplatin, carboplatin, oxaliplatin, iproplatin, lobaplatin or a derivative thereof. The metal containing drug may include a non-endogenous metal, such as platinum (Pt), ruthenium (Ru), molybdenum (Mo), tungsten (W), hafnium (Hf), zirconium (Zr), gold (Au), gadolinium (Gd), palladium (Pd) or an isotope thereof. Gold compounds (Auranofin, for example) and gold nanoparticle bioconjugates for photothermal therapy against cancer can be identified in tissue sections.

Multiplexed Analysis

One feature of the disclosure is its ability to detect multiple (e.g. 10 or more, and even up to 100 or more) different target SBP members in a sample e.g. to detect multiple different proteins and/or multiple different nucleic acid sequences. To permit differential detection of these target SBP members their respective SBP members should carry different labelling atoms such that their signals can be distinguished. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g. which recognise different epitopes on the same protein. Thus, a method may use more antibodies than targets due to redundancy of this type. In general, however, the disclosure will use a plurality of different labelling atoms to detect a plurality of different targets.

If more than one labelled antibody is used with the disclosure, it is preferable that the antibodies should have similar affinities for their respective antigens, as this helps to ensure that the relationship between the quantity of labelling atoms detected and the abundance of the target antigen in the tissue sample will be more consistent across different SBPs (particularly at high scanning frequencies). Similarly, it is preferable if the labelling of the various antibodies has the same efficiency, so that the antibodies each carry a comparable quantity of the labelling atom.

In some instances, the SBP may carry a fluorescent label as well as an elemental tag. Fluorescence of the sample may then be used to determine regions of the sample, e.g. a tissue section, comprising material of interest which can then be sampled for detection of labelling atoms. E.g. a fluorescent label may be conjugated to an antibody which binds to an antigen abundant on cancer cells, and any fluorescent cell may then be targeted to determine expression of other cellular proteins that are about by SBPs conjugated to labelling atoms.

If a target SBP member is located intracellularly, it will typically be necessary to permeabilize cell membranes before or during contacting of the sample with the labels. For example, when the target is a DNA sequence but the labelled SBP member cannot penetrate the membranes of live cells, the cells of the tissue sample can be fixed and permeabilised. The labelled SBP member can then enter the cell and form a SBP with the target SBP member. In this respect, known protocols for use with IHC and FISH can be utilised.

A method may be used to detect at least one intracellular target and at least one cell surface target. In some embodiments, however, the disclosure can be used to detect a plurality of cell surface targets while ignoring intracellular targets. Overall, the choice of targets will be determined by the information which is desired from the method, as the disclosure will provide an image of the locations of the chosen targets in the sample.

As described further herein, specific binding partners (i.e., affinity reagents) comprising labelling atoms may be used to stain (contact) a biological sample. Suitable specific binging partners include antibodies (including antibody fragments). Labelling atoms may be distinguishable by mass spectrometry (i.e., may have different masses). Labelling atoms may be referred to herein as metal tags when they include one or more metal atoms. Metal tags may include a polymer with a carbon backbone and a plurality of pendant groups that each bind a metal atom. Alternatively, or in addition, metal tags may include a metal nanoparticle. Antibodies may be tagged with a metal tag by a covalent or non-covalent interaction.

Antibody stains may be used to image proteins at cellular or subcellular resolution. Aspects of the invention include contacting the sample with one or more antibodies that specifically bind a protein expressed by cells of the biological sample, wherein the antibody is tagged with a first metal tag. For example, the sample may be contacted with 5 or more, 10 or more, 15 or more, 20 or more, 30 or more, 40 or more, 50 or more antibodies, each with a distinguishable metal tag. The sample may further be contacted with one or more histochemical stains before, during (e.g., for ease of workflow), or after (e.g., to avoid altering antigen targets of antibodies) staining the sample with antibodies. The sample may further comprise one or more metal containing drugs and/or accumulated heavy metals as described herein.

Metal tagged antibodies for use in the subject inventions may specifically bind a metabolic probe that does not comprise a metal (e.g., EF5). Other metal tagged antibodies may specifically bind a target (e.g., of epithelial tissue, stromal tissue, nucleus, etc.) of traditional stains used in fluorescence and light microscopy. Such antibodies include anti-cadherin, anti-collagen, anti-keratin, anti-EFS, anti-Histone H3 antibodies, and a number of other antibodies known in the art.

Common histochemical stains that can be used herein include Ruthenium Red and Phosphotungstic Acid (e.g., as a Trichrome stain).

In addition to specific staining of sample introduce a stain into the sample, sometimes, the sample may contain a metal atom as a result of the tissue or the organism from which it was taken being administered a metal containing drug, or having accumulated metals from environmental exposure. Sometimes, tissues or animals may be tested in methods using this technique based on a pulse chase experimental strategy, to observe retention and clearance of a metal-containing material.

For instance, metals in medicine is a new and exciting field in pharmacology. Little is known about the cellular structures that are involved in transiently storing metal ions prior to their incorporation into metalloproteins, nucleic acid metal complexes or metal-containing drugs or the fate of metal ions upon protein or drug degradation. An important first step towards unravelling the regulatory mechanisms involved in trace metal transport, storage, and distribution represents the identification and quantification of the metals, ideally in context of their native physiological environment in tissues, cells, or even at the level of individual organelles and subcellular compartments. Histological studies are typically carried out on thin sections of tissue or with cultured cells.

A number of metal-containing drugs are being used for treatment of various diseases, however not enough is known about their mechanism of action or biodistribution: cisplatin, ruthenium imidazole, metallocene-based anti-cancer agents with Mo, tungstenocenes with W, B-diketonate complexes with Hf or Zr, auranofin with Au, polyoxomolybdate drugs. Many metal complexes are used as MRI contrast agents (Gd(III) chelates). Characterization of the uptake and biodistribution of metal-based anti-cancer drugs is of critical importance for understanding and minimizing the underlying toxicity.

The atomic masses of certain metals present in drugs fall into the range of mass cytometry. Specifically, cisplatin and others with Pt complexes (iproplatin, lobplatin) are extensively used as a chemotherapeutic drug for treating a wide range of cancers. The nephrotoxicity and myelotoxicity of platinum-based anti-cancer drugs is well known. With the methods and reagents described herein, their subcellular localization within tissue sections, and colocalization with metal tagged antibodies and/or histochemical stains can now be examined. Chemotherepeutic drugs may be toxic to certain cells, such as proliferating cells, through direct DNA damage, inhibition of DNA damage repair pathways, radioactivity, and so forth. In certain aspects, chemotherapeutic drugs may be targeted to tumor through an antibody intermediate.

In certain aspects, the metal containing drug is a chemotherapeutic drug. Subject methods may include administering the metal containing drug to a living animal, such as an animal research model or human patient as previously described, prior to obtaining the biological sample. The biological sample may be, for example, a biopsy of cancerous tissue or primary cells. Alternatively, the metal containing drug may be added directly to the biological sample, which may be an immortalized cell line or primary cells. When the animal is a human patient, the subject methods may include adjusting a treatment regimen that includes the metal containing drug, based on detecting the distribution of the metal containing drug.

The method step of detecting the metal containing drug may include subcellular imaging of the metal containing drug by elemental mass spectrometry, and may include detecting the retention of the metal containing drug in an intracellular structure (such as membrane, cytoplasm, nucleus, Golgi body, ER, mitochondria, and other cellular organelles) and/or extracellular structure (such as including stroma, mucosal stroma, basement membrane, interstitial stroma, proteins such as collage or elastin, proteoglycans, non-proteoglycan polysaccharides, extracellular vesicles, fibronectin, laminin, and so forth).

A histochemical stain and/or metal-tagged SBP that resolves (e.g., binds to) one or more of the above structures may be colocalized with the metal containing drug to detected retention of the drug at specific intracellular or extracellular structures. For example, a chemotherapeutic drug such as cisplatin may be colocalized with a structure such as collagen. Alternatively or in addition, the localization of the drug may be related to presence of a marker of cell viability, cell proliferation, hypoxia, DNA damage response, or immune response.

In certain aspects, the metal containing drug is one of cisplatin, ruthenium imidazole, metallocene-based anti-cancer agents with Mo, tungstenocenes with W, B-diketonate complexes with Hf or Zr, auranofin with Au, polyoxomolybdate drugs, N-myristoyltransferase-1 inhibitor (Tris (dibenzylideneacetone) dipalladium) with Pd, or a derivative thereof. For example the drug may comprise Pt, and may be, for example, cisplatin, carboplatin, oxaliplatin, iproplatin, lobaplatin or a derivative thereof. The metal containing drug may include a non-endogenous metal, such as platinum (Pt), ruthenium (Ru), molybdenum (Mo), tungstein (W), hafnium (Hf), zirconium (Zr), gold (Au), gadolinium (Gd), palladium (Pd) or an isotope thereof. Gold compounds (Auranofin, for example) and gold nanoparticle bioconjugates for photothermal therapy against cancer can be identified in tissue sections.

Exposure to heavy metals can occur though ingestion of food or water, contact through skin, or aerosol intake. Heavy metals may accumulate in soft tissues of the body, such that prolonged exposure has serious health effects. In certain aspect, the heavy metal may be accumulated in vivo, either through controlled exposure in an animal research model or though environmental exposure in a human patient. The heavy metal may be a toxic heavy metal, such as Arsenic (As), Lead (Pb), Antimony (Sb), Bismuth (Bi), Cadmium (Cd), Osmium (Os), Thallium (Tl), or Mercury (Hg).

Single Cell Analysis

Methods of the disclosure include laser ablation of multiple cells in a sample, and thus plumes from multiple cells are analysed and their contents are mapped to specific locations in the sample to provide an image. In most cases a user of the method will need to localise the signals to specific cells within the sample, rather than to the sample as a whole. To achieve this, the boundaries of cells (e.g. the plasma membrane, or in some cases the cell wall) in the sample can be demarcated.

Demarcation of cellular boundaries can be achieved in various ways. For instance, a sample can be studied using conventional techniques which can demarcate cellular boundaries, such as microscopy as discussed above. When performing these methods, therefore, an analysis system comprising a camera as discussed above is particularly useful. An image of this sample can then be prepared using a method of the disclosure, and this image can be superimposed on the earlier results, thereby permitting the detected signals to be localised to specific cells. Indeed, as discussed above, in some cases the laser ablation may be directed only to a subset of cells in the sample as determined to be of interest by the use of microscopy based techniques.

To avoid the need to use multiple techniques, however, it is possible to demarcate cellular boundaries as part of the imaging method of the disclosure. Such boundary demarcation strategies are familiar from IHC and immunocytochemistry, and these approaches can be adapted by using labels which can be detected. For instance, the method can involve labelling of target molecule(s) which are known to be located at cellular boundaries, and signal from these labels can then be used for boundary demarcation. Suitable target molecules include abundant or universal markers of cell boundaries, such as members of adhesion complexes (e.g. β-catenin or E-cadherin). Some embodiments can label more than one membrane protein in order to enhance demarcation.

In addition to demarcating cell boundaries by including suitable labels, it is also possible to demarcate specific organelles in this way. For instance, antigens such as histones (e.g. H3) can be used to identify the nucleus, and it is also possible to label mitochondrial-specific antigens, cytoskeleton-specific antigens, Golgi-specific antigens, ribosome-specific antigens, etc., thereby permitting cellular ultrastructure to be analysed by methods of the disclosure.

Signals which demarcate the boundary of a cell (or an organelle) can be assessed by eye, or can be analysed by computer using image processing. Such techniques are known in the art for other imaging techniques e.g. Arce et al. (2013; *Scientific Reports* 3, article 2266) describes a segmentation scheme that uses spatial filtering to determine cell boundaries from fluorescence images, Ali et al. (2011; *Mach Vis App*/23:607-21) discloses an algorithm which determines boundaries from brightfield microscopy images, Pound et al. (2012; *The Plant Cell* 24:1353-61) discloses the CellSeT method to extract cell geometry from confocal microscope images, and Hodneland et al. (2013; *Source Code for Biology and Medicine* 8:16) discloses the CellSegm MATLAB toolbox for fluorescence microscope images. A method which is useful with the disclosure uses watershed transformation and Gaussian blurring. These image processing techniques can be used on their own, or they can be used and then checked by eye.

Once cellular boundaries have been demarcated it is possible to allocate signal from specific target molecules to individual cells. It can also be possible to quantify the amount of a target analyte(s) in an individual cell e.g. by calibrating the methods against quantitative standards.

Reference Particles

As described herein, reference particles of known elemental or isotopic composition may be added to the sample (or the sample carrier) for use as a reference during detection of target elemental ions in the sample. In certain embodiments, reference particles comprise metal elements or isotopes, such as transition metals or lanthanides. For example, reference particles may comprise elements or isotopes of mass greater than 60 amu, greater than 80 amu, greater than 100 amu, or greater than 120 amu.

Target elements, such as labelling atoms, can be normalized within a sample run based on elemental ions detected from individual reference particles. For example, the subject methods may include switching between detecting elemental ions from individual reference particles and detecting only target elemental ions.

Pre-Analysis Sample Expansion Using Hydrogels

Conventional light microscopy is limited to approximately half the wavelength of the source of illumination, with a minimum possible resolution of about 200 nm. Expansion microscopy is a method of sample preparation (in particular for biological samples) that uses polymer networks to physically expand the sample and so increase the resolution of optical visualisation of a sample to around 20 nm (WO2015127183). The expansion procedures can be used to prepare samples for imaging mass spectrometry and imaging mass cytometry. By this process, a 1 µm ablation spot diameter would provide a resolution of 1 µm on an unexpanded sample, but with this 1 µm ablation spot represents ~100 nm resolution following expansion. In certain aspects, the size of the ablation spot (e.g., spot size) may be less than the size of the sample impinged by the radiation (e.g., laser, ion or electron beam radiation), for example when the energy required for ablation is greater than the energy at the edge of the beam impinging the sample.

Expansion microscopy of biological samples generally comprises the steps of: fixation, preparation for anchoring, gelation, mechanical homogenization, and expansion.

In the fixation stage, samples chemically fixed and washed. However, specific signalling functions or enzymatic functions such as protein-protein interactions as a function of physiological state can be examined using expansion microscopy without a fixation step.

Next, the samples are prepared so that they can be attached ("anchored") to the hydrogel formed in the subsequent gelation step. Here, SBPs as discussed elsewhere herein (e.g. an antibody, nanobody, non-antibody protein, peptide, nucleic acid and/or small molecule that can specifically bind to target molecules of interest in the sample)

are incubated with the sample to bind to the targets if present in the sample. Optionally, samples can be labelled (sometimes termed 'anchored') with a detectable compound useful for imaging. For optical microscopy, the detectable compound could comprise, for example, be provided by a fluorescently labelled antibody, nanobody, non-antibody protein, peptide, nucleic acid and/or small molecule that can specifically bind to target molecules of interest in the sample (US2017276578). For mass cytometry, including imaging mass cytometry, the detectable label could be provided by, for example, an elemental tag labelled antibody, nanobody, non-antibody protein, peptide, nucleic acid and/or small molecule that can specifically bind to target molecules of interest in the sample. In some instances, the SBP binding to the target does not contain a label but instead contains a feature that can be bound by a secondary SBP (e.g. a primary antibody that binds to the target and a secondary antibody that binds to the primary antibody, as common in immunohistochemical techniques). If only a primary SBP is used, this may itself be linked to a moiety that attaches or crosslinks the sample to the hydrogel formed in the subsequent gelation step so that the sample can be tethered to the hydrogel. Alternatively, if a secondary SBP is used, this may contain the moiety that attaches or crosslinks the sample to the hydrogel. In some instances, a third SBP is used, which binds to the secondary SBP. One exemplary experimental protocol is set out in Chen et al., 2015 (Science 347: 543-548) uses a primary antibody to bind to the target, a secondary antibody that binds to the primary antibody wherein the secondary antibody is attached to an oligonucleotide sequence, and then as a tertiary SBP a oligonucleotide complementary to the sequence attached to the secondary antibody, wherein the tertiary SBP comprised a methacryloyl group that can be incorporated into an acrylamide hydrogel. In some instances, the SBP comprising the moiety that is incorporated into the hydrogel also includes a label. These labels can be fluorescent labels or elemental tags and so used in subsequent analysis by, for example, flow cytometry, optical scanning and fluorometry (US2017253918), or mass cytometry or imaging mass cytometry.

The gelation stage generates a matrix in the sample, by infusing a hydrogel comprising densely cross-linked, highly charged monomers into the sample. For example, sodium acrylate along with the comonomer acrylamide and the crosslinker N-N'methylenebisacrylamide have been introduced into fixed and permeablised brain tissue (see Chen et al., 2015). When the polymer forms, it incorporates the moiety linked to the targets in the anchoring step, so that the targets in the sample become attached to the gel matrix.

The sample is then treated with a homogenizing agent to homogenize the mechanical characteristics of the sample so that the sample does not resist expansion (WO2015127183). For example, the sample can be homogenised by degradation with an enzyme (such as a protease), by chemical proteolysis, (e.g. by cyanogen bromide), by heating of the sample to 70-95 degrees Celsius, or by physical disruption such as sonication (US2017276578).

The sample/hydrogel composite is then expanded by dialyzing the composite in a low-salt buffer or water to allow the sample to expand to 4× or 5× its original size in 3-dimensions. As the hydrogel expands, so does the sample and in particular the labels attached to targets and the hydrogel expand, while maintaining their original three dimensional arrangement of the labels. Since the samples expand are expanded in low-salt solutions or water, the expanded samples are clear, allowing optical imaging deep into the samples, and allow imaging without introduction of significant levels of contaminating elements when performing mass cytometry (e.g. by use of distilled water or purified by other processes including capacitive deionization, reverse osmosis, carbon filtering, microfiltration, ultrafiltration, ultraviolet oxidation, or electrodeionization).

The expanded sample can then be analysed by imaging techniques, providing pseudo-improved resolution. For example, fluorescence microscopy can be used with fluorescent labels, and imaging mass cytometry can be used with elemental tags, optionally in combination. Due to the swelling of the hydrogel and the concomitant increase in distance between labels in the expanded sample vis-à-vis the native sample, labels which were not capable of being resolved separately previously (be that due to diffraction limit of visible light in optical microscopy, or spot diameter in IMC).

Variants of expansion microscopy (ExM) exist, which can also be applied using the apparatus and methods disclosed herein. These variants include: protein retention ExM (proExM), expansion fluorescent in situ hybridisation (ExFISH), iterative ExM (iExM),Iterative expansion microscopy involves forming a second expandable polymer gel in a sample that has already undergone a preliminary expansion using the above techniques. The first expanded gel is dissolved and the second expandable polymer gel is then expanded to bring the total expansion to up to ~20×. For instance, Chang et al., 2017 (Nat Methods 14:593-599) base the technique on the method of Chen et al. 2015 discussed above, with the substitution that the first gel is made with a cleavable cross linker (e.g., the commercially available crosslinker N,N'-(1,2-dihydroxyethylene) bisacrylamide (DHEBA), whose diol bond can be cleaved at high pH). Following anchoring and expansion of the first gel, a labelled oligonucleotide (comprising a moiety for incorporation into a second gel) and complementary to the oligonucleotide incorporated into the first gel was added to the expanded sample. A second gel was formed incorporating the moiety of the labelled oligonucleotide, and the first gel was broken down by cleavage of the cleavable linker. The second gel was then expanded in the same manner as the first, resulting in further spatial separation of the labels, but maintaining their spatial arrangement with respect to the arrangement of the targets in the original sample. In some instances, following expansion of the first gel, an intermediate "re-embedding gel" is used, to hold the expanded first gel in place while the experimental steps are undertaken, e.g., to hybridise the labelled SBP to the first gel matrix, form the unexpanded second hydrogel, before the first hydrogel and the re-embedding gel are broken down to permit the expansion of the second hydrogel. As before the labels used can be fluorescent or elemental tags and so used in subsequent analysis by, for example, flow cytometry, optical scanning and fluorometry, or mass cytometry or imaging mass cytometry, as appropriate.

Parameters and Applications

Methods and systems described herein may achieve a spot size diameter at or less than 500 nm, 400 nm, 300 nm, 200 nm, 100 nm, 50 nm, 30 nm, or 20 nm in diameter. In addition, the depth of the spot may be shallow; the spot depth may be similar to the diameter of the spot size or may be less than the diameter of the spot size. For example, a fs laser may ablate at a shallow depth (for example, when directed at the sample from the same side as plume formation, or if focused slightly above the sample when directed through a transparent substrate). A shallow spot depth may be at or less than 100 nm, 50 nm, 30 nm, 20 nm, or 10 nm. As such, some spots may only comprise one copy of a mass tag (e.g., one instance of a mass tag attached to a target, such as an RNA or protein). The mass tag may be attached to the target through an antibody intermediate and/or a hybridized oligonucleotide probe. In some cases, the same location (e.g., X-Y coordinate) may be sampled multiple times (e.g., at different Z-depths), improving detection by acquiring more of the sample and/or allowing for 3D imaging.

Resolution could be further improved through expansion of the sample (e.g., as expansion of a matrix crosslinking the sample such as by gel expansion).

Further, methods and systems described herein may provide improved ionization efficiency (such as by laser-SNMS, electron seeding prior to ablation, laser ionization post ablation, and/or laser ionization post initial neutralization). A postionization efficiency (percentage of labeling atoms ionized that remain charged through detection) may be at or above 5%, 10%, 20%, 30% or 50%. Further, formation of ions at or near the sample surface allow such ions to be transported directly by ion optics directly to a mass spectrometer, without losses incurred during fluidic transport of an ablation plume to ICP.

Alternatively or in addition, sensitivity may be improved with mass tags that comprise a large number of labeling atoms. Such a mass tag may comprise a metal chelating polymer, a metal nanoparticle (e.g., a metallocrystal or metal entrapped in a polymer matrix), or a hybridization scheme in which a plurality of metal tagged oligonucleotides hybridized to a RNA target or to an oligonucleotide conjugated to an affinity reagent (e.g., antibody) bound to a target protein. A high sensitivity mass tag may have at least 20, 50, 100, 200, 500, 1000, 2000, 5000, or 10000 labeling atoms.

As such, the methods and systems described herein may allow for detection of a single mass tag in a single spot (e.g., pixel). When single mass tags can be detected, the mass tag may comprise a unique combination of labeling atoms that are specific for the target bound by the mass tag (i.e., a target barcode). This may increase the number of targets that can be distinguished beyond the number of different labeling atom masses. A target barcode may have enriched isotopes from a plurality of different elements. For example, mass tags that comprise 5 out of 10 different labeling atoms allows for 10 choose 5 (i.e., 252) unique target barcodes. Mass tags that comprise 10 out of 20 different labeling atoms allows for 20 choose 10 (i.e., 184,756) unique target barcodes. As such, more than 50, 100, 200, 500, 1000, 2000, 5000, or 10000 different targets may be target barcoded. If target barcodes comprise the same expected number of different labeling atom masses, then any pixel comprising more than the expected number of target barcode labeling atom masses may be disregarded (i.e., it may not be possible to deconvolve which combination of target barcodes were present at that spot). In certain aspects, some mass tags may only comprise a single labeling atom mass selected from a first subset of masses, and other mass tags may be target barcoded and may comprise a unique combination of labeling atom masses selected from a second subset of masses that does not overlap with the first subset of masses. For example, mass tags to targets at high abundance may not be target barcoded. However, by controlling the concentration of mass tags and/or competing with affinity reagents that are not mass tagged, the instance of target barcoded mass tags that bind high abundance targets could be reduced to a level that allows for single copy detection per pixel. In some cases, a first imaging of the sample at a lower resolution and/or lower density of sampling may allow for non target barcoded mass tags to be detected, and for the identification of regions of interest. A higher resolution and/or higher density sampling may then be performed at the identified regions of interest to detect single copies of target barcoded mass tags.

To detect many targets at single molecule resolution in single cells, many pixels may need to be sampled from the cell. For example, a 10 micron cell that is roughly spherical could be sampled close to 1 billion times with a 10 nm spot size, provided the same location of the cell (e.g., X-Y coordinate) is sampled multiple times (e.g., at different Z-depths). A subset of pixels would have single target barcoded mass tags, and of those, many may have recurring target barcoded mass tags (which could be counted to quantify the expression level of the target). For example, if 1 million pixels are detected in a cell, and 10% of those pixels have a single copy of a target barcode mass tag, and the average number of each target barcode mass tag in the cell is 100, then there 1000 different target barcode mass tags could be detected in the cell.

Mass tags described above may be provided in a kit, optionally alongside or bound to affinity reagents and/or oligonucleotides so as to bind targets in a sample.

Definitions

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the disclosure.

EXAMPLES

Example 1

Protocol

The mouse gut was immersion fixed following organ harvesting using 2% PFA and 2.5% glutaraldehyde. The tissue was post-fixed with 2% Osmium Tetroxide for 1 hour. After dehydration the tissue sample was embedded in EPON resin and sectioned.

The 1000 nm tissue section was subjected to laser ablation and analyzed for the presence of osmium isotopes by Hyperion imaging system.

Results

Figure 11:
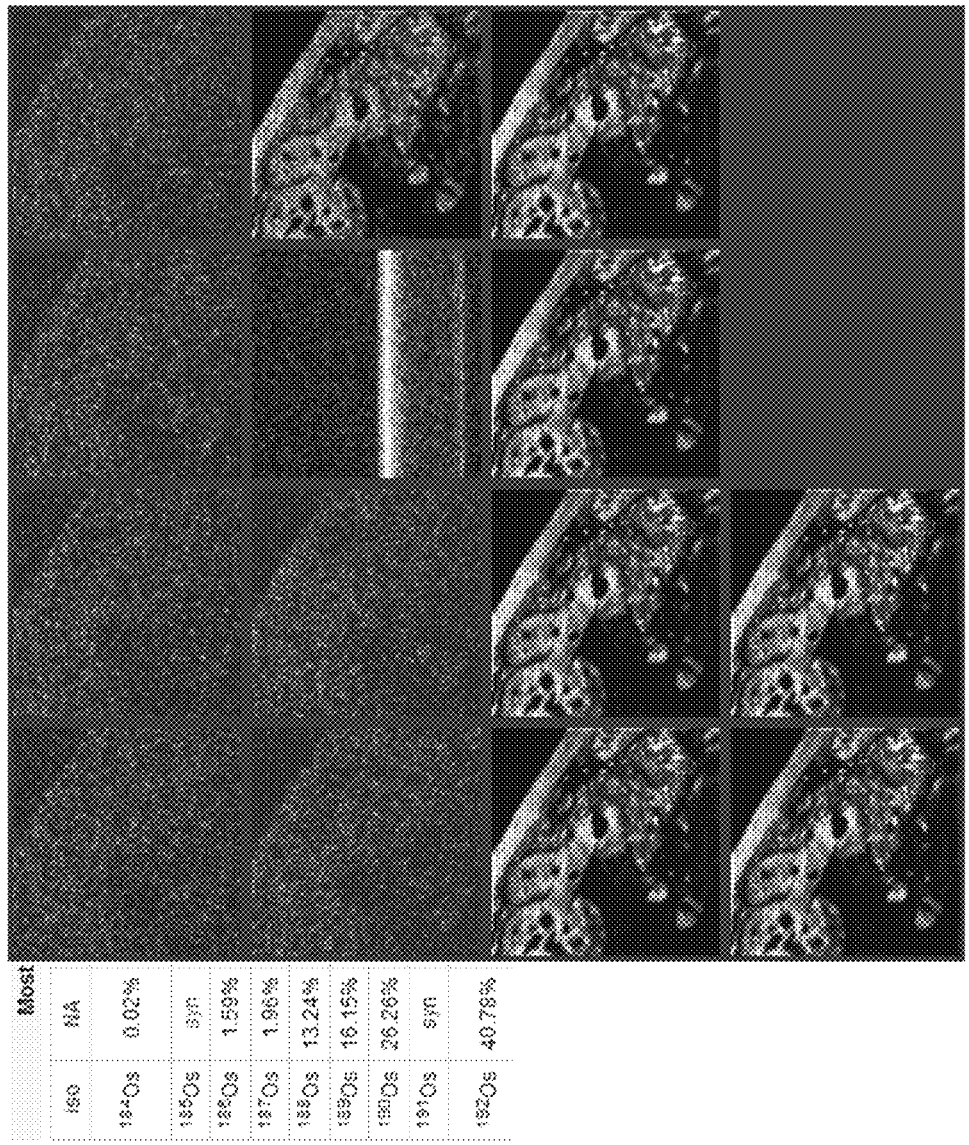
FIG. 11 shows an image showing the detection of various osmium isotopes in a sample prepared according to an exemplary method of the invention.

FIG. 11 illustrates detection of abundant osmium isotopes ($^{188}$Os, $^{189}$Os, $^{190}$Os and $^{192}$Os), as well as isotopes that are naturally low abundant (0.02% $^{184}$Os, 1.59% $^{186}$Os, 1.96% $^{187}$Os) present in the mouse gut tissue processed according to the standard immunoelectron microscopy protocols. The gut morphology is well defined with a dense outer layer of smooth muscle (upper left corner), mucosal epithelium with goblet cells and scattered stroma and immune cells beneath the epithelium.

Thus, electron microscopy 1 µm sections treated with 2% osmium tetroxide can be imaged for structural detail. The osmium tetroxide concentration used to fix tissue is determined not to be oversaturating for the IMC detector.

IMC settings: Mouse gut resin, He=1050, Ar=0_9, Z=2871, atten=30, 200 um×200 um, 200 Hz 200 pulses 200 um-sec, area1

Figure 12:
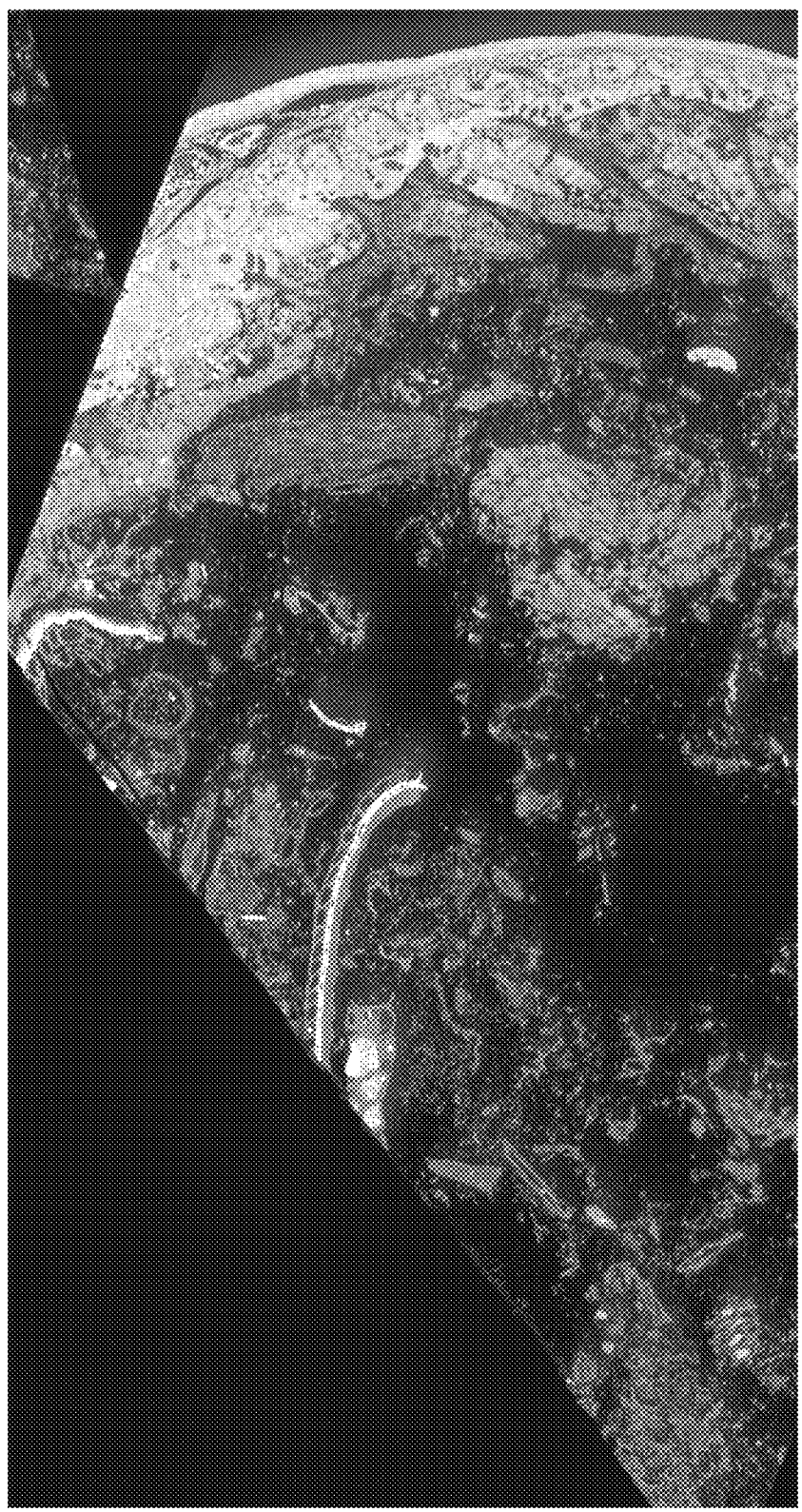
FIG. 12 shows an image showing the detection of various osmium isotopes in a sample prepared according to the exemplary method of the invention as used for FIG. 11.

A larger area of the mouse gut was also ablated. The image of FIG. 12 shows 2100×1087 um area, at 250 nm step size.

The invention claimed is:

1. A method of analyzing a sample by imaging mass spectrometry, comprising:
   radiating the sample in a sample chamber with a first energy source to release material from the sample;
   allowing the material to expand past the point of significant charge neutralization once ionized;
   ionizing the expanded material with an ionizing laser to:
      form a microplasma near the sample surface, and
      generate elemental ions; and
   analyzing the elemental ions by mass spectrometry.

2. The method of claim 1, wherein allowing the material to expand comprises allowing the material to expand into a partial vacuum in the sample chamber.

3. The method of claim 2, wherein the partial vacuum is 10-10,000 Pa.

4. The method of claim 1, wherein allowing the material to expand comprises allowing the material to expand for 100 ps to 10 ns before ionizing.

5. The method of claim 1, wherein the ionizing laser is an IR laser or a visible laser.

6. The method of claim 1, wherein the ionizing laser is a picosecond laser or a femtosecond laser.

7. The method of claim 1, further comprising directing ions resulting from the microplasma using ion optics positioned near the sample.

8. The method of claim 1, wherein analyzing is by a time-of-flight mass spectrometer or a magnetic sector mass spectrometer.

9. The method of claim 1, further comprising analyzing the sample by imaging mass cytometry.

10. The method of claim 1, wherein the first energy source is a laser.

11. The method of claim 10, wherein the laser has a wavelength of less than 300 nm.

12. The method of claim 10, wherein the laser is focused with an objective lens of numerical aperture of at least 0.9.

13. The method of claim 10, wherein the laser is focused to a spot size of 250 nm or less.

14. The method of claim 10, wherein the laser is positioned on the opposite side of a sample stage from the sample.

15. The method of claim 1, wherein the first energy source is an ion beam.

16. The method of claim 1, wherein the first energy source is an electron beam.

17. The method of claim 1, further comprising ablating the material from the sample using the first energy source, wherein the first energy source comprises a first laser source and a second laser source.

18. The method of claim 1, wherein the sample is a biological sample.

19. The method of claim 18, wherein the biological sample is a tissue sample that has a thickness of 100 nm or below.

20. The method of claim 18, wherein the biological sample comprises labelling atoms.

* * * * *